(12) United States Patent
Tu et al.

(10) Patent No.: US 11,397,176 B2
(45) Date of Patent: Jul. 26, 2022

(54) MEDICAL DIAGNOSTIC SYSTEM AND METHOD

(71) Applicant: Voyant Diagnostics, Inc., Skokie, IL (US)

(72) Inventors: Michael Tu, Skokie, IL (US); Prasanth Bijjam, Schaumburg, IL (US); Eric Shain, Glencoe, IL (US)

(73) Assignee: Everyplace Labs, Inc., Chicago, IL (US)

(*) Notice: Subject to any disclaimer, the term of this patent is extended or adjusted under 35 U.S.C. 154(b) by 812 days.

(21) Appl. No.: 16/015,417

(22) Filed: Jun. 22, 2018

(65) Prior Publication Data

US 2018/0372717 A1 Dec. 27, 2018

Related U.S. Application Data

(60) Provisional application No. 62/524,199, filed on Jun. 23, 2017.

(51) Int. Cl.
*G01N 33/493* (2006.01)
*G01N 35/00* (2006.01)
(Continued)

(52) U.S. Cl.
CPC .......... *G01N 33/493* (2013.01); *A61B 5/207* (2013.01); *A61B 10/007* (2013.01); *A61B 90/96* (2016.02);
(Continued)

(58) Field of Classification Search
CPC ........ G01N 33/493; G01N 2035/00108; A61B 10/007; A61M 2202/0496
See application file for complete search history.

(56) References Cited

U.S. PATENT DOCUMENTS 4,218,421 A * 8/1980 Mack, Jr. ............... G01N 31/22
422/561
4,466,445 A 8/1984 Abrams
(Continued)

FOREIGN PATENT DOCUMENTS

CN 104790487 B 5/2016
DE 102010061035 A1 6/2012
(Continued)

OTHER PUBLICATIONS

International Search Report and Written Opinion of the International Searching Authority for PCT/US19/66058; dated Apr. 7, 2020.
(Continued)

*Primary Examiner* — Sean P Dougherty
(74) *Attorney, Agent, or Firm* — McDonnell Boehnen Hulbert & Berghoff LLP

(57) ABSTRACT

A medical diagnostic system is provided to automate analysis of samples to predict a medical condition, such as pregnancy or chronic kidney disease. The system may provide test strip usage automation. The medical diagnostic system may include a sample collection component, collection cup contamination protection mechanism, sample volume control component, test strip reader component, which may be manifested as a lateral flow strip reader, flow reader, sample analytic component, data processing component, data communication component, networked data management component, and device cleaning mechanism. A method to automate analysis of samples to predict a medical condition using the medical diagnostic system is also provided.

19 Claims, 36 Drawing Sheets

(51) Int. Cl.

| | | |
|---|---|---|
| *G01N 35/10* | (2006.01) | |
| *A61B 10/00* | (2006.01) | |
| *A61F 5/44* | (2006.01) | |
| *A61M 25/00* | (2006.01) | |
| *A61M 39/08* | (2006.01) | |
| *A61B 90/96* | (2016.01) | |
| *A61B 90/98* | (2016.01) | |
| *E03D 9/00* | (2006.01) | |
| *G01N 1/20* | (2006.01) | |
| *E03D 11/13* | (2006.01) | |
| *A61B 5/20* | (2006.01) | |
| *G01N 1/00* | (2006.01) | |
| *G01N 1/10* | (2006.01) | |
| *A61B 5/00* | (2006.01) | |

(52) U.S. Cl.
CPC ............... *A61B 90/98* (2016.02); *A61F 5/44* (2013.01); *A61M 25/0017* (2013.01); *A61M 39/08* (2013.01); *E03D 9/00* (2013.01); *E03D 11/13* (2013.01); *G01N 1/20* (2013.01); *G01N 35/00029* (2013.01); *G01N 35/00722* (2013.01); *G01N 35/00732* (2013.01); *G01N 35/00871* (2013.01); *G01N 35/1004* (2013.01); *A61B 5/0022* (2013.01); *A61M 2202/0496* (2013.01); *A61M 2205/3584* (2013.01); *G01N 35/1097* (2013.01); *G01N 2001/002* (2013.01); *G01N 2001/1031* (2013.01); *G01N 2035/0091* (2013.01); *G01N 2035/00108* (2013.01); *G01N 2035/00752* (2013.01); *G01N 2035/00881* (2013.01)

(56) References Cited

U.S. PATENT DOCUMENTS

| | | | |
|---|---|---|---|
| 4,636,474 A | 1/1987 | Ogura et al. | |
| 4,943,416 A | 7/1990 | Kikuchi et al. | |
| 4,961,431 A | 10/1990 | Ikenaga et al. | |
| 4,962,550 A | 10/1990 | Ikenaga et al. | |
| 5,111,539 A | 5/1992 | Hiruta et al. | |
| 5,184,359 A * | 2/1993 | Tsukamura | A61B 5/02241 |
| | | | 4/314 |
| 5,198,192 A | 3/1993 | Saito et al. | |
| 5,415,840 A * | 5/1995 | Sano | G01N 35/00029 |
| | | | 422/105 |
| 5,596,948 A | 1/1997 | Ritchie | |
| 5,625,911 A | 5/1997 | Nakayama et al. | |
| 5,720,054 A | 2/1998 | Nakayama et al. | |
| 5,730,149 A | 3/1998 | Nakayama et al. | |
| 5,846,490 A | 12/1998 | Yokota et al. | |
| 5,945,341 A | 8/1999 | Howard, III | |
| 7,319,907 B2 | 1/2008 | Kasdan et al. | |
| 8,046,175 B2 | 10/2011 | Kuo et al. | |
| 2002/0193760 A1 | 12/2002 | Thompson | |
| 2003/0166259 A1 | 9/2003 | Smith et al. | |
| 2006/0096017 A1 * | 5/2006 | Yamasaki | G01F 23/00 |
| | | | 4/420 |
| 2006/0184064 A1 | 8/2006 | Paasch et al. | |
| 2007/0020143 A1 * | 1/2007 | Seidenstricker | ............................ |
| | | | G01N 35/00009 |
| | | | 422/400 |
| 2008/0178377 A1 * | 7/2008 | Liu | A47K 11/02 |
| | | | 4/450 |
| 2008/0193332 A1 | 8/2008 | Talmer et al. | |
| 2008/0286149 A1 * | 11/2008 | Roe | G01N 33/48764 |
| | | | 422/400 |
| 2009/0193571 A1 * | 8/2009 | Nakamura | A61G 7/02 |
| | | | 4/300 |
| 2009/0216099 A1 | 8/2009 | Kim | |
| 2010/0061889 A1 | 3/2010 | Park | |
| 2013/0053729 A1 | 2/2013 | Stevic-Wages et al. | |
| 2013/0261573 A1 * | 10/2013 | Rackley | A61F 5/4408 |
| | | | 604/328 |
| 2014/0276214 A1 | 9/2014 | Lipinsky et al. | |
| 2016/0000378 A1 * | 1/2016 | Hall | A61B 5/14532 |
| | | | 702/19 |
| 2016/0081669 A1 * | 3/2016 | Lowney, Jr. | A61B 10/0058 |
| | | | 600/573 |
| 2017/0022536 A1 | 1/2017 | Velazquez et al. | |
| 2017/0155917 A1 * | 6/2017 | Choi | H04N 19/50 |
| 2017/0224977 A1 * | 8/2017 | Shin | A61M 3/0262 |
| 2017/0284925 A1 * | 10/2017 | Spangenberg | G01N 15/14 |
| 2017/0295325 A1 * | 10/2017 | Yoon | H04N 5/23245 |
| 2018/0168556 A1 * | 6/2018 | Hall | A61B 10/007 |
| 2019/0073763 A1 | 3/2019 | Li et al. | |
| 2019/0293636 A1 * | 9/2019 | Tsuruoka | G16H 10/40 |

FOREIGN PATENT DOCUMENTS

| | | |
|---|---|---|
| DE | 10 2014 115914 A1 | 5/2016 |
| EP | 0278631 A1 | 8/1988 |
| EP | 0308080 A1 | 3/1989 |
| GB | 2505701 A | 3/2014 |
| JP | 63-118568 | 5/1988 |
| JP | S63 184057 A | 7/1988 |
| JP | 63-188761 | 8/1988 |
| JP | 63-241462 | 10/1988 |
| JP | 2001-265822 | 9/2001 |
| JP | 2004-125811 | 4/2004 |
| JP | 2011-080878 | 4/2011 |
| WO | 2009/094761 A1 | 8/2009 |
| WO | 2010/002097 A1 | 1/2010 |
| WO | 2012/074164 A1 | 6/2012 |
| WO | 2012/077933 A2 | 6/2012 |
| WO | 2015/066459 A1 | 5/2015 |
| WO | 2016/066372 | 5/2016 |
| WO | 2016/153452 A1 | 9/2016 |
| WO | 2018/167673 A1 | 9/2018 |

OTHER PUBLICATIONS

"Cole-Parmer Three-way solenoid pinch valve; 12 VDC, 1/8" ID × 1/4" OD tubing from Cole-Parmer"; URL: https://www.coleparmer.com/i/cole-parmer-three-way-solenoid-pinch-valve-12-vdc-1-8-id-x-1-4-od-tubing/9830246; retrieved on Jun. 14, 2018.

Written Opinion of the International Searching Authority for PCT/US18/38994; dated Sep. 7, 2018.

International Search Report for PCT/US18/38994; dated Sep. 7, 2018.

International Search Report and Written Opinion of the International Searching Authority for PCT/US21/34626; dated Aug. 26, 2021.

* cited by examiner

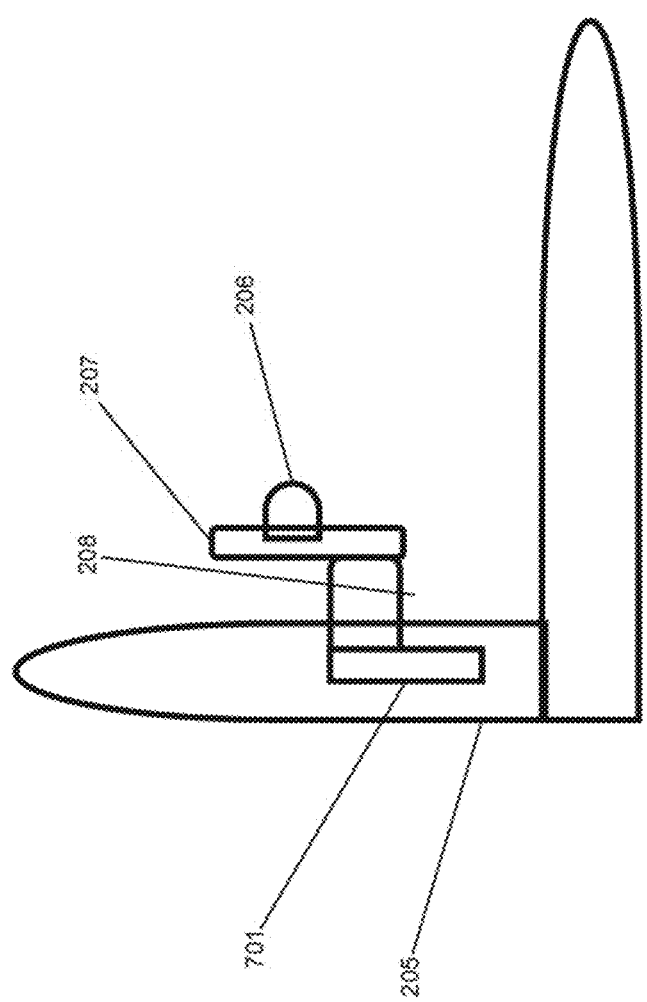

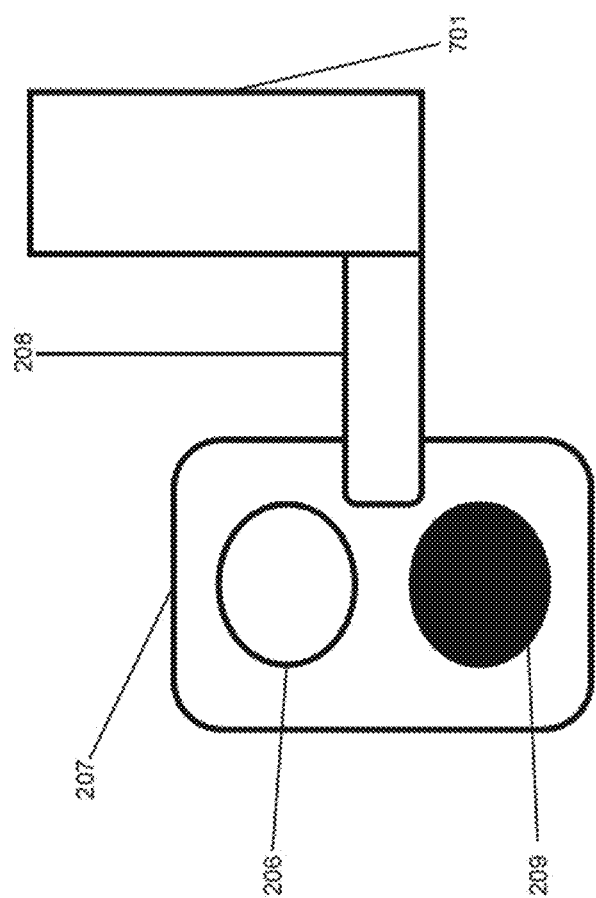

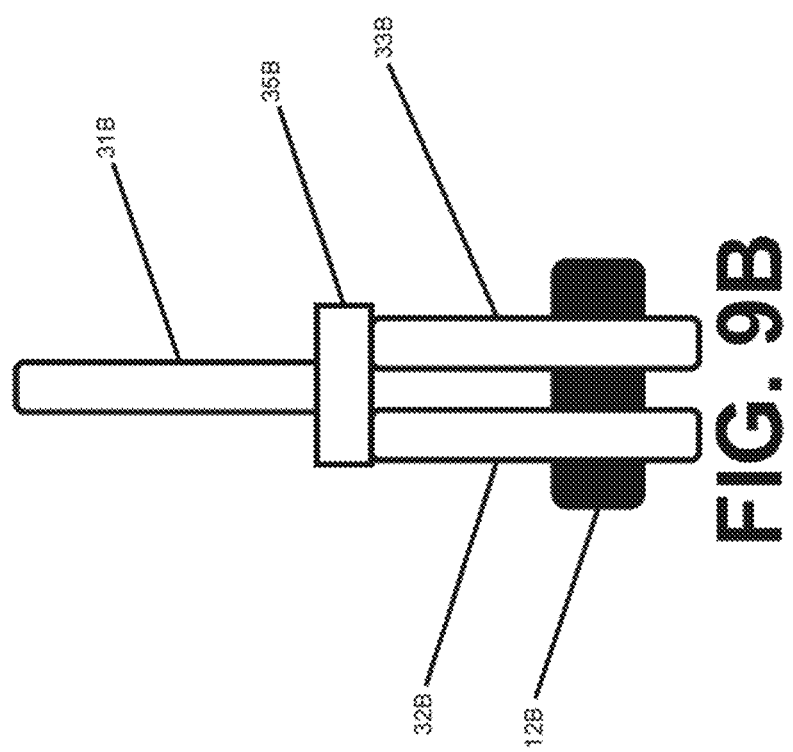

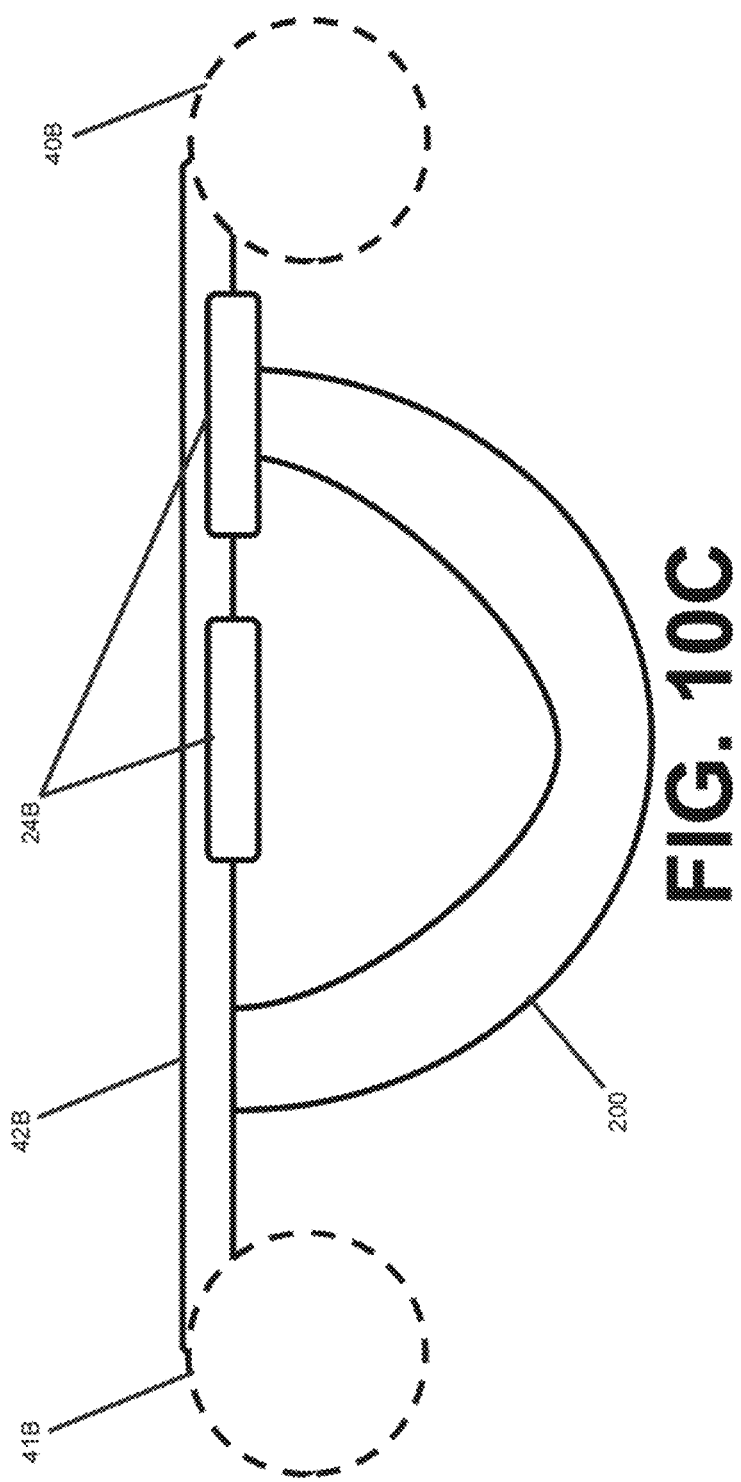

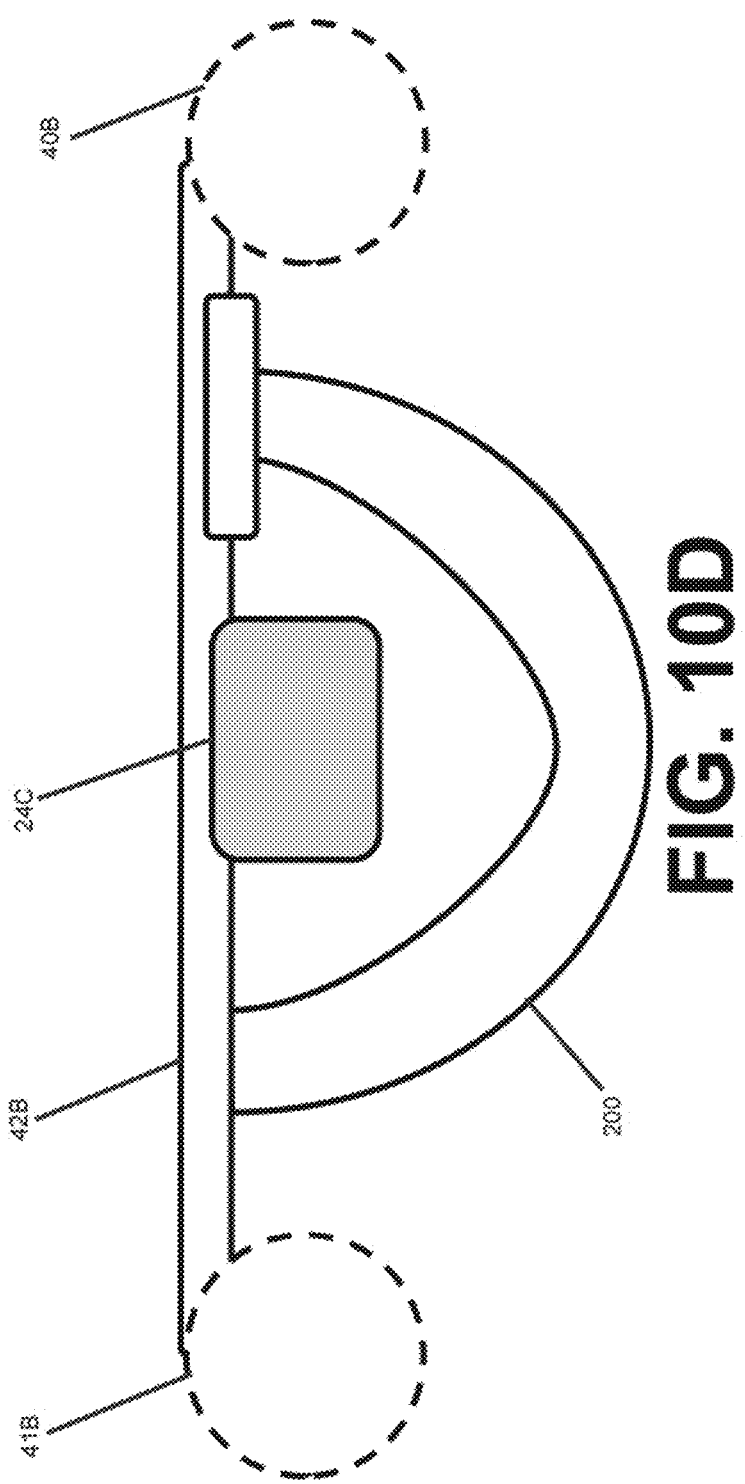

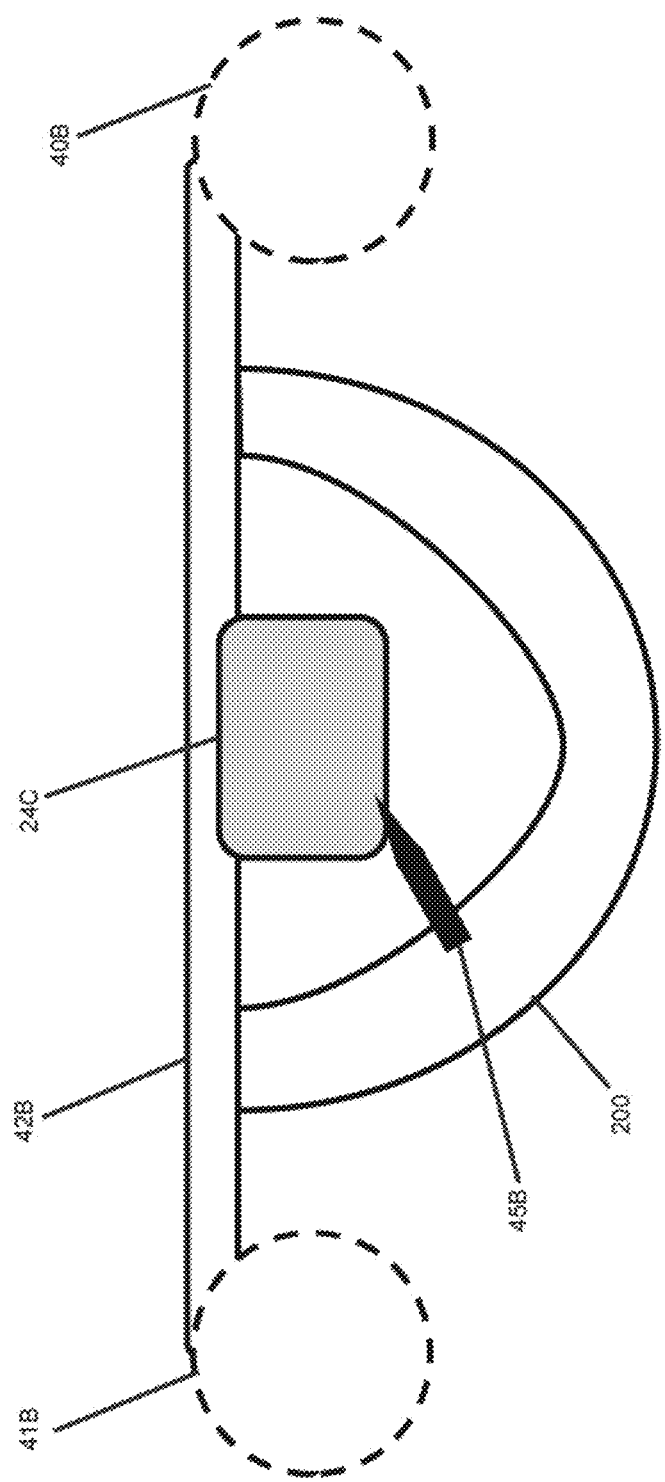

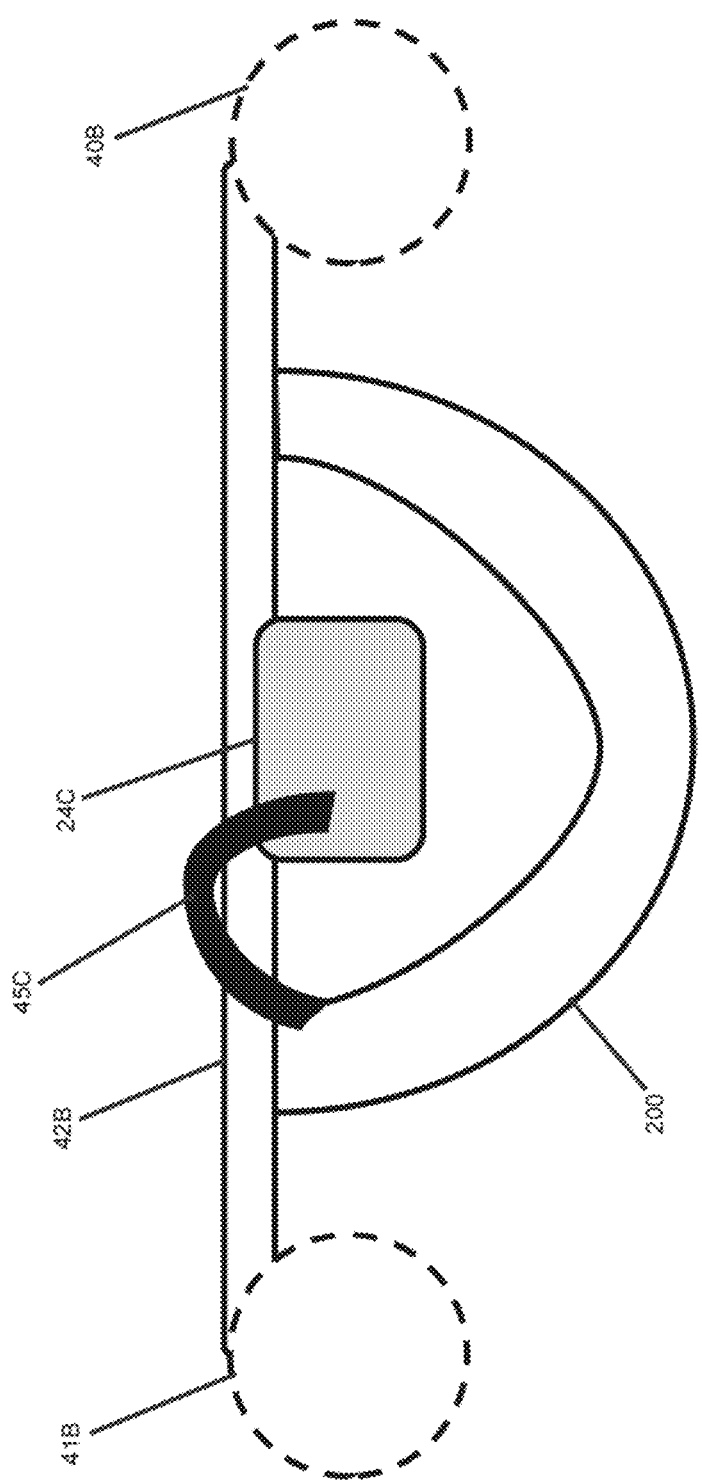

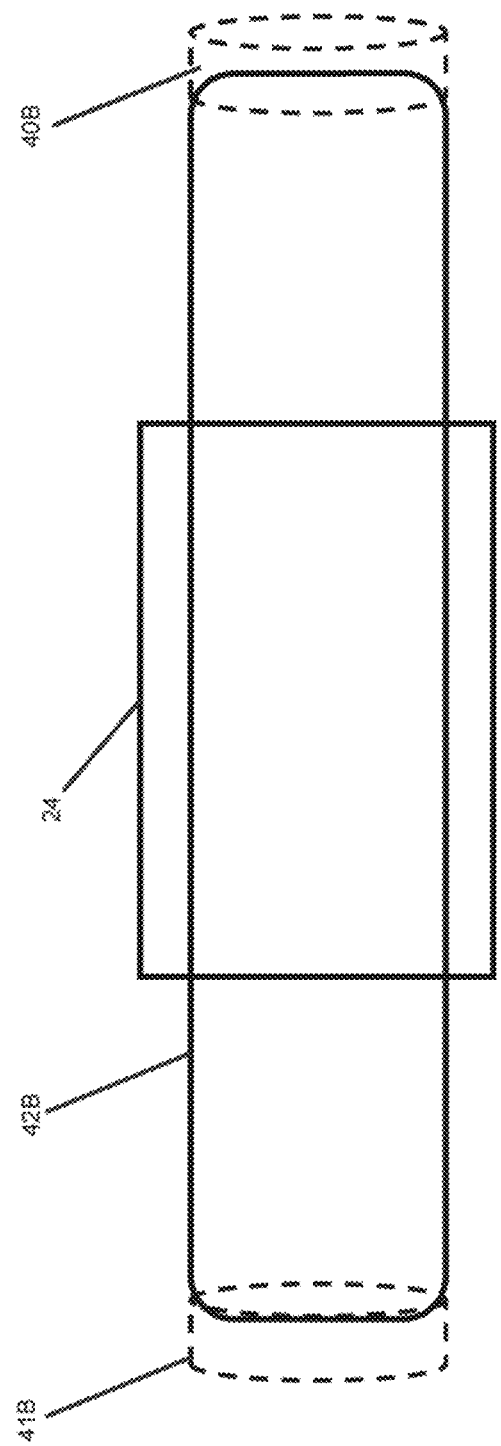

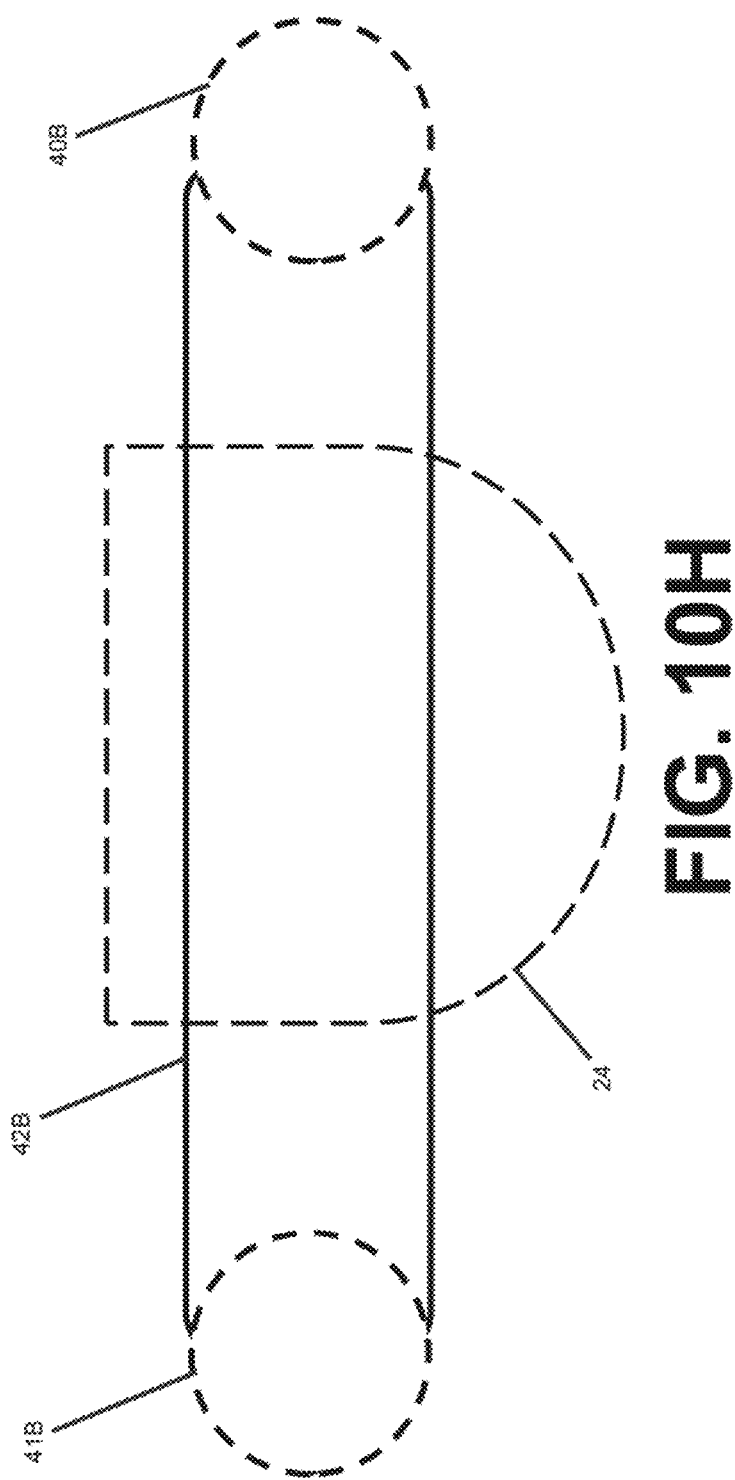

MEDICAL DIAGNOSTIC SYSTEM AND METHOD

CROSS-REFERENCE TO RELATED APPLICATIONS

The present application is a non-provisional patent application claiming priority to Provisional Patent Application No. 62/524,199, filed Jun. 23, 2017, the contents of which are hereby incorporated by reference.

FIELD OF THE INVENTION

The present disclosure relates to a medical diagnostic system. More particularly, the disclosure relates to automating analysis of samples to predict a medical condition.

BACKGROUND

Unless otherwise indicated herein, the materials described in this section are not prior art to the claims in this application and are not admitted to be prior art by inclusion in this section.

Women of child-bearing age visit U.S. emergency departments ("ED") an estimated 33.6 million times each year. Clinical standards recommend administering a point-of-care pregnancy test for this population since exclusion of pregnancy based on menstrual history is often not reliable on its own. The most common point-of-care test performed is a human chorionic gonadotropin (hCG) urine test. This intervention ensures that no woman of child-bearing age in the ED is put at risk while the provider is weighing diagnostic and/or treatment options. This clinical step is also important in other acute care settings (e.g., urgent care centers).

Minimizing risk of potential harm towards a fetus, especially in the most sensitive first trimester, is critical. Treatment plans that include radiological testing, anesthetic procedures, and prescription of teratogenic (category D or X) drugs all come with fetal risks. Such exposure can lead to growth retardation, congenital malformation, impaired brain function, childhood cancer, and miscarriage. In addition to adverse patient outcomes, pregnancy misdiagnosis can lead to repeat ED visits and medicolegal costs.

Current point-of-care pregnancy testing in the acute care setting is inadequate for at least two reasons: 1) in practice, implementation of the screening guideline is low, and 2) when the test is administered, user errors on the part of clinical staff can lead to unreliable results. Pregnancy testing in the ED is a time consuming, laborious, and complex process than can take up to 65 minutes. The standard, point-of-care urine test used today is not well-suited for high throughput, rapid mass screening.

Only an estimated 27% of acute care visits by women of child-bearing age include pregnancy testing. This lack of compliance persists even in situations where risky clinical action is taken. For example, a majority of ED visits by reproductive-aged women in which patients are prescribed teratogenic medications do not include a pregnancy test. This insufficient 27% of incoming women estimated to be screened leaves potentially 25 million unscreened women in emergency departments. Furthermore, an estimated 10% of women of child-bearing age are typically pregnant. With consideration of all these statistics, up to 2.5 million pregnant women are put at risk each year—up to half of all pregnancies.

Point-of-care urine tests, including pregnancy tests, are essentially waived from oversight. However, waived tests are often done incorrectly. The non-laboratory staff typically involved in point-of-care testing are often inadequately trained. User errors can include misplacement of samples, mislabeling of samples, testing process error, inaccurate visual interpretation, and incorrect entry of results into the electronic health record (EHR) system. Government spot checks of facilities that conduct point-of-care tests have found less than 50% compliance with policies meant to ensure proper care.

Of those women that are screened, the point-of-care pregnancy tests used in the emergency department are typically the same or similar tests as used at home. Such home tests are not designed for high throughput, rapid mass screening, or other needs of a typically busy emergency department. Current testing practices may also increase user errors that lead to false negatives, including misplacement of samples, mislabeling of samples, testing process errors, inaccurate visual interpretation, and incorrect entry of results into an electronic health record.

Of those women that are screened, they have to urinate into a cup to collect the sample. Urinating into a cup can be difficult for healthy patients, and may require assistance from medical staff for patients who are older, disabled, or too sick to do so by themselves. Either the patient or the medical staff will then need to carry the urine to a counter or to the lab for analysis, creating dissatisfaction for both the patient and staff.

Furthermore, it is estimated that nearly one hundred thirty million people are screened annually for routine urinalysis tests across multiple ambulatory settings, including, but not limited to, the emergency room, urgent care clinics, and private offices such as obstetrician/gynecologist offices and urologist offices.

Routine urinalysis exams consist of three tests: visual, chemical, and microscopic. Typically, visual tests and chemical tests are performed at the point-of-care. With visual tests, the urine's appearance is examined for turbidity and color. With chemical tests, currently, the urine is analyzed using a dipstick test with chemical strips that change colors if certain substances are present or if their levels are above normal. The clinical standard is a 10-panel assay that includes glucose, bilirubin, ketone, specific gravity, blood, pH, protein, urobilinogen, nitrite, and leukocyte esterase.

Furthermore, urine drug testing is performed to screen for the presence of certain illegal drugs and prescription drugs including amphetamines, methamphetamines, benziodiazepines, barbiturates, marijuana, cocaine, PCP, methadone, and opioids. Drug testing can be performed by the primary care physician to test for possible substance abuse. Employers can require employees to perform drug tests prior to being hired or during the course of their employment, in particular if the employees are required to be alert during the job. Drug and alcohol rehabilitation centers can perform drug tests on their patients in order to determine whether they are continuing to use drugs and/or alcohol. Drug testing can also be performed in the home setting to see if family members are using drugs.

Furthermore, it is estimated that more than two hundred million people are undiagnosed for chronic kidney disease ("CKD") globally. Chronic kidney disease is largely undiagnosed because it is asymptomatic, so regular testing may be overlooked. Chronic kidney disease progresses to kidney failure. Medicare is estimated to spend tens of billions of dollars per year to treat kidney failure. This number has been estimated to scale to over a half-trillion dollars of spending per year to treat kidney failure globally if most cases were treated. Unfortunately, many developing countries cannot treat kidney failure because the cost is prohibitive. Hence, diagnosing early-stage chronic kidney disease is paramount.

To cost effectively diagnose previously undiagnosed chronic kidney disease patients, The American College of Physicians recommends screening at-risk people with hypertension (estimated 1 billion people globally), people with diabetes (estimated 422 million people globally), and people above the age of 60 for chronic kidney disease. Furthermore, The American Society of Nephrology strongly recommends routinely screening all adults for chronic kidney disease to diagnose chronic kidney disease in its early stages when its progression can be halted.

Known as the "Silent Killer," chronic kidney disease is asymptomatic in its early stages, leaving an estimated 10 million adults in the U.S. undiagnosed. While only a small percentage of patients advance to end-stage kidney failure, treatment for those who do is costly. Nearly 6% of Medicare expenditures come from the 1% of covered patients who have end-stage renal failure. Including the cost to other payors and out-of-pocket expenses, the total annual bill for treating kidney failure is estimated at over $35 billion.

Furthermore, chronic kidney disease is highly co-morbid with other fatal chronic diseases. Beyond reducing the financial burden of end-stage kidney failure, managing chronic kidney disease early can also reduce the mortality rate and costs related to cardiovascular disease and diabetes among a much larger patient population. The American Society of Nephrology strongly recommends routinely screening all adults for chronic kidney disease to diagnose the disease in its early stages when its progression can be halted.

Screening and/or monitoring for biomarkers that indicate chronic kidney disease such as albumin to creatinine ratio or the level of beta-trace protein at the point of care is critical for chronic kidney disease. Point-of-care testing (PoCT) could improve adherence to screening recommendations and patient outcomes. Point-of-care testing is known to have a positive impact on operational efficiency and patient care. Such devices bring testing closer to the patient and provide physicians with faster results to expedite diagnosis and subsequent treatment. However, there are barriers to adoption. Physicians are often concerned about the reliability of test results from point-of-care testing. Errors can occur in the analytic phase of testing due to human error on the part of non-laboratory staff who are typically involved in current point-of-care testing techniques.

Therefore, a need exists to solve the deficiencies present in the prior art. What is needed is a system to facilitate testing of samples for biomarkers indicative of a medical condition. What is needed is a system to facilitate collection of urine for substantially automated testing. What is needed is a system to automate testing of samples using optically and/or electronically detectable indicators. What is needed is a system to communicate detected biomarkers indicative of a condition to a network-connected electronic computing device. What is needed is a method of substantially automated collecting, processing, testing, and optically and/or electronically analyzing indicators to predict a medical condition. What is needed is a method including a substantially automated test for and detection of indicators of chronic kidney disease, pregnancy, and/or other medical conditions within an acceptable margin of error.

SUMMARY

The specification and drawings disclose embodiments that relate to medical diagnostic systems and methods.

An aspect of the disclosure advantageously provides a system to facilitate testing of samples for biomarkers indicative of a medical condition. An aspect of the disclosure advantageously provides a system to facilitate collection of urine for substantially automated testing. An aspect of the disclosure advantageously provides a system to automate testing of samples using optically and/or electronically detectable indicators. An aspect of the disclosure advantageously provides a system to communicate detected biomarkers indicative of a condition to a network-connected electronic computing device. An aspect of the disclosure advantageously provides a method of substantially automated collecting, processing, testing, and optically and/or electronically analyzing indicators to predict a medical condition. An aspect of the disclosure advantageously provides a method including a substantially automated test for and detection of indicators of chronic kidney disease, pregnancy, and/or other medical conditions within an acceptable margin of error.

Applications based on this disclosure may include substantially automated urine pregnancy testing, for example, in the emergency department through urine testing of human chorionic gonadotropin (hCG). This emergency department use case may advantageously automate away or substantially reduce user error. Previously, examples of user errors may occur when nurses fail to label the urine cups with patient identification. As a result, the urine sample for a patient can get switched up, which can lead to a false negative result. This problem can lead to females who are pregnant being treated in the emergency department or urgent care facility as if they are not pregnant, potentially exposing the fetus to drugs and radiation that can harm it for the rest of its life. The substantially automated testing of this disclosure may advantageously reduce the risk of this devastating problem.

Solutions provided throughout this disclosure are intended to automate the pregnancy testing process in the emergency department, providing results in typically less than 5 minutes without clinical and non-clinical staff input. In one example, the system can be installed on a toilet, with the device resting on the toilet tank. The device is connected to a urine collection cup that is installed on or inside the toilet bowl. The patient will typically be able to scan his or her hospital barcode ID on the device before urinating into the collection cup that is installed on or inside the toilet bowl. The add-on device to the toilet may automatically collects, process, and analyze the urine to determine the pregnancy status of the patient. The system then may automatically send the test results to an electronic health record.

Solutions provided throughout this disclosure substantially automate the entire emergency department pregnancy testing process from the point of specimen collection to sending the test result to the electronic health record. The system also substantially automates the sample processing, dispensing, testing, analysis, and cleaning processes. The system substantially automates the cleaning processes of the device, its collection cup, and the connections between the device and its collection cup. The system also substantially automates the test strip usage process.

The solutions to the deficiencies in the prior art provided throughout this disclosure are intended to improve patient outcomes without increasing the clinical burden. Eliminating labor costs and decreasing testing time, systems included by this disclosure may substantially increase, for example, double, the number of women screened typically without increasing overall cost. Removing user errors also drives more reliable results. The technology discussed throughout this disclosure is superior to existing manual and semi-automated urine pregnancy tests in both speed and reliability.

Various embodiments of the solution described throughout this disclosure facilitate previously undiagnosed chronic kidney disease ("CKD") to be diagnosed through time-efficient, relatively inexpensive, and accurate mass screening. Various embodiments described throughout this disclosure may provide for an add-on device installable to toilets or other existing devices that substantially automatically analyzes urine for biomarkers of a detectable condition, for example, chronic kidney disease. Biomarkers may include, without limitation, beta-trace protein, albumin, and creatinine. Collectively, the biomarkers can provide substantially accurate indicators of a detectable condition, for example CKD or pregnancy, from its early through late stages. The solutions provided throughout this disclosure can be installed onto an existing device found at a testing location. For example, solutions described throughout this disclosure may be installed on a toilet in a physician's office, a clinic, such as a walk-in clinic, patient home, and/or a screening van as a point-of-care screening device for CKD and other conditions. Patients, for example, adults above the age of 45 or with a previous history of hypertension or diabetes, may visit a screening facility, simply urinate into a device of this disclosure, and quickly be diagnosed for a medical condition, for example CKD, in its early stages.

Solutions provided throughout this disclosure may enable emergency departments, urgent care facilities, and other locations to implement best practices, including mass pregnancy screening. This disclosure provides a solution to the longstanding problem that, despite clinical standards, only about 27% of emergency department visits by women of childbearing age include pregnancy testing because the existing urine testing process for pregnancy is time consuming, complex, and laborious. This disclosure aims to solve problems in the current state of the art, since currently up to 2.5 million pregnant women are put at risk of harmful treatments annually. This disclosure, for example, provides an add-on device to toilets to enable mass pregnancy screening in emergency departments, urgent care facilities, and other locations by substantially automatically determining a woman's pregnancy status through the urine without requiring clinical staff intervention, creating a faster, lower cost, and more reliable process.

The following disclosure provides for an add-on device installable to existing equipment to indicate a presence of a detectable medical condition. For example, the disclosure may relate to a device installable on toilets that automatically tests urine for CKD and other conditions in minutes. By substantially automating a process that requires little input from non-laboratory staff, devices provided by this disclosure advantageously reduce the required training and technology knowledge needed to operate a point-of-care testing ("PoCT") device. One or more of the devices provided by this disclosure may advantageously enable reliable testing anywhere there is a toilet, such as in a physician's office, a retail walk-in clinic, a screening van, emergency department, urgent care facility, or other care areas, such as in a hospital.

Additionally, the components and operations of this disclosure may advantageously speed up the urine testing process per patient to less than 5 minutes. This time is a substantial improvement over the current industry standard, which is believed to be about 65 minutes from the time the patient arrives at the waiting room until clinical action is first taken.

The components and operations of this disclosure may advantageously increase detection of kidney stone development, for example, by analyzing pH. The testing may determine diet effectiveness, type of kidney stone developing, and other factors. The testing provided by this disclosure may eliminate unnecessary trips to a urologist for wasteful scans to rule out kidney stone. Similarly, automated urinalysis to detect urinary tract infections (UTI) may be performed at pharmacies, clinics, and offices of offsite nurse practitioners who can prescribe antibiotics (for UTI). This can be attractive for patients who do not want to pay a high deductible to go to a physician's office.

Additionally, the components and operations of this disclosure may be used to perform drug screening. In the age of heroin usage and increasing addiction, more kids and adults are overdosing on drugs. Similarly, emergency department, urgent care, and other drug screening may be facilitated, potentially allowing for screening of everyone as they come in.

Additionally, the components and operations of this disclosure may be used to screen for diabetic conditions. In the example of diabetic CKD, urine may be screened for urine microalbumin, such as creatinine for diabetes. This may change the management for ACE inhibitors, which are traditionally sent to a lab for testing. In another example of borderline diabetics, urine can be screened for glucose to see if a patient is developing diabetes. The testing provided by this disclosure may provide at-home monitoring of glucose in urine, which may improve patient satisfaction because they no longer need a daily blood prick.

Diabetes patients are supposed to blood prick themselves about 4-6 times per day. This inconvenience may lead to patients with diabetes tending not to blood prick themselves because they feel they can "sense" when their blood sugar is low or high. When these patients "sense" that their blood sugar is low or high, they blood prick themselves to get a quantitative blood glucose measurement to determine how much medication they should take to increase or decrease their blood glucose levels. "Sensing" can lead to inaccuracies that can have adverse clinical outcomes. For these type of patients, a passive at-home monitoring device, like one provided by this disclosure, for urine glucose could potentially avoid these inaccuracies from "sensing." From another perspective, children with diabetes and newly diagnosed diabetes are not very good at "sensing" their blood sugar levels, so having a passive at-home monitoring device for urine glucose could be beneficial to them.

Additionally, the components and operations of this disclosure may be used for detection of chronic diseases. Currently, patients need to titrate up and titrate down treatment. This disclosure provides a technique to test metabolites in urine to determine current titration level, which may reduce epilepsy, resulting seizures, and minimize hospital stay caused by these seizures.

Additionally, the components and operations of this disclosure may be used for monitoring medication adherence, in particular for cardiovascular purposes. Currently, physicians rely on patients to provide information about whether they are adhering to their medication. Now, physicians can more efficiently have patients test their urine for biomarkers that can be used to check medication adherence. This disclosure can further automate urine testing in either a clinical setting or the home setting to test whether the medication affects urine biomarkers.

Additionally, the components and operations of this disclosure may be used for at-home monitoring of patients for particular biomarkers. Currently, physicians may prescribe a treatment to a patient, but will not be able to track how effective the treatment is with a high frequency. Patients need to periodically go back to the clinical setting, so the physician and/or clinician can conduct a urine and/or blood test to look for increases in the concentration of a biomarker or combination of biomarkers, which is an indication that treatment is not effective and needs modification. Between patient visits to the clinical setting, time lags can occur on the order of days, weeks, and months between the patient undergoes treatment at home and when the physician measures treatment efficacy in the clinical setting.

With the components and the operations of this disclosure, physicians and/or clinicians can prescribe patients to install the system in their homes, in order to passively track over time with high frequency the concentration of one or many urinary biomarkers that are indications of disease progression and treatment efficacy. The system can track the concentration of urinary biomarkers whenever the patient urinates into the toilet at home. The system will securely send the test results to the clinical setting for the physician and/or clinicians to review the effectiveness of the treatment and/or the disease progression. The system will also analyze the trend over time of the concentration of the biomarker(s) compared to baseline biomarker concentration(s) unique to each patient. As an example, if the change in concentration of a specific biomarker exceeds a threshold compared to the baseline biomarker concentration, the system will automatically detect this trend and notify the patient and clinicians of treatment ineffectiveness and the disease progression.

Additionally, the components and operations of this disclosure may be used for performing general urinalysis tests. Currently, physicians rely on dipstick tests and microscopic tests to analyze the levels or evidence of glucose, bilirubin, ketone, specific gravity, blood, pH, protein, urobilinogen, nitrite, and leukocyte esterase in urine. This disclosure provides a technique to test or measure the general urinalysis assays.

In one aspect, the disclosure is directed to a system. The system includes a collection component configured to collect a urine sample from a patient. The system also includes a plurality of test strips configured to indicate a condition of the patient when exposed to the urine sample. Further, the system includes a fluid transportation system. The fluid transportation system is configured to transport a portion of the urine sample from the collection component to a first test strip of the plurality of test strips at a predetermined position relative to the collection component. The fluid transportation system is also configured to expose the first test strip to the portion of the urine sample. Further, the fluid transportation system is configured to deliver fresh water or another cleaning solution to the collection component to clean the collection component. In addition, the system includes a sensor configured to capture an image of the first test strip exposed to the portion of the urine sample when the first test strip is near the sensor. The image indicates the condition of the patient. Still further, the system includes a computing device configured to analyze the image of the first test strip captured by the sensor in order to determine the condition of the patient. Yet further, the system includes a motor. The motor is configured to position the first test strip near the sensor after the first test strip is exposed to the portion of the urine sample. The motor is also configured to position a second test strip of the plurality of test strips at the predetermined position after the first test strip is exposed to the portion of the urine sample.

In some embodiments, the collection component is configured to be installed on or inside a toilet bowl. The collection component activates or deactivates based on a user input.

In some embodiments, the system also includes an electronically-stored medium. The electronically-stored medium is configured to store the determined condition of the patient. The computing device is configured to transmit the determined condition of the patient to an additional electronically-stored medium for inclusion in an electronic health record of the patient. The electronic health record of the patient contains additional health data relating to the patient.

In some embodiments, the additional data relating to the patient includes at least one of a unique patient identifier, a result of the test strip, or an image of the test strip.

In some embodiments, the system also includes a user interface configured to share the image or the determined condition of the patient with a physician, the patient, or another selected party.

In some embodiments, the system also includes a scanner configured to detect an identification of the patient. The scanner includes a barcode scanner or a radio-frequency identification (RFID) scanner. Upon the scanner detecting the identification of the patient, the system is configured to collect, process, and analyze the urine sample in an automated fashion. The computing device is configured to transmit the condition of the patient to an electronically-stored medium for inclusion in an electronic health record of the patient based on the identification of the patient.

In some embodiments, the collection component is connectable to a catheter or urine collection bag.

In some embodiments, the fluid transportation system includes a tube. The tube is made of a hydrophobic material that allows fluid to pass through the tube without sticking to the walls of the tube.

In some embodiments, the material that allows fluid to pass through the tube without sticking to the walls of the tube includes silicone, polytetrafluoroethylene (PTFE/TEFLON®), or polyethylene.

In some embodiments, the system also includes an anti-contamination film connected to a first set of opposing reels and located above or adjacent to the collection component. When rotated by a separate motor, the first set of opposing reels is configured to move a used area of the anti-contamination film away from the collection component after the first test strip is exposed to the portion of the urine sample. When rotated by the separate motor, the first set of opposing reels is also configured to move an unused area of the anti-contamination film toward from the collection component after the first test strip is exposed to the portion of the urine sample.

In some embodiments, the collection component includes a valve or adjusted aperture configured to release the urine sample after the first test strip is exposed to the portion of the urine sample.

In some embodiments, the fluid transportation system is configured to deliver the fresh water or another cleaning solution to the collection component to clean the collection component after the urine sample is released.

In some embodiments, the tests strips include aptamers, antibodies, chemical reagents, biomolecules, or a substance that binds or reacts to the urine sample.

In some embodiments, the plurality of test strips is housed in a replaceable cartridge including a second set of opposing reels. The plurality of test strips is located on a belt within the replaceable cartridge that spans the second set of opposing reels. Each of the opposing reels in the second set of opposing reels is rotatable by the motor in order to move the belt.

In some embodiments, the replaceable cartridge includes only test strips specifically used to indicate a predetermined condition. The predetermined condition includes chronic kidney disease (CKD), glucose levels, opiate levels, albumin to creatinine ratio, human chorionic gonadotropin (hCG) levels, specific gravity, pH levels, protein levels, ketone levels, bilirubin levels, nitrite levels, or leukocytes levels.

In some embodiments, the plurality of test strips is housed in a replaceable cartridge. Multiple replaceable cartridges are inserted side-by-side. The plurality of test strips is stacked vertically in the replaceable cartridge with an opening at the bottom of the stack. The first test strip is pushed onto a platform using a motor-operated pin. The platform is moved laterally, using the motor, to the predetermined position where the first test strip is exposed to the portion of the sample. The platform is moved laterally, using the motor, to a position where the image of the first test strip is captured by the sensor. The platform is moved laterally, using the motor, to a position where the first test strip is pushed off of the platform using a motor-operated pin into a waste bin to dispose of the first test strip.

In some embodiments, the sensor includes a complementary metal-oxide-semiconductor (CMOS) sensor and a light excitation source. The captured image of the first test strip includes a light intensity profile of the first test strip.

In some embodiments, the captured image includes a red-green-blue (RGB) picture of the first test strip. The computing device is configured to crop the RGB picture. The computing device is configured to convert the RGB picture to a hue-saturation-value (HSV) color space, hue-saturation-lightness (HSL) color space, YUV color space, or YCbCr color space.

In another aspect, the disclosure is directed to a method. The method includes collecting a urine sample from a patient in a collection component. The method also includes transporting a portion of the urine sample from the collection component to a predetermined position relative to the collection component using a fluid transportation system. Further, the method includes exposing, by the fluid transportation system, a first test strip to the portion of the urine sample. The first test strip is one of a plurality of test strips configured to indicate a condition of the patient when exposed to the sample. In addition, the method includes delivering, by the fluid transportation system, fresh water or another cleaning solution to the collection component to clean the collection component. Still further, the method includes positioning, by a motor, the first test strip near a sensor. Even further, the method includes capturing an image of the first test strip using the sensor. The image indicates the condition of the patient. Yet further, the method includes positioning, by the motor, a second test strip of the plurality of test strips at the predetermined position. Even still further, the method includes analyzing, by a computing device, the image of the first test strip in order to determine the condition of the patient.

In yet another aspect, the disclosure is directed to a replaceable cartridge. In some embodiments, the replaceable cartridge includes opposing reels. The replaceable cartridge also includes a plurality of test strips located on a belt that spans the opposing reels and configured to indicate a condition of a patient when exposed to a urine sample from the patient. The opposing reels are rotatable in order to move the belt and reposition the plurality of test strips. The test strips are spaced sufficiently far apart from one another on the belt such that a portion of the urine sample can be dispensed on one of the test strips without getting any of the urine sample on other test strips. In some embodiments, the replaceable cartridge can include stacks of test strips that are stacked vertically. The stack of test strips is housed in a cartridge with a slit at the bottom to pull out a test strip. In some embodiments, the replaceable cartridge can include a circular or elliptical carousel where test strips are rotated into the appropriate position.

Terms and expressions used throughout this disclosure are to be interpreted broadly. Terms are intended to be understood respective to the definitions provided by this specification. Technical dictionaries and common meanings understood within the applicable art are intended to supplement these definitions. In instances where no suitable definition can be determined from the specification or technical dictionaries, such terms should be understood according to their plain and common meaning. However, any definitions provided by the specification will govern above all other sources.

Various objects, features, aspects, and advantages described by this disclosure will become more apparent from the following detailed description, along with the accompanying drawings in which like numerals represent like components.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE FIGURES

FIG. 2B is an illustration of a sample collection component, according to an embodiment of this disclosure.

FIG. 3B is an illustration of a sample collection component, according to an embodiment of this disclosure.

FIG. 9B is an illustration of a sample volume control component, according to an embodiment of this disclosure.

FIG. 10C is a diagram of an anti-contamination film, according to an embodiment of this disclosure.

FIG. 10D is a diagram of an anti-contamination film, according to an embodiment of this disclosure.

FIG. 10E is a diagram of an anti-contamination film, according to an embodiment of this disclosure.

FIG. 10F is a diagram of an anti-contamination film, according to an embodiment of this disclosure.

FIG. 10G is a diagram of an anti-contamination film, according to an embodiment of this disclosure.

FIG. 10H is a diagram of an anti-contamination film, according to an embodiment of this disclosure.

DETAILED DESCRIPTION

Figure 1:
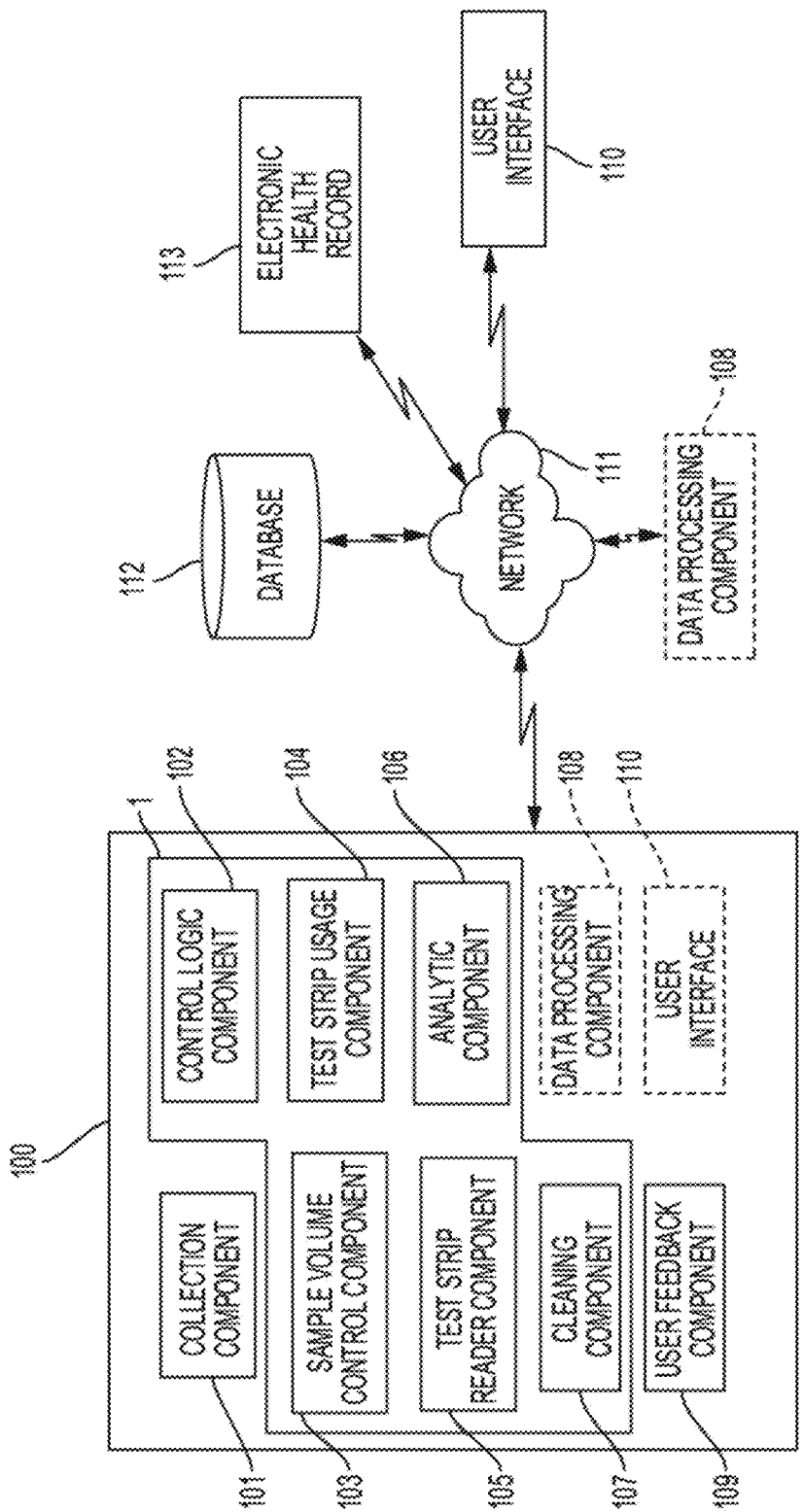
FIG. 1 is a block diagram view of an illustrative diagnostic system, according to an embodiment of this disclosure.
Figure 2A:
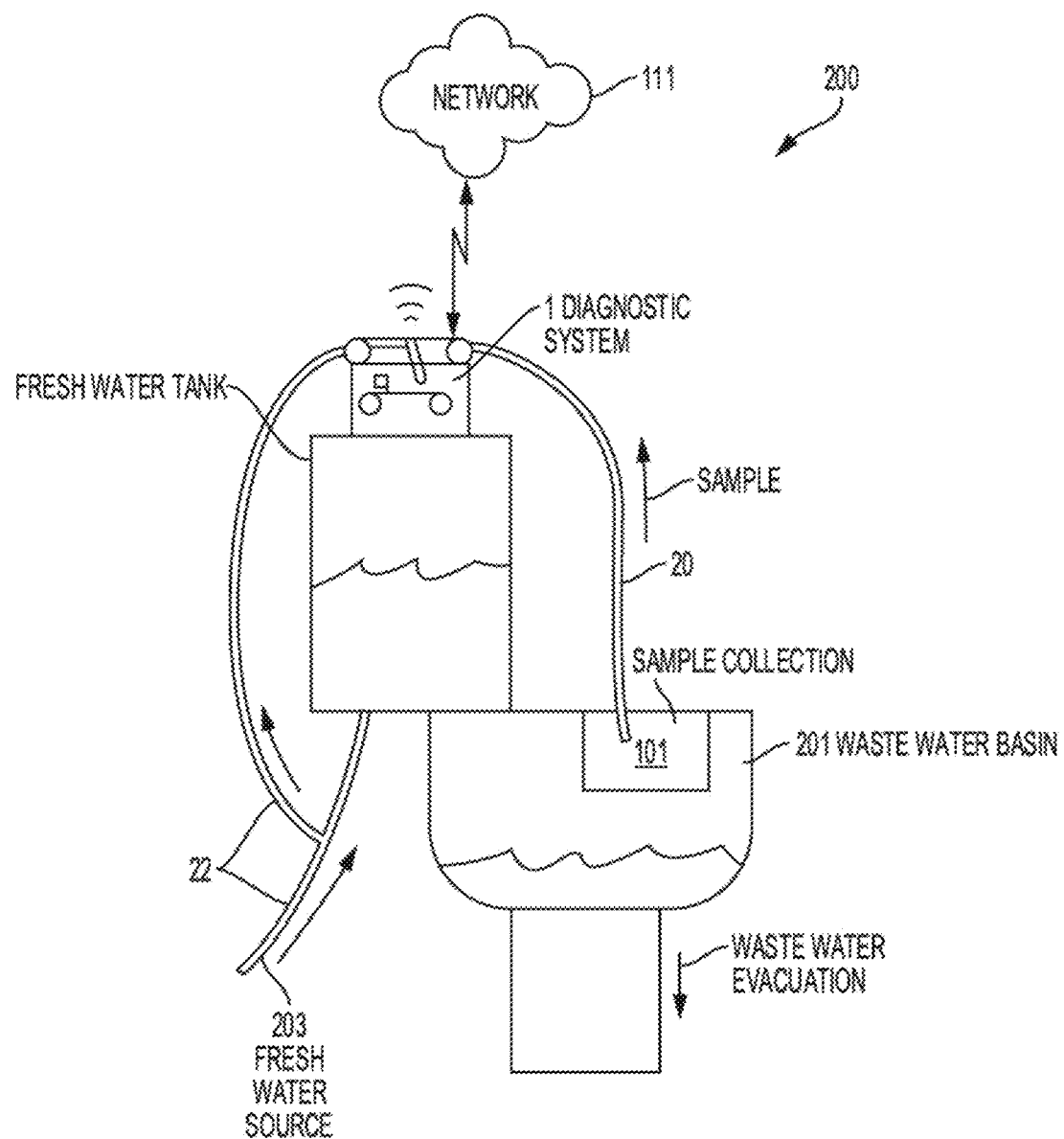
FIG. 2A is a side elevation view of an illustrative installation of the diagnostic system, according to an embodiment of this disclosure.

Example methods and systems are described herein. Any example embodiment or feature described herein is not necessarily to be construed as preferred or advantageous over other embodiments or features. The example embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the figures should not be viewed as limiting. It should be understood that other embodiments might include more or less of each element shown in a given figure. In addition, some of the illustrated elements may be combined or omitted. Similarly, an example embodiment may include elements that are not illustrated in the figures.

The following disclosure is provided to describe various embodiments of a medical diagnostic system. Skilled artisans will appreciate additional embodiments and uses of the present invention that extend beyond the examples of this disclosure. Terms included by any claim are to be interpreted as defined within this disclosure. Singular forms should be read to contemplate and disclose plural alternatives. Similarly, plural forms should be read to contemplate and disclose singular alternatives. Conjunctions should be read as inclusive except where stated otherwise.

Expressions such as "at least one of A, B, and C" should be read to permit any of A, B, or C singularly or in combination with the remaining elements. Additionally, such groups may include multiple instances of one or more element in that group, which may be included with other elements of the group. All numbers, measurements, and values are given as approximations unless expressly stated otherwise.

Various aspects of the present disclosure will now be described in detail, without limitation. In the following disclosure, a medical diagnostic system will be discussed. Those of skill in the art will appreciate alternative labeling of the medical diagnostic system as an automated sample analysis system, urinalysis system, pregnancy detection system, chronic kidney disease detection system, medical condition testing system, the invention, or other similar names. Similarly, those of skill in the art will appreciate alternative labeling of the medical diagnostic system as a sample collecting and testing method, automated sample testing and data communication method, automated urinalysis and biomarker detecting method, method, operation, the invention, or other similar names. Skilled readers should not view the inclusion of any alternative labels as limiting in any way.

Referring now to FIGS. 1-19, the medical diagnostic system 100 will now be discussed in more detail. The medical diagnostic system may include a sample collection component 101, sample volume control component 103, test strip usage component 104, test strip reader component 105, sample analytic component 106, data processing component 108, data communication component 109, networked data management component, device cleaning component 107, and additional components that will be discussed in greater detail below. The medical diagnostic system may operate one or more of these components interactively with other components for automating analysis of samples to predict a medical condition.

The sample collection component 101 will now be discussed in greater detail. FIGS. 1-4, 10A-12, and 14-16 highlight examples of the sample collection component, which may also be shown in other figures. The sample collection component may be used to collect a sample from a patient for analysis. In one example, the sample collection component 101 may include a collection cup 24 installable in or on a toilet 200 or other waste collection device. Skilled artisans will appreciate additional embodiments that do not require installation to a toilet after having the benefit of this disclosure. In one example of an alternative installation, the sample collection component 101 may include aspects to connect to a catheter and/or urine collection bag and receive the sample from the catheter and/or bag. This example including a catheter may be installable on a patient bed, examination table, benchtop, chair, or other location. In another example of an alternative installation, the sample collection component 101 may be installed in a room, urination booth, bedside toilet commode, raised toilet seat commode, or urination table. The sample collection component 101 may be removable. Additionally, in some embodiments, the sample collection component 101 may be modular, including replaceable and/or customizable parts. In embodiments where the sample collection is modular, it can be designed on any sized commercial toilet, for example, an elongated, standard, wide, or narrow toilet.

The sample collection component 101 may include a space at least partially enclosed by raised sidewalls. The space of the sample collection component 101 may be configured to receive and hold a liquid. A sample transmission medium, for example, a tube 20, may be operatively connected to the sample collection component 101 to transport at least part of a collected sample to other components of this disclosure. In the example including a tube, the tube 20 can be made of materials that will allow the fluid to pass through without sticking to the walls of the tube including silicone, polytetrafluoroethylene (PTFE/TEFLON®) or polyethylene. In the example including a tube, the tube 20 can be of any width or any length. One example of the tube width is ⅛" ID×³⁄₁₆" OD×¹⁄₃₂" Wall. One example of the tube length is 2 feet in length. In the example including a tube, the tube 20 connecting the sample collection cup 24 and the test strip reader component 105 can be installed connected to the toilet 200 where the tube goes underneath the toilet seat. In one example, the tube 20 may be at least partially inserted into the space partially enclosed by the sample collection component 101. In another example, the tube 20 may be installable to an aperture created on a surface of the sample collection component. In yet another example, multiple transmission media may be operatively connected to the sample collection component 101 to transport a sample to other components of this disclosure. The transmission medium can be configured to puncture a sample collection component from beneath or the side, or to flexibly bend into a sample collection component from above. In both instances, either the transmission medium or the sample collection component can be moving into each other, controlled by a motor(s) or system of motor(s) and/or gear(s).

In an embodiment where the collection component is installed into the toilet, the collection component may be activated and deactivated by a user input. The user input could be based on the barcode or RFID scanner 57 and the collection component can open after the barcode or RFID identifier is scanned. The collection component can be activated and deactivated using a motor. The collection component can be activated and deactivated using a folding mechanism that is attached to another part of the toilet. The collection component can be activated and deactivated using an air flow. The source of the air flow can be a motor in the device.

In an embodiment where the collection component is installed into the toilet, the material and shape of component will be described. The collection component can be made of hydrophobic material such as polypropylene, silicone, or anti-stick coatings such as polytetrafluoroethylene (PTFE/TEFLON®) or borosilicate glass. The collection component can have a rounded bottom on the interior of the component. The collection component can also have smooth sides, meaning that there are no indents or grooves within the component. Having smooth sides may minimize the amount of residual urine and biomolecules that stick on the wall.

Figure 3A:
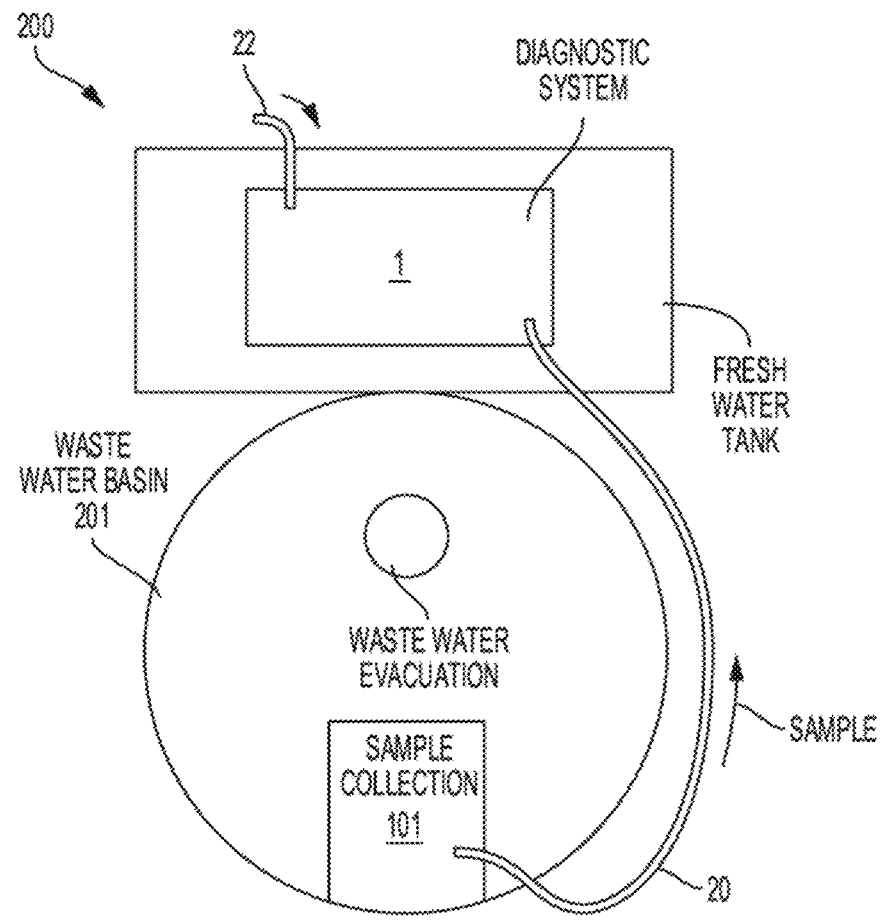
FIG. 3A is a top plan view of a sample collection component, according to an embodiment of this disclosure.
Figure 4:
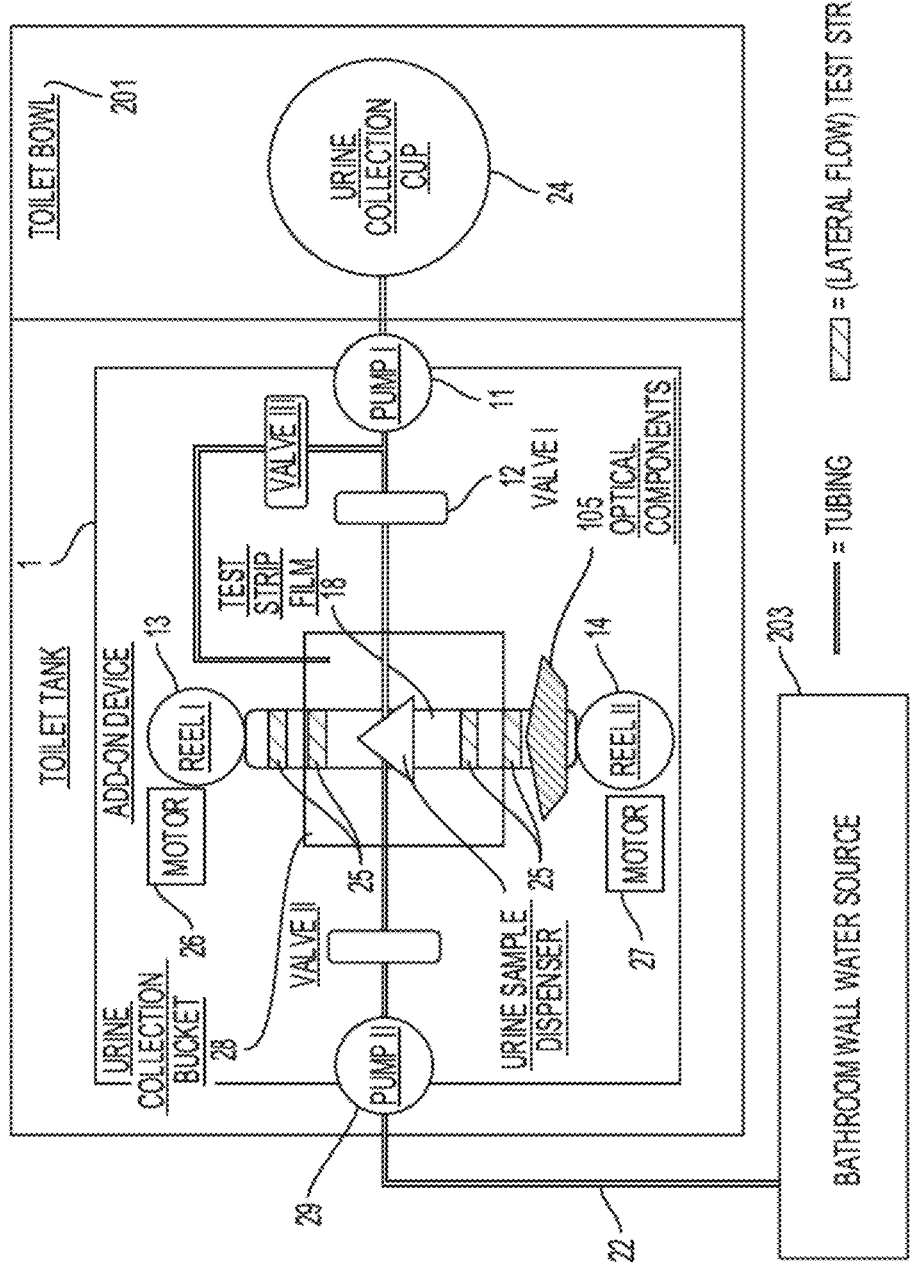
FIG. 4 is a block diagram view of a sample collection component operatively configured with additional components of the system, according to an embodiment of this disclosure.
Figures 5, 6, 7, 8, 9A:
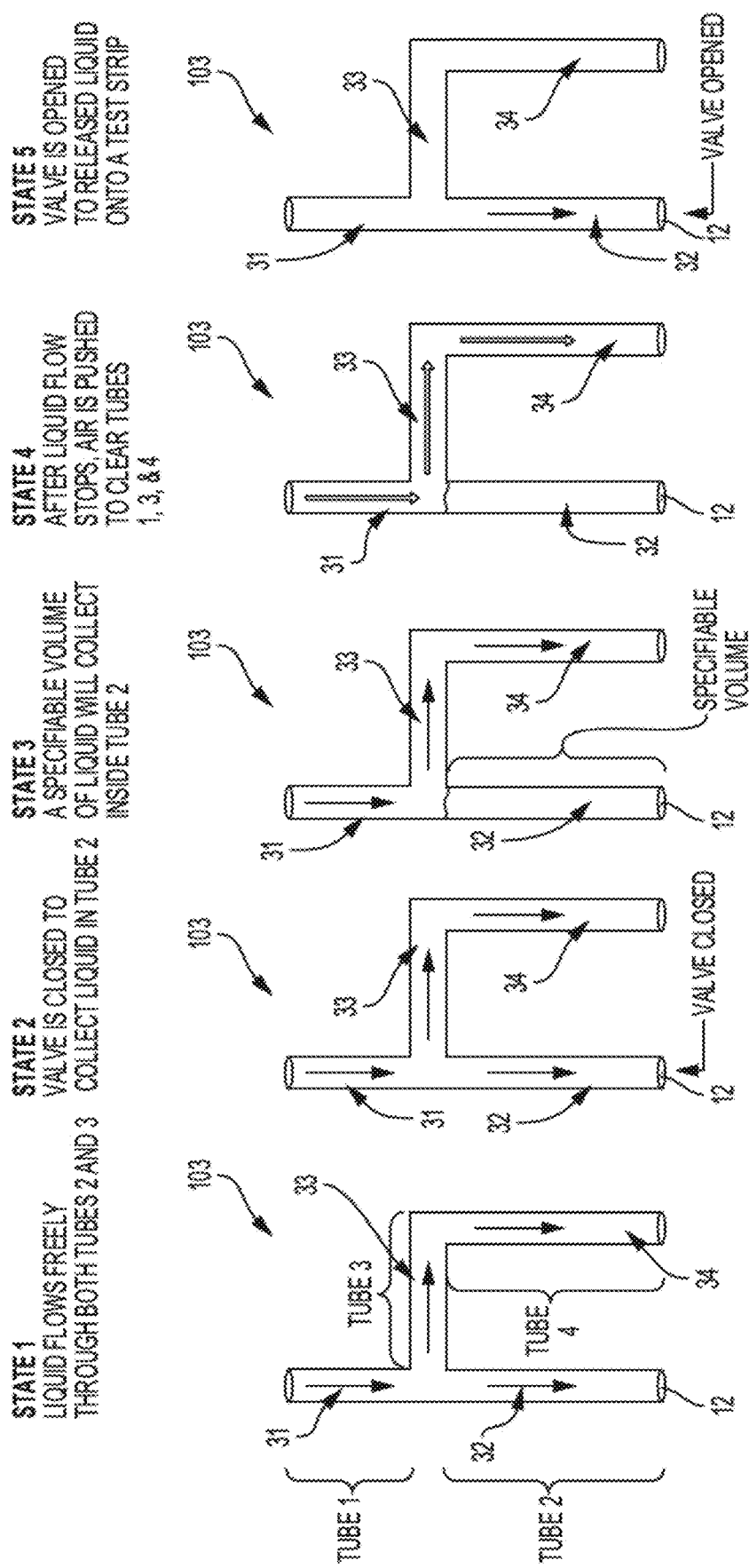
FIG. 5 is a side elevation view of a sample volume control component in an opened configuration, according to an embodiment of this disclosure.
FIG. 6 is a side elevation view of a sample volume control component in a collecting configuration to collect a sample, according to an embodiment of this disclosure.
FIG. 7 is a side elevation view of a sample volume control component in a collecting configuration with a collected sample, according to an embodiment of this disclosure.
FIG. 8 is a side elevation view of a sample control configuration in a sample isolation configuration, according to an embodiment of this disclosure.
FIG. 9A is a side elevation view of a sample volume control component in a sample delivery configuration, according to an embodiment of this disclosure.
Figure 10A:
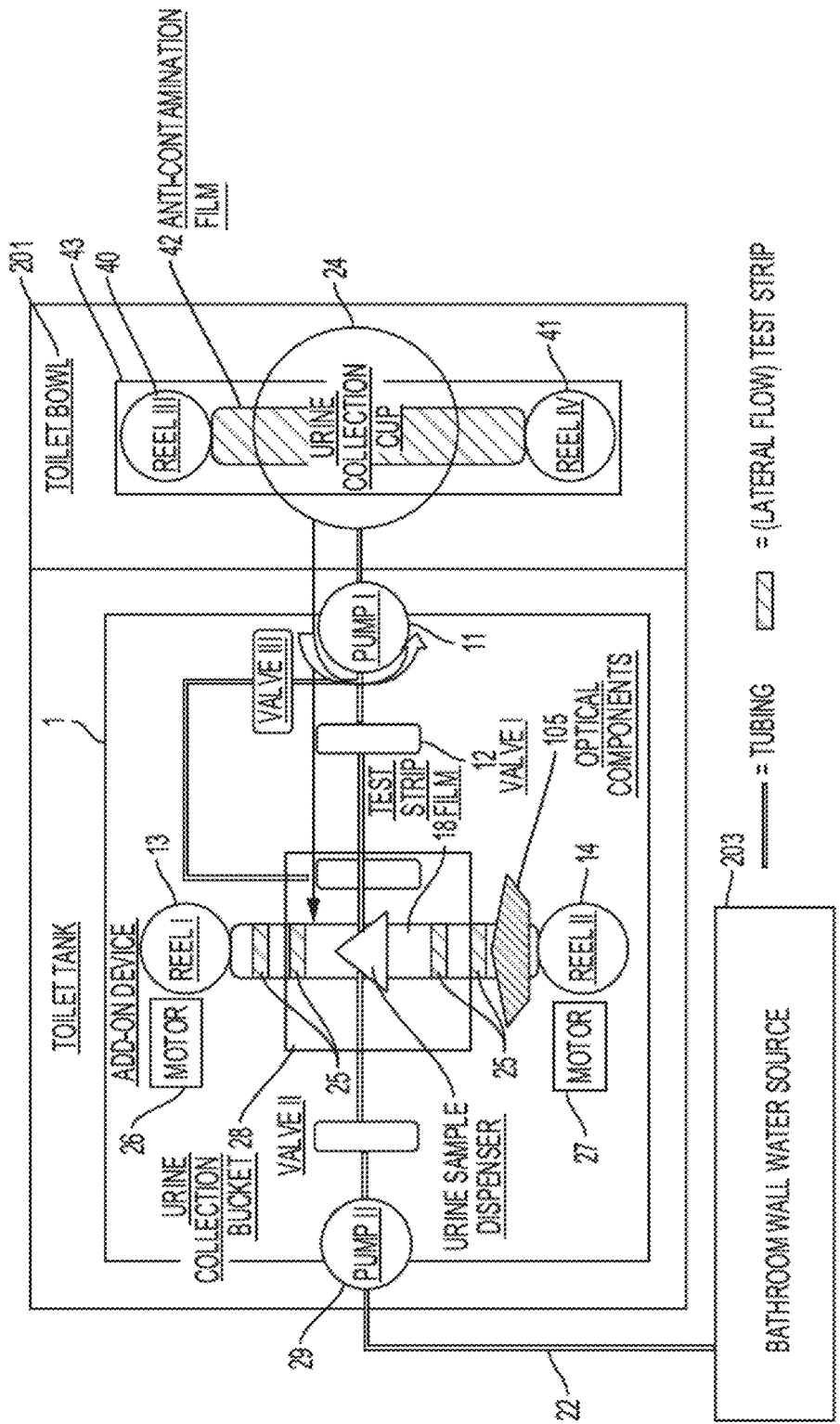
FIG. 10A is a block diagram view of a sample feeder preparing to receive a sample, according to an embodiment of this disclosure.
Figure 10B:
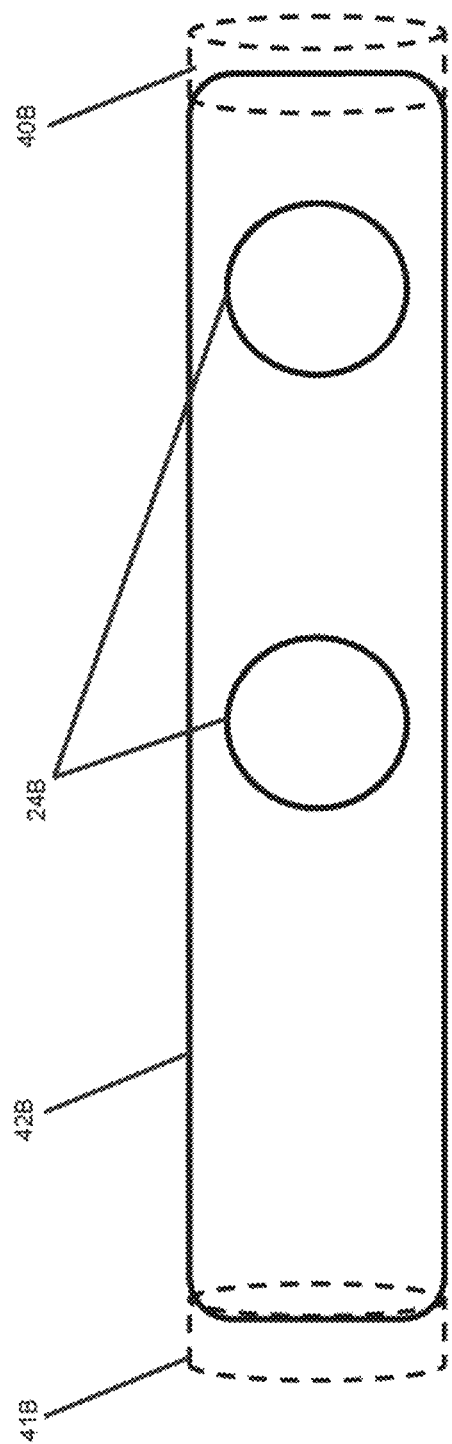
FIG. 10B is a diagram of an anti-contamination film, according to an embodiment of this disclosure.
Figure 11:
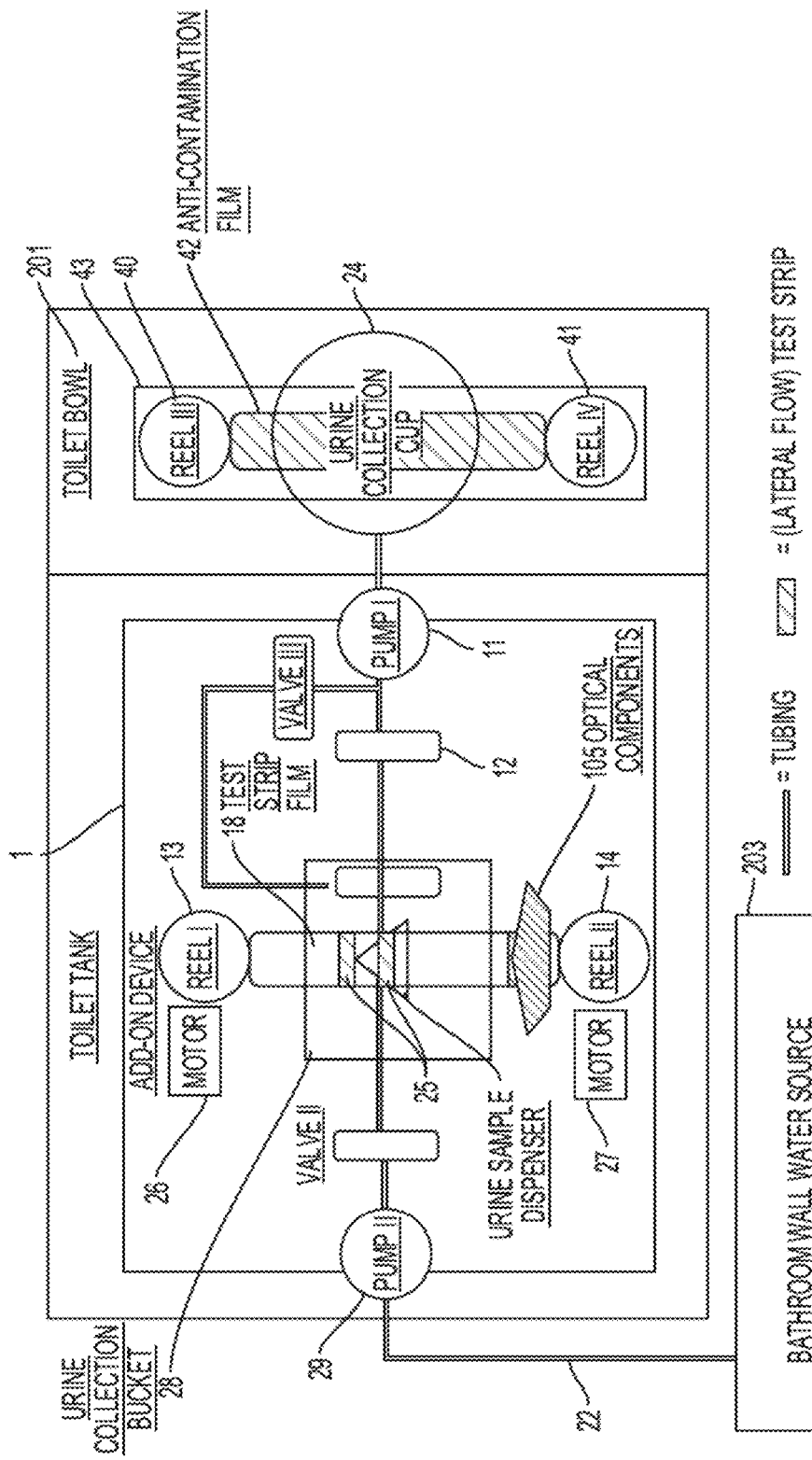
FIG. 11 is a block diagram view of a sample feeder positioning a sample about a sensor positioning a test strip beneath the sample volume control component, according to an embodiment of this disclosure.
Figure 12:
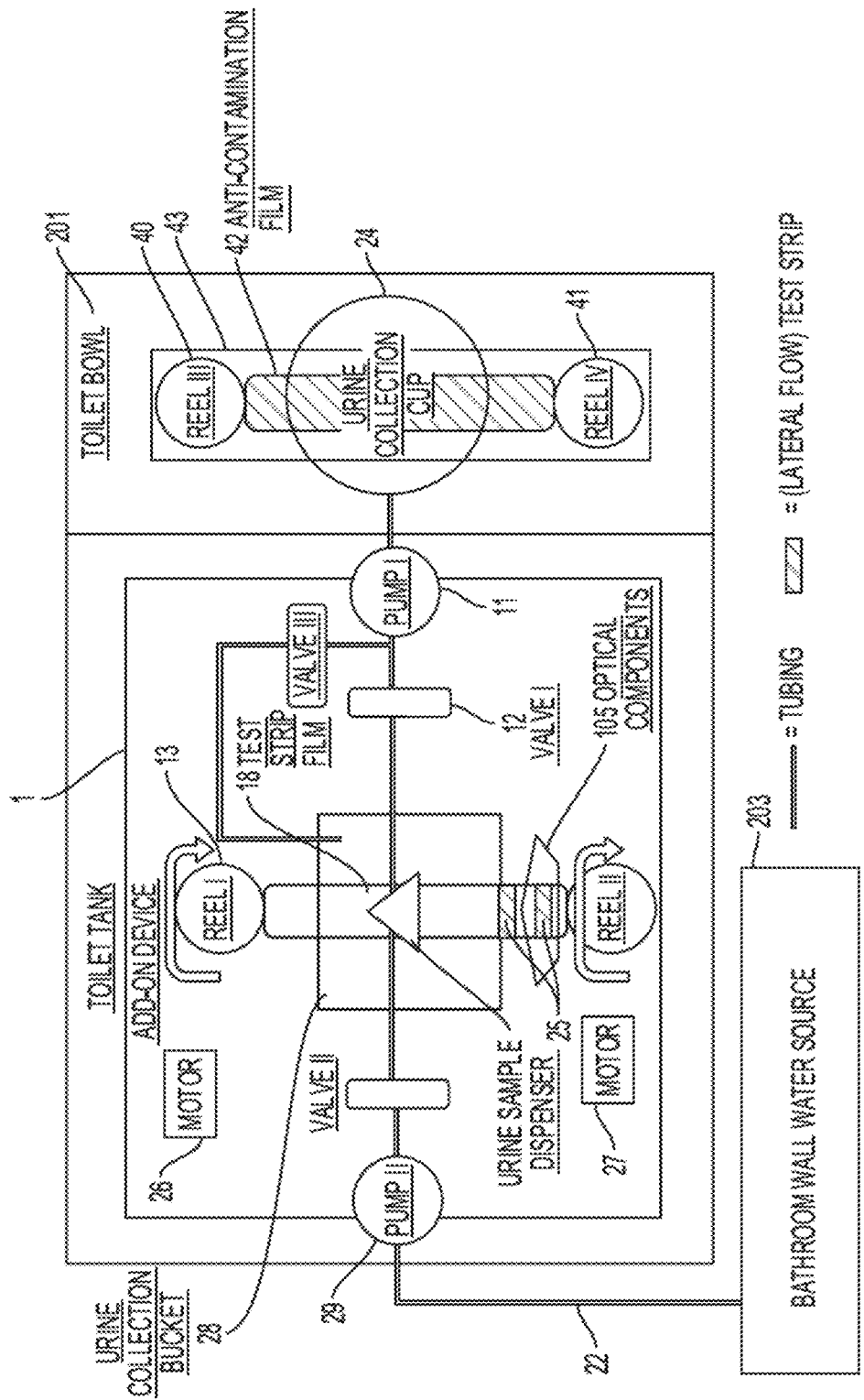
FIG. 12 is a block diagram view of a sample feed preparing to receive a subsequent sample after a test strip has been analyzed for a condition beneath the test strip reader component, according to an embodiment of this disclosure.

In FIGS. 2B, 3B, the sample collection component can be installed on a toilet lid 205 or toilet seat. The sample collection component can be activated when the toilet lid 205 or seat is brought downward by the user or by a motor or system of motor(s) and gear(s). The collection component can swing into place using, as an example, a four-bar linkage. The toilet lid can have a retractable cover that opens when the toilet lid swings down, thus activating the sample collection component, and closes when the toilet lid swings up, thus deactivating the collection component. The collection component 101 can be connected to a linear actuator 701. In the embodiment where the collection component is connected to a linear actuator 701, the collection component 101 can move linearly in the toilet to catch urine. In this embodiment, the collection component can consist of a platform 207 that contains a collection cup 206 where a bendable arm 208 connects the platform 207 to the linear actuator 701. In the embodiment where the collection component 101 is installed on a toilet lid 205, a second empty slot 209 can be added to the platform 207 to insert a collection cup to collect a sample for downstream laboratory testing in a sterile manner.

Optionally, a decontamination mechanism 43 may be included by the sample collection component 101 to reduce the likelihood of sample contamination. For example, an anti-contamination film 42 may be connected to opposing reels, such as reels III 40 and IV 41 shown by FIGS. 10A-12. In the example where an anti-contamination film 42 is used, the film can be made of polyester, polytetrafluoroethylene (PTFE/TEFLON®), polyethylene or polypropylene. As a sample is being produced by a patient, an unused portion of the anti-contamination film 42 may be positioned by the reels 40, 41 to at least partially prevent decontamination of the sample. Once the sample is done being produced by the patient, the reels 40,41 may rotate to move the anti-contamination film 42 away from the collection cup 24 or other sample collection component 101. As the reels 40, 41 continue to rotate, an additional unused area of the anti-contamination film 42 may be located between the collection cup 24 or other sample collection component 101 and a new patient. In another example, an ultraviolet light source may be mounted near the sample collection component, and ultraviolet light may be directed towards the sample collection component continuously or in selected time intervals in order to decontaminate the sample collection component.

The anti-contamination film 42 may be attached to two opposing reels (e.g., reels III 40 and IV 41) that are installed outside of the toilet bowl. The opposing reels can be mounted onto the toilet bowl or can be mounted on a platform on the floor near the toilet structure. The opposing reels may be operated by a single motor, two motors, or more than two motors, with or without a system of gear(s). Such motor(s) may be different than the motors use to operate the test strip reel(s). The anti-contamination film 42 can either be placed within a permanently installed sample collection mechanism or can serve as the collection mechanism itself.

In some embodiments (e.g., embodiments where the anti-contamination film 42 is placed within a permanently installed sample collection mechanism), the opposing reels may rotate in a fresh "sheet" of the anti-contamination film 42 onto the mechanism. The patient may then urinate into the mechanism. At the bottom of the mechanism, there may be a tube or other connection to transport the urine to the testing device. Upon flushing, the anti-contamination film 42 may be rotated out of the collection mechanism where it can either be detached or rotated into a waste collection unit attached to or installed next to the toilet.

In some embodiments (e.g., embodiments where the anti-contamination film 42 serves as the collection mechanism), the anti-contamination film 42B may have a disposable collection mechanism 24B with pockets that expands when the patient urinates into the device. The film is rotated using reels 40B, 41B. The pockets in the film of mechanism 24B may start out compressed and, as the weight of urine is applied on the pockets in the film of the mechanism, the pockets in the film of mechanism may expand to collect the urine. The anti-contamination film 42B may be rotated and then linearly or partially linearly translated and moved to the edge of the toilet where there may be a tube with a sharp object 45B designed to open and collect the urine from the disposable mechanism. There may be tubing 45C that goes into the mechanism 24B from the top through flexible bending. Upon flushing, the anti-contamination film 42B may rotate out of the toilet and into a waste collection unit attached to or installed next to the toilet.

In FIGS. 10A-12, one embodiment of the decontamination mechanism 43, provided as a non-limiting example, an entire or substantial portion of the surface area of the anti-contamination film 42 may be reused through rotation and linear translation of usable portions of the anti-contamination film 42. For a patient, an unused portion of the anti-contamination film 42 may be located above or adjacent to the collection cup 24. The patient may urinate onto this unused portion of the anti-contamination film 42 to provide a sample. After the urine of the patient's sample has been analyzed, an unused portion of film 42 may be used for collection of the next sample. The used portion of anti-contamination film 42 may be washed with a cleaning fluid. In the example where the used portion of film is washed with cleaning fluid, the cleaning fluid can be bleach, a bleach solution diluted with water, water with soap, citric acid, water with surfactant(s) (such as sodium dodecyl sulfate), ethanol, methanol, disinfectants, or water. The washed portion of film may then be rotated into a drying area, which may include a sponge, air blower, ventilation area, and/or other drying aspect. When the washed portion of the film has dried, it may be rotated back onto the collection cup 24 as an unused portion of the film for a future patient to urinate on. Drying a cleaned portion of film may substantially prevent stray cleaning fluid from being stuck on the film, which could dilute the urine sample and decrease accuracy of a diagnostic result.

The sample collection component 101 may include a device for evacuating at least part of the remaining sample after a desired amount of sample has been transported to the other components of this disclosure. For example, the sample collection component 101 may include a valve or adjustable aperture to release collected samples. In the example where a flow-adjustment valve is used, the valve can be a solenoid pinch valve or a plug valve. Alternatively, the sample collection component 101 may be at least partially rotatable to dump excess samples into the toilet or other waste collection device. Skilled artisans will appreciate additional examples of evacuating excess sample from the sample collection after having the benefit of this disclosure.

In one embodiment, a cleaning component may be operatively connected to the sample collection component 101. By connecting to the sample collection component, the cleaning fluid can be drawn into the device and tubing inside of the device to flush out the remaining fluid. For example, a tube or other transmission medium may deliver fresh water or another cleaning solution to the sample collection component. This fresh water or other cleaning solution may substantially clean the sample collection component 101 and related components between each sample collected. The fresh water or cleaning solution may also be transmitted through the additional tubes or other connected components, such as the sample volume control component 103 discussed below, to increase the efficacy of a cleaning operation. In the example where another cleaning solution is used, the cleaning solution can be bleach, a bleach solution diluted with water, water with soap, citric acid, water with surfactant(s), ethanol, methanol, disinfectants, or water. By including a cleaning component, the components provided by this disclosure may advantageously decrease cross-patient contamination of collected samples, thus decreasing the likelihood of inaccurate results.

The sample volume control component 103 will now be discussed in greater detail. FIGS. 1, 4-12, 14, and 16 highlight examples of the sample volume control component 103, which may also be shown in other figures. The sample volume control component 103 may collect, dispense, and optionally measure a desired volume of the sample from sample collection component 101. A housing may hold the sample volume control mechanism above the test strip film.

The sample volume control component 103 may include one or more pumps 11, tubing 31, 32, 33, 34, valves 12, and other aspects that would be appreciated by a person of skill in the art after having the benefit of this disclosure. The tubing 31, 32, 33, 34 may be made of various materials, including hydrophobic material to minimize and substantially prevent fluid from sticking to a surface of the tubing. Examples of hydrophobic tubing materials may include, but are not limited to, polypropylene, silicone, and anti-stick coatings such as polytetrafluoroethylene (PTFE/TEFLON®). The pumps can be peristaltic pumps. The various aspects of the sample volume control component 103 may be operated by digital logic, a computerized device, manual switches and instructions, or otherwise. For example, aspects of this disclosure may be at least partially controlled via a microprocessor, FPGA, ARDUINO®, RASPBERRY PI®, specialized processor, emulation, or electronic component. Instructions may be included in memory, provided via a ROM, or otherwise provided to the electronic components.

In FIGS. 4, 10A-12, the sample volume control component 103 may include a pump 11 to draw a sample from the sample collection component 101, for example, to draw patient urine from a collection cup 24. The sample may be transmitted through a tube 20 or other transmission medium to a sample volume control component 103. The sample volume control component 103 may include an array of tubes 31, 32, 33, 34 and valves 12 to collect and measure a received sample. For example as illustrated in FIGS. 5-9A, and without limitation, the sample control device may include four tubes—first tube 31, second tube 32, third tube 33, and fourth tube 34.

A volume of sample may be received by the tubes 31, 32, 33, 34 of the sample volume control component 103 from the sample collection component 101. In this example, the sample may be passed through an entrance end of first tube 31 of the volume control component 103. At the exit end of first tube 31, the sample may be separated into two paths associated with the entrance ends of second tube 32 and third tube 33, respectively. A three-way solenoid pinch valve 12 may be located around the exit ends of second tube 32 and third tube 33, which has two pinch valves that may be alternated between opened and closed states. When the pinch valve around second tube 32 is set to a closed state, the valve may substantially block the exit end of second tube 32, causing sample to collect between the entrance and exit ends of second tube 32. In this scenario, the pinch valve around third tube 33 is set to the opened state. When second tube 32 is substantially full of sample, the remaining sample passing through first tube 31 will continue through third tube 33 and fourth tube 34, exiting through the exit end of fourth tube 34 until the remaining sample is depleted. The sample passing through the exit end of fourth tube 34 may be collected by a waste basin, such as a urine collection bucket 17 in FIGS. 4, 10A-12, rerouted to the toilet 200 or other waste collection device, or otherwise routed.

In FIGS. 5-9A, second tube 32 may be sized to hold a desired volume of fluid. Skilled artisans will appreciate wherein other tubes or mechanism are used to collect sample for testing, those mechanisms may also be configured respective to the desired volume of the sample to be collected. While the valve 12 of second tube 32 is configured in a substantially closed state, any collected sample may be held within second tube 32. When it is desired to release the sample to a test strip, the valve 12 of second tube 32 may be opened to allow the fluid to pass through the exit end of second tube 32.

Skilled artisans will appreciate additional embodiments of the sample volume control component 103 that may include more tubes than the example provided above. For example, a sample volume control component 103 may include additional tubes with valves located at the exit end. These additional tubes may collect additional volumes of sample that can be released to test strips. The inclusion of multiple collection tubes may advantageously facilitate retesting, testing for multiple conditions, or other testing scenarios that would benefit from additional sample collection.

In FIG. 9B, the sample volume control component can also be constructed with multiple tubes 31B, 32B, 33B, a wye- or y-connector 35B, and a three-way solenoid pinch valve (or pinch valve) 12B. In this embodiment, the tube 31B connected to the sample collection component will connect to a y-connector 35B. The y-connector 35B will connect this tube 31B to two other tubes 32B, 33B. One testing tube 32B is designated as the testing tube, and another tube is designated as the waste tube 33B.

In the embodiment where the sample volume control component has a y-connector, the movement of fluid and the process in which fluid is controlled will be described. The default state of the pinch valve 12B will be such that the testing tube 32B is closed and the waste tube 33B is open. When the sample is drawn from the sample collection component 101, the sample will first go through the waste tube 33B, and this process can take between 5 and 15 seconds. The sample may first go through the waste tube in order to flush out residual urine, water, or cleaning fluid from the tube 31B connected to the sample component 101 and the waste tube 33B. Then the three-way pinch valve 12B may then switch states and close the waste tube 33B while opening the testing tube 32B. The sample may then go through the testing tube to flush out any residual urine, water, or cleaning fluid to prevent contamination and dilution of the test result. Then the three-way pinch valve 12B will switch states again and close the test tube 32B while opening the waste tube 33B until the remaining sample fluid in the collection component 101 is depleted through the waste tube 33B, which fills the testing tube 32B partially or completely with sample fluid. This process can take between 2 and 10 seconds or between 5 and 20 seconds, in various embodiments. Then a test strip will be positioned under the testing tube 32B, and by rapidly or slowly opening and closing the pinch valve 12B around the testing tube 32B, with the pump 11 in between the sample collection component 101 and testing tube 32B continuously running, the sample will be dropped onto a test strip as droplets at a controlled rate to prevent oversaturating a test strip. Alternatively, after a test strip is positioned under the testing tube 32B, the pinch valve 12B around the testing tube 32B can be configured to the open state, and the pump 11 in between the sample collection component 101 and testing tube 32B can be toggled on and off slowly or rapidly. In this scenario, the sample will be dropped onto a test strip from the testing tube 32B as droplets at a controlled rate to prevent oversaturating a test strip. After a test strip is exposed to the sample, the test strip will be positioned to the sensor for analysis.

The test strip usage component 104 will now be discussed in greater detail. The test strip usage component 104 may alternatively be referred to as a test strip feeder component, automated test strip usage component, automated test strip feeder component, or other labels which will be apparent to a person of skill in the art after having the benefit of this disclosure. FIGS. 1-2A, 4, 10A-12, 14-15, and 17 highlight examples of the test strip usage component 104, which may also be shown in other figures. The test strip usage component 104 may be substantially automated. The test strip usage component may include reels 13, 14, a belt, and test strips 25 located on a film 18 on the belt. In one embodiment, the belt may be constructed using a film 18. The reels may be rotated by a motor 26, 27, such as a stepper motor, DC motor, AC motor, servo motor, or other motor that would be appreciated by a person of skill in the art. One or more motors 26, 27 may be operated to move the belt, film 18, or other material spanning between the reels 13, 14. The test strip usage component may include a waste collection component, which will collect excess sample that will be connected to a tube that connects to the sample collection component.

The film would be a nonstick, hydrophobic film. One example of a material for the film would be a high-temperance polyester film. The film should also have a high tensile strength. One example of a possible range of the tensile strength is between 5000 and 10000 psi. The film may not be too thick, in some embodiments. One example of the thickness of the film would be 0.001 inches to 0.003 inches in thickness.

The test strips 25 may include various chemicals, biomolecules, and substances that may bind to and/or react to a sample. The reaction of the test strip may indicate a condition. Different types of tests may be performed via the test strips, which could be operated using the components of this disclosure. For example, test strips including tests based on aptamer, antibody, and/or chemical reagents may be used, without limitation. Test strips with chemical reagents may use a colorimetric method. Aptamer and antibody test strips may use a colorimetric, fluorescent, or other approach. For aptamer and antibody, additional types of assays, such as lateral flow sandwich or competitive, may additionally be used, without limitation.

The film 18 and test strips 25 may be included in an enclosure. For example, the film and test strips may be located in a replaceable cartridge, which may be an enclosure that is inserted into the device to be at least partially received by the automated test strip usage reels. The cartridge may resemble an audio cassette, video cassette recorder (VCR) cassette, or other reel-to-reel cartridge device that would be apparent to a person of skill in the art. Multiple test strips, for example 100+ test strips, may be included by a cartridge. Skilled artisans will appreciate alternative numbers of test strips includable by a cartridge, which is intended to be within the scope of this disclosure. The cartridge may be replaceable, such as once enough included test strips have been used, providing new test strips for use with additional samples. Alternatively, the cartridge including one or more test trips exposed to one or more samples may be removed and sent to a laboratory for additional testing.

Cartridges may include different test strips, which may work with different sensors of the reader. For example, a first illustrative cartridge may be configured with test strips to detect beta-trace protein, which can be used to detect chronic kidney disease (CKD). A second illustrative cartridge may include test strips to detect glucose, which can be used to indicate a risk of diabetes. A third illustrative cartridge may include test strips to screen for opiates such as 6-MAM, codeine, dihydrocodeine, hydrocodone, norhydrocodone, hydromorphone, oxycodone, noroxycodone, oxymorphone, noroxymorphone, naloxone, or morphine, which may help ensure proper medical care for patients entering an emergency department, urgent care facility, or other location. A fourth illustrative example may include a cartridge with test strips to detect human chorionic gonadotropin (hCG), beta-hCG, beta-core hCG, beta-fragment hCG, and/or free beta-hCG, one or more of which may be indicative of pregnancy. Detection of such indicators may reduce the likelihood of pregnant women being provided treatments that could harm an embryo or fetus in gestation. A fifth illustrative example may include a cartridge with test strips for different conditions arranged in series or in parallel to detect different conditions, allowing a patient to be tested and/or screened for multiple conditions from the collected sample. A sixth illustrative example may include a cartridge with test strips to detect biomarkers such as glucose, bilirubin, ketone, specific gravity, blood, pH, protein, urobilinogen, nitrite, and leukocyte esterase for general urinalysis. A seventh illustrative example may include a cartridge with test strips to detect substances such as, but not limited to, amphetamines, methamphetamines, barbiturates, cannabinoids for drug/substance abuse testing. Skilled artisans will appreciate additional examples within the scope and spirit of this disclosure, after having the benefit of this disclosure.

In one example, the components and operations of this disclosure may beneficially substantially automate the urine dilution process to check for a hook effect. If a woman has progressed sufficiently in her pregnancy, her urine will likely have a high concentration of beta-core hCG and/or beta-fragment hCG, which may oversaturate the antibodies in the sandwich lateral flow assay urine pregnancy test strips. As a result, a false negative result can occur. In the event of a negative result, the components and operations of this disclosure may use the leftover urine and automatically dilute the urine with water. This may lower the concentration of beta-core hCG and/or beta-fragment hCG. This diluted urine may be released onto a second test strip. Since the beta-core hCG and/or betafragment hCG concentration of the diluted urine is lower, the second test strip will give a true positive signal if the woman is indeed pregnant.

The components and operation of this disclosure may use an aptamer and/or antibody sandwich assay lateral flow test strip that may target beta-fragment hCG and/or beta-core hCG to prevent the hook effect. Additionally, the components and operation of this disclosure may test a urinary hCG:creatinine ratio to take account for the effects of urine dilution, which can lead to false negatives. The testing provided by this disclosure may use creatinine to normalize hCG for natural urine dilution in the human body. Alternatively, the reader may run a quantitative or semi-quantitative analysis instead of a qualitative (yes/no) urinary hCG pregnancy test to reduce the risk of false negatives.

Figure 17:
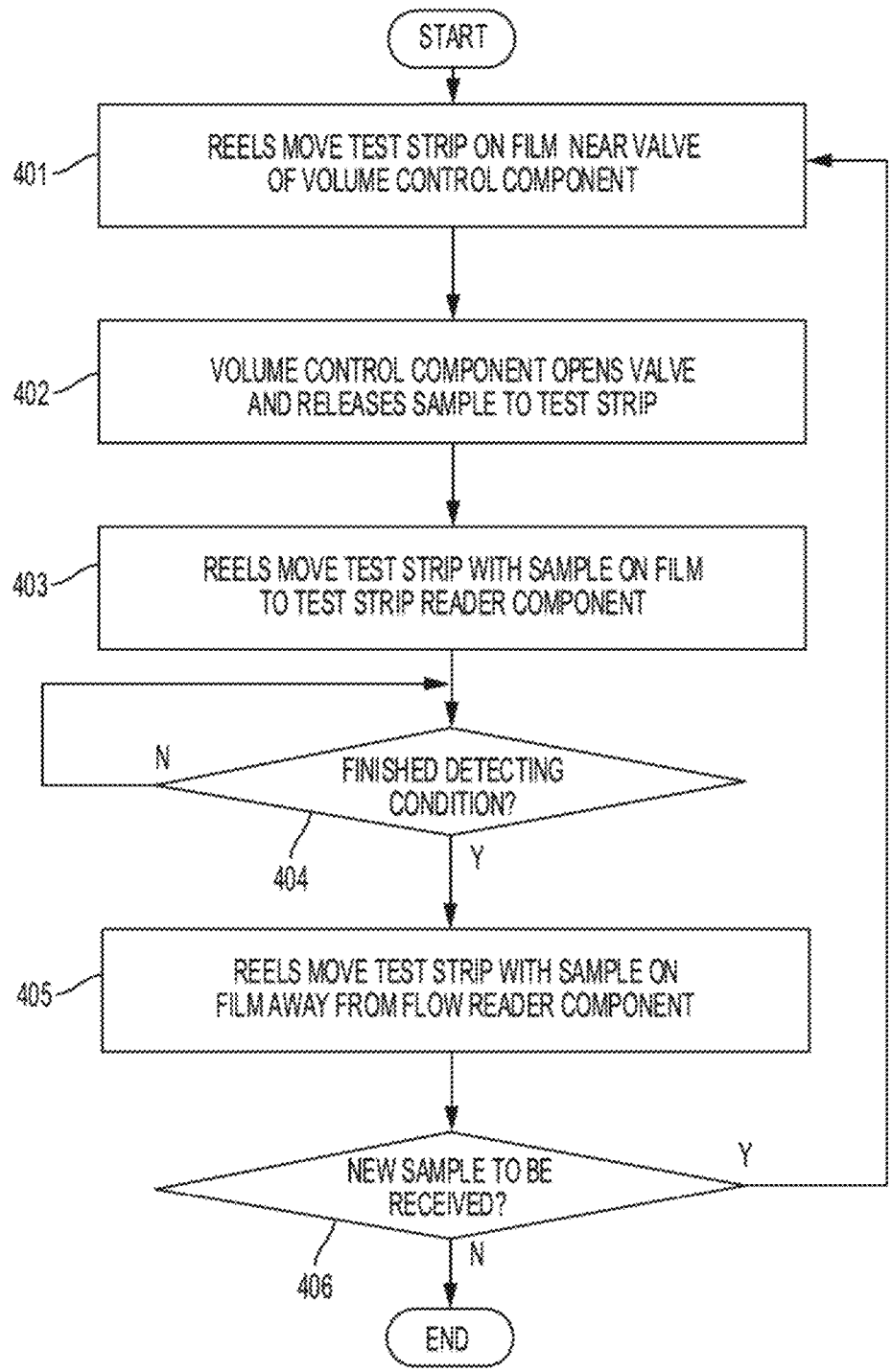
FIG. 17 is a flow chart view of a sample delivery and detection operation, according to an embodiment of this disclosure.

As illustrated in the workflow in FIG. 17, the test strip usage component 104 may rotate the reels 13, 14 to position a test strip 25 located on the film 18 to desired locations, as would be needed for each step of the sample collecting and testing operation. For example as described in block 401, the reels 13, 14 may be rotated to locate a test strip 25 below a valve 12 of the sample volume control component 103 to receive a sample. The reels 13, 14 then may be further rotated to locate the test strip 25 underneath a test strip reader component 105. The operation of the test strip usage component as illustrated in FIG. 17 will be discussed in greater detail below. The reels 13, 14 may be rotated up to a point determined by an outside stimulus. Examples of this stimulus include a "latch", a reflective opto-interrupter, a camera, a light sensor, and others.

Cartridges will be able to go through multiple test strips. Each test strip on the cartridge will be sufficiently far apart such that the sample can be dispensed on one test strip without getting any of the sample on other test strips. Additionally, the distance between each test strip is variably spaced apart to allow each test strip to be rolled around both reel in the cartridge without undesired overlap and stacking. In some embodiments, this distance may be 100 to 150 millimeters.

A raised platen may be added to the device. When the cartridge is inserted into the device, the test strip film may be laid on top of the platen, which may increase the surface tension of the film and raise the film above the reels. The platen removes any potential sagging of the film during the diagnostic procedure when the film is moving. After the cartridge is inserted, the film will be on the platen, and the reels of the cartridge will roll the film across the platen during a diagnostic procedure. The platen may have rounded edges, which will allow the film to roll easily across the platen.

Optointerrupters can be mounted onto the housing of the sample volume control mechanism 103 and/or the test strip reader component 105. There can be two optointerrupters to be used to position a test strip. The first optointerrupter will position a test strip underneath the testing tube 32, 32B of the sample volume control component 103 so that the test strip can be exposed to the sample. The second optointerrupter will position a test strip underneath the test strip reader component 105 so that a test strip exposed to the sample can be imaged by the test strip reader component. The optointerrupters project an electromagnetic signal and a reflective component of the test strip reflects a signal back to the optointerrupter receiver, and the system will stop the reels from rolling the test strip film when the optointerrupter receives this signal.

The test strips in the cartridge can be modified. In the embodiment where optointerrupters are used, the test strips can be modified to be reflective by placing a red, white, silver, or other reflective color adhesive film on the test strip. In the embodiment where optointerrupters are used, the test strips can be modified to be reflective by layering on a reflective surface onto the test strip such as, but not limited to, aluminum foil or white opaque material.

Figure 28:
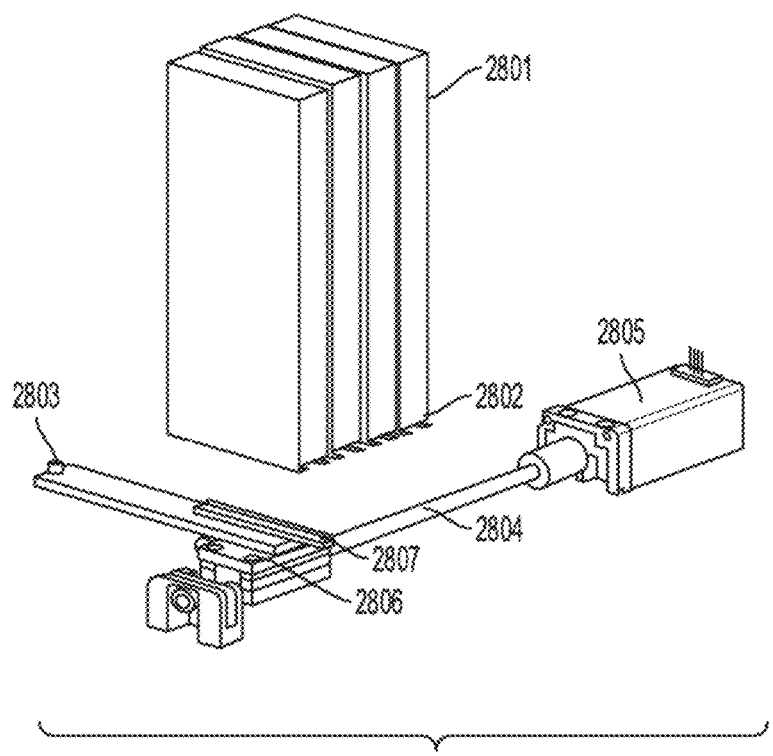
FIG. 28 is an illustration of a replaceable cartridge and test strip transportation system, according to an embodiment of this disclosure.

In FIG. 28, another embodiment of the test strip usage component is illustrated. Test strips can be stacked vertically into a cartridge 2801, with a test strip stacked on top of another test strips. There can be multiple vertical cartridges inserted side-by-side at any time. The cartridge 2801 can contain multiple test strips (for example, 100 strips). The cartridge 2801 can have dimensions of 0.5"×2"×6". The cartridges will be humidity controlled using, as an example, vacuum sealing. To release the test strips into the device, there will be an opening 2802 at the bottom of the cartridge 2801. The test strips can be pushed to the bottom of the stack using a constant-force spring or weight that is on the top of the cartridge 2801. There can be a door or an opening at the bottom of the cartridge which can allow for the removal of one strip. In the embodiment with a door, the door can automatically close after the strip is mounted. The test strip carrying mechanism will be laterally moved underneath the cartridge 2801 to get the test strip. The test strip can be pushed on a platform 2806 using a pin 2803. The pin 2803 can be driven by a motor. There can be more than one platform to carry more than one test strip. The platform 2806 can move laterally towards the sample volume control component 103 and the test strip reader component 105. The lateral movement is driven by a motor 2805 using a linear stage 2804. After reading, the platform 2806 can be moved laterally to a waste receptacle and the test strip can be pushed by the pin into a waste receptacle.

In the embodiment where the test strips are stacked vertically in a cartridge 2801, a molded plastic housing 2807 with the test strip adhesive can hold the test strip. The strip plus housing 2807 can be 1.5 mm thick. The test strip housing 2807 can interlock, which would allow for gravity to push the strips and housing 2807 downward while also keeping them from catching against the sides of the cartridge 2801.

In another embodiment, the test strip usage component can have test strips aligned in a carousel. In this embodiment, the test strips are set in a circle and there is a rotation mechanism to rotate the test strip to a position to expose it to the sample and to a later position to analyze the test result.

The test strip reader component 105 will now be discussed in greater detail. FIGS. 1, 2, 4, 10A-12, 14, and 17-19 highlight examples of the reader 105, which may also be shown in other figures. The test strip reader component 105 may include a sensor to detect a condition respective to a test strip located near the sensor. Housing will hold the test strip reader component about the test strip film. The housing for the test strip reader component can be the same as the housing for the sample volume control component 103. In one embodiment, the test strip reader component may include multiple sensors capable of detecting multiple conditions. Additionally, a single sensor includable by the test strip reader component 105 may optionally be configured to detect multiple conditions. The sensors of the test strip reader component 105 may be replaceable, substitutable, and/or swappable. In an alternative embodiment, the sensors of the test strip reader component 105 may be substantially permanently installed. In some embodiments, the test strip reader component 105 may include a lateral flow test strip reader for colorimetric or fluorescent lateral flow test strips.

The test strip reader component 105, for example, a lateral flow test strip reader, may conduct diagnostic operations on the sample to detect a condition. For example, the test strip reader component 105 may detect biomarkers from a test strip 25 exposed to a sample, which may indicate the presence of a condition. In one embodiment, the test strip reader component 105 may include a CMOS sensor and a white or color light excitation source to image a light intensity profile related to a test strip and sample. For example, a sensor of the flow reader may detect an orange, green, or otherwise colored light emitted by the test strip, which may indicate the presence of a related condition.

The test strip reader may use an image processing algorithm in order to determine the presence of a condition. In one embodiment, the sensor takes a picture of the test strip, the image is cropped and converted to greyscale, morphological operations are performed to remove noise, the gradient of the image is taken, the peak(s) are identified, and the result is printed to be used by the emergency health record. In another embodiment, the sensor takes a picture of the test strip, the image is cropped and may be converted from RGB color space to other color spaces such as HSV, HSL, YUV, and YCbCr. The color spaces may be broken into individual channels, such as Saturation and Hue in the HSV color space. Within each channel, the cumulative sums of rows are taken to form a single dimensional array. The peak(s) are identified and cross-checked across other channels in same or different color spaces, and the result is printed to be used by the emergency health record.

Additional test strips may be used with corresponding sensors, which may include and test for alternative biomarkers. Examples of alternative biomarkers may include DNA, short DNA sequences, amino acids, proteins, carbohydrates, RNA, cells, aptamers, pH, acidity, chemical concentrations, fluorescent materials, phosphorescent materials, antibodies, metabolites, other biomolecules, and/or other detectable substances that would be apparent to those of skill in the art after having the benefit of this disclosure. For example, provided without intent to limit available biomarkers to the open set of this example, some biomarkers may include leukocytes, nitrates, urobilinogen, proteins, pH, blood, specific gravity, ketones, bilirubin, and/or glucose.

The detected condition may be collected as data. For example, the test strip reader component may output a digital value representing biomarkers detected from the test strip. The digital output may be a qualitative, semi-quantitative, or quantitative result. In an example with a qualitative result, the digital value may be, for example, a "yes" or "no" or "1" or "0". The value of "yes" or "no" will depend on the type of test strip. In one example, a FirstResponse (trademarked) test strip, a single line will show up within 3 minutes if the urine sample tests negative for human chorionic gonadotropin (hCG) and two lines will show up within 3 minutes if the urine sample tests positive for hCG. The sensitivity and specificity of these tests are specified by the manufacturer. In an example with a semi-quantitative result, the digital value may be a range of biomarker concentration and an associated descriptor of the range that the specific test result biomarker concentration corresponds with. In an example with a quantitative result, the digital value may be a specific or definable biomarker concentration. A biomarker concentration may take the form of various units, such as mg/dL. In an additional example, an aptamer-based, antibody-based, or RNA-based test strip may emit a light with a characteristic wavelength upon detection of a condition. The sensor may detect any emitted light and report the detected wavelengths in the data.

Figure 25:
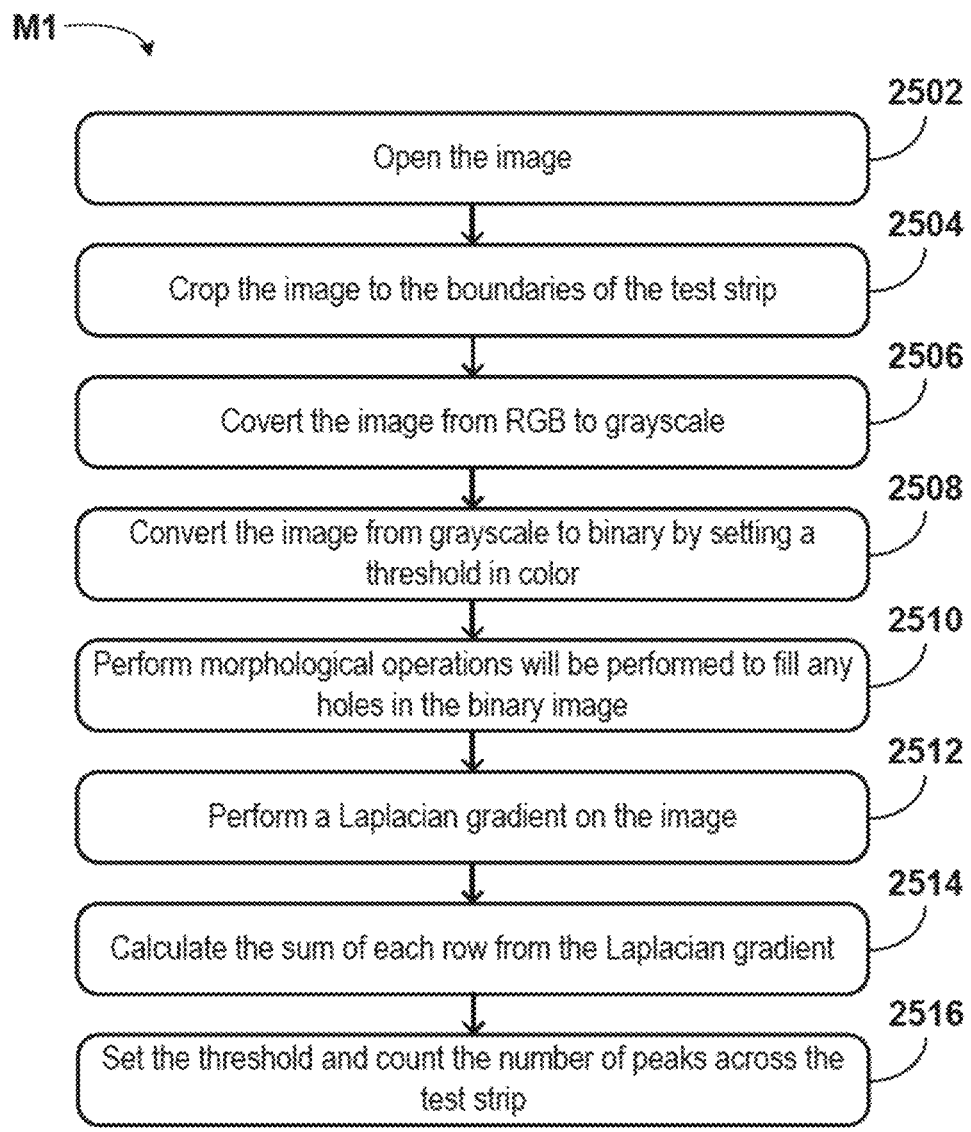
FIG. 25 is a flow chart view of a method, according to an embodiment of this disclosure.
Figure 26:
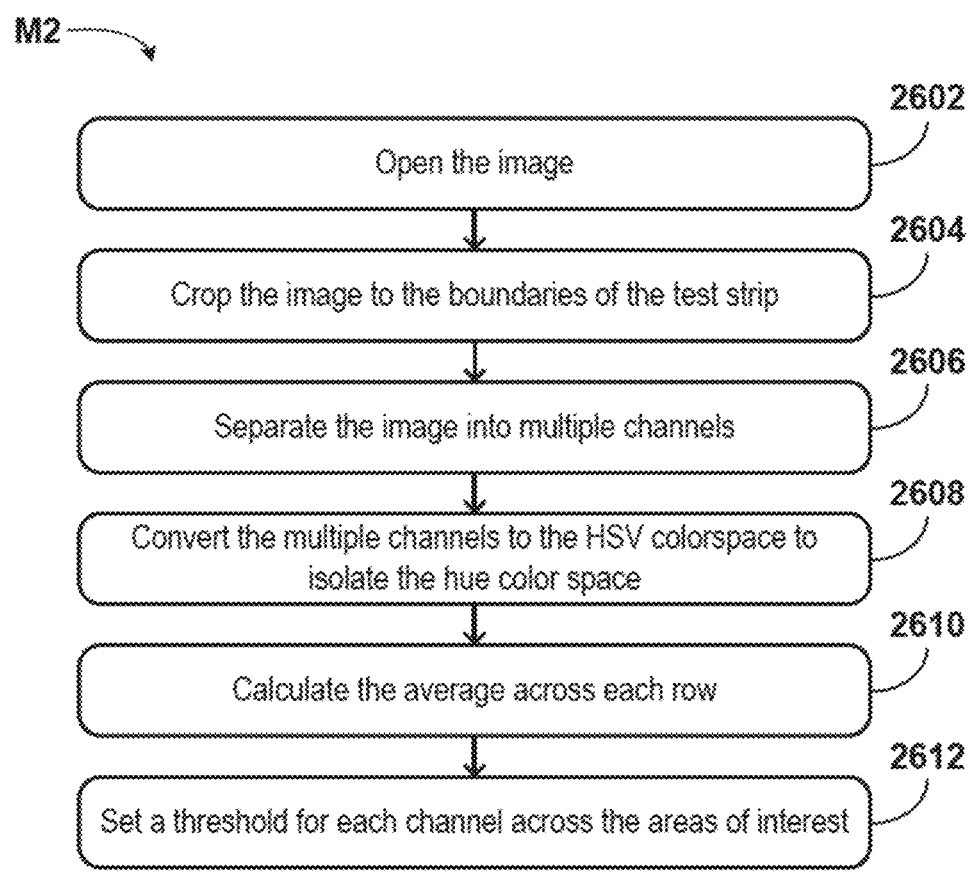
FIG. 26 is a flow chart view of a method, according to an embodiment of this disclosure.

The image processing algorithm, which is covered in FIGS. 25 and 26, is described in this section. The image processing algorithm will take the image 601 on the test strip with the sample and convert the image into a result, for example, a "yes" or "no" to identify the existence of a condition such as pregnancy.

One possible algorithm M1 is illustrated in FIG. 25 and detailed as follows. The algorithm can be used for test strips such as FirstResponse where the test strip reports a control line only for a negative result and a control line and a result line for a positive result. At block 2502, M1 starts by opening the image 601. At block 2504, the image 601 will be cropped to the boundaries of the test strip 25. At block 2506, the image 601 with then be converted from RGB to gray scale. At block 2508, the image 601 will then be converted from grayscale to binary by setting a threshold in color. At block 2510, morphological operations will be performed to fill any holes in the binary image. The morphological operation can include defining a kernel size such as a 5 pixel by 5 pixel square, performing an open operation with the kernel, and performing a close operation with the kernel. At block 2512, a Laplacian gradient on the image 601 will be performed. The Laplacian gradient will result in a series of rows. At block 2514, M1 may include calculating the sum of each row. At block 2516, M1 may include setting the threshold and counting the number of peaks across the test strip.

If there are no peaks or more than two peaks, there is an error with the test strip or the image, so report ERROR. If there is only one peak in the areas of interest, this indicates that only the control line is detected, so report NEGATIVE. If there are two peaks in the area of interest, then both the control line and the result line are detected, so report POSITIVE.

One possible algorithm M2 is detailed as follows. The algorithm can be used for test strips such as FirstResponse where the test strip reports a control line only for a negative result and a control line and a result line for a positive result. At block 2602, M2 starts by opening the image 601. At block 2604, the test strip boundaries in the image 601 are identified using an algorithm. The algorithm may include the following. The image may first be converted from RGB into grayscale. The average pixel value of each column is determined. Then, the peak column value is identified. This peak corresponds to the test strip average pixel value. The left and right sides of the test strip are identified by using a threshold and reading left and right from the peak until the column value crosses threshold. The image 601 is cropped to the boundaries of the test strip 25. At block 2606, the image 601 is separated into multiple channels. In the RGB colorspace, the red, green, and blue channels are isolated. The image with the red, green, and blue channels may be isolated to create monochrome images. At block 2608, the channels are also converted to the HSV colorspace to isolate the hue color space. Each channel will result in an image. Filtering, such as low-pass filters or high-pass filters, may be applied to reduce the noise or increase the signal in the image. Thresholding, such as simple threshold or adaptive Gaussian threshold, may be applied to this image to reduce noise further. At block 2610, the average pixel value is calculated across each row for each channel. The control line location is identified by calculating the maxima or the minima in the average pixel values. The result line location is identified by moving a set number of pixels from the control line location. At block 2612, thresholds for each channel will be set across these areas of interest.

In another embodiment, the area under the curve for the control line and the result line are calculated. The thresholds for each channel will be set based on these areas. If the values exceed the thresholds for both the control line and the result line areas, report as POSITIVE. If the values do not exceed the thresholds, report as NEGATIVE.

The sample analytic component 106 will now be discussed in greater detail. FIGS. 1-2A, 4, 10A-12, 14, and 17-19 highlight examples of the sample analytic component, which may also be shown in other figures. The data produced by the test strip usage component 104 may be at least partially analyzed by the analytic component. For example, the sample analytic component 106 may correlate the data produced by the test strip usage component 104 to a symptom or other evidence of a medical abnormality. The data, which may be received from the test strip reader component 105 and/or analyzed by the analytic component 106, may be shared with a data processing component 108. In one embodiment, the data processing component 108 may be connected via a network 111. In an additional embodiment, the data processing component 108 may be operated using a distributed processing platform, such as via the cloud.

The data processing component 108 will now be discussed in greater detail. FIGS. 1-2A, 13, and 18-19 highlight examples of the data processing component 108, which may also be shown in other figures. The data processing component 108 may include additional computerized processing components 58 to perform analysis on detected data. The data processing component may be connected to the other components of this disclosure via a network 111, such as the Internet. In instances wherein the data was initially analyzed by the sample analytic component 106, the data processing component 108 may perform an additional analysis of the data to analyze and interpret data about the condition.

In one embodiment, at least part of the data detected and/or analyzed during operation may be communicated with an electronic health record 113. For example, data and results from analysis of the data may be communicated to a collection of patient information on an electronically-stored medium. The electronic health record 113 may include additional data relating to a patient, some of which may have been communicated to the electronic health record 113 from other medical professionals and/or procedures. Analysis detected from the sample received by the patient may be compared to data present in the electronic health record 113 to detect a likelihood of a health risk or to perform other advanced calculations. This additional data may include, but should not be limited to, demographics, medication allergies, immunizations received, medical history, prior laboratory tests and corresponding results, vital signs, radiology charts, age, weight, body mass index (BMI), blood tests, and other medical information. The electronic health record 113 may additionally include health insurance policy, billing details, and other information related to the administration of medical services.

In this embodiment, the data will be transferred using an encrypted methodology that is in compliance with Health Insurance Portability and Accountability Act (HIPAA). Compliance with HIPAA is critical to be used when connecting to an electronic health record. Examples of encryption techniques that are covered can include AES 256-bit encryption, SHA-256 hashing, etc. In order to maintain this encryption standards, the data processing component may be patched using a wired or wireless connection, with data that is transmitted using Secure Socket Layers (SSL), Transport Layer Security (TLS), or the latest industry standards.

The data processing component 108 may additionally organize the data and processing results into a user accessible format. For example, the data processing component 108 may host a user interface 110 to share collected and/or derived data from the sample analysis. Additional data from the electronic health record 113 may additionally be shared with a patient via the user interface 110. The user interface 110 may allow physicians, patients, and other selected parties to view the data and results of a previously performed test. By leveraging available processing power and a substantially automated process, the data processing component 108 and other components of this disclosure may advantageously process a sample and provide results in a relatively short period of time.

The data processing component 108 can also save interaction level data. For the patient interaction, outside of storing the result of the test, the data processing component can save the length of the interaction, the specific tests that were performed, whether additional urine was needed for downstream testing, device and/or cartridge failures, and/or user errors. For clinical staff interaction, the data processing component can save the length of the interaction, the activity type (such as test cartridge replacement, device maintenance, or quality control), device and/or cartridge failures, and/or user errors. Metadata such as the unique device identifier, unique cartridge identifier, unique customer identifier, unique user identifier, date, and time can also be saved.

The data stored through the data processing component can be used as the foundation for different software platforms. One example software platform would be as a CLIA Quality Assurance system as it can meet at least five standards of quality assurance: patient test management, quality control, relation of results to clinical data, personnel, and records. Another example software platform would be as an inventory management system, in particular for the test strip cassette, including a predictive inventory management system or a reactive inventory management system. Another example software platform would be as a lifecycle management system, in particular for the device, including a predictive lifecycle management system or a reactive lifecycle management system.

One example of the CLIA quality assurance system is illustrated. For patient test management, the system can monitor and evaluate in real time the following procedures that use the device using predefined criteria: specimen collection, labeling, preservation and transportation, use of appropriate criteria for specimen rejection, test report completeness, timely reporting of results, accuracy and reliability of test reporting systems, and storage and retrieval of results.

One example of a predictive inventory management system is illustrated in the clinical setting. The system will analyze the average usage rate of test strips inside the cartridges for a clinical setting and compare the number of test strips used against the number of cartridges ordered by a site multiplied by the number of test strips within a cartridge. Based on the results of this comparison, the system will determine whether any activity needs to occur. As an example, if the number of test strips used exceeds a threshold relative to the number of test strip cartridges ordered times number of test strips within a cartridge and the average usage rate of test strips indicates that the site will run out of test strips in a set period of time (for example, 14 days), then the system could be automatically place an order for the clinical site to replenish the supply of test strip cartridges or notify the clinical site via the software platform that the test strip cartridges need to be replenished.

One example of a reactive lifecycle management system is illustrated. The device is made of multiple components. Each component can send a signal to the lifecycle management system, which will track the components' signals over time. Based on signals, different activities could occur. As an example, if the signal indicates that one of the components is defective, a maintenance team can be sent to the clinical site to fix the defective component.

One example of a reactive lifecycle management system is illustrated. There can be multiple devices in the field sending signals to a database or a group of databases which tracks the signals coming from all devices over time, the trends of the signals over all devices, the trends of the signals over time, and the trends of the signals over the amount of usage. Examples of amount of usage can be the number of test strips used, time usage based on total interaction time, number of times that a device has been activated or used, number of times that a component within the device has been activated or used, number of cartridges used, number of patient interactions, number of clinical staff interactions, etc. Based on the trends, different activities could occur. One example is to track the lifecycle of individual components of the device. If there is a trend of a specific component failing over a number of devices in the field, then it can be extrapolated that the lifecycle for that specific component for devices in the field is a given period of time identified based on these results. In this example where the lifecycle of a specific component is determined to be a given period of time, the vendor will be able to track the specific component in other devices in the field which are approaching the given period of time and the vendor will be notified which devices have a specific component reaching the end of the lifecycle based on the given period of time.

The data processing component can also analyze the data using machine learning algorithms and/or predictive analytics. An illustrative example can be seen with pregnancy testing in an OB/GYN office. The interaction time that nursing staff has with the device can be tracked. If certain nursing staff groups have longer interaction times than other nursing staff groups, then nursing staff leaders can be notified to schedule additional training for the other nursing staff groups.

Another illustrative example can be seen with a company that has multiple correctional facilities or rehabilitation centers. At each correctional facility or rehabilitation center, admitted people can be randomly drug screened, and a positive or negative result can be saved. If it is observed that the positive rate for drug screening is statistically significantly higher at one facility compared to the average positive rate at the other facilities, security measures or substance abuse programs can be put in place at the facility with the higher positive rate for drug screening.

Another illustrative example can be seen with emergency departments. Urine tests, one or many, can be ordered at any given emergency department. If it is observed that more urine tests are ordered at certain times of day or that more urine tests are ordered at certain emergency departments, additional human resources can be allocated to those times of day or those emergency departments with more urine tests ordered.

Another illustrative example can be seen with clinical studies. Currently, it can be difficult to perform certain studies that require a large population size because it is difficult and costly to perform decentralized studies. Multiple devices can be installed in multiple locations but communicate with a central database. Pharmaceutical and medical device companies can perform studies where levels of urine analytes are measured using the device. Qualified patients from the multiple locations can urinate into the device and the results of the test can be communicated to a central database. This solution allows for a decentralized clinical trial that can reach a larger and more diverse population at a lower cost.

Another illustrative example can be seen with linkages to digital health datasets. External data, such as demographic data, genomic data, and consumer wearables data, when mapped to patient-level urine diagnostic data can be used to understand the efficacy of a drug or medical device for specific populations. This information can be used to improve patient targeting for existing products and support the development for new products that address the needs of underserved populations.

Another illustrative example would be as a predictive tool for the progression of biomarker concentration over time for a specific patient. The progression over time of the biomarker concentration of an individual patient can be monitored continuously from the home. Because multiple devices can be installed in multiple at-home locations for different patients, the progression over time of the biomarker concentration can be monitored for multiple patients. Machine learning algorithms can be used to analyze the progression over time of the biomarker concentration of all patients and determine predictions for how the biomarker concentration would progress for a specific patient. When this method is coupled with longitudinal treatment data for patients, the longitudinal biomarker progression for a given patient can be predicted in response to a particular treatment or combination of treatments, including drug, device, and/or digital therapeutic, across a variety of treatment time cadences and paradigms. Furthermore, the longitudinal biomarker progression for a given patient can be predicted more accurately by comparing the specific inputs for a particular patient to the same inputs to aggregate patients, including genomic data, behavioral data, socioeconomic data, gender, age, occupation, consumer spending data, etc.

With the methods described above, treatment paradigms can be determined using machine learning to minimize the longtudinal biomarker progression for a given patient over time to minimize disease progression or to increase the concentration to be within a range of biomarker concentration, or to target a specific increase in biomarker concentration.

The machine learning algorithms used can be of a variety of different types. For example, regression algorithms such as ordinary least squares regression (OLSR), linear regression, logistic regression, stepwise regression, multivariate adaptive regression splines (MARS), or locally estimated scatterplot smoothing (LOESS) can be used. Artificial neural network algorithms such as perceptron, back-propagation, Hopfield network, or radial basis function network (RBFN) can be used. Deep learning algorithms such as deep Boltzmann machine (DBM), deep belief networks (DBN), convolution neural network (CNN), or stacked auto-encoders can be used. Clustering such as k-Means clustering, k-Medians clustering, expectation maximization (EM), and hierarchal clustering can be used.

A user interface 110 provided by the data processing component 108 may be accessible via a consumer electronic device, such as a computer 115, smartphone 114, or other device that would be appreciated by those of skill in the art. At least some aspects of the user interface 110 may additionally be provided by a display or electronic components included by a local installation of an illustrative diagnostic system. For example, the components of this disclosure may be communicably connected to a display and input device, such as buttons, mice, touchscreens, and other input devices, which may be located near the point of sample collection. Physicians and patients may interact with the user interface 110 via these devices during a sample collection appointment. In some embodiments, the components of this disclosure may also be calibrated using the user interface.

The data processing component 108 may additionally include, or be communicatively connected to, a database 112. For example, collected and/or derived data from sample testing may be stored by a database 112. This stored database 112 may be accessible and translated into user-readable information for display via the user interface. This stored database 112 can be based on a variety of platforms including, but not limited to, text file, Microsoft Excel, Microsoft SQL, Oracle RDBMS, SAP Sybase, MySQL, SQLite, MongoDB. The data may also be stored to compare multiple tests for a detectable condition to track progression of a disease over time. For example, a patient with a chronic disease, such as chronic kidney disease, can track trends of kidney function and potentially predict a need for upcoming changes in treatment. The data may also be stored to aggregate non-identifying data to track health population trends in a given population.

The device cleaning component 107 will now be discussed in greater detail. FIGS. 1-2 highlight examples of the device cleaning component 107, which may also be shown in other figures. The device cleaning component 107 may include fluid transmission media, such as tubes 22, and other aspects to substantially dilute and/or decontaminate the components from biomolecules and/or bacteria from different people of this disclosure between sample collection and analysis instances. For example, the device cleaning component 107 may include a connection to a water source 203 to source fresh water to the sample collection component 101, sample volume control component 103, and/or additional components of this disclosure. Skilled artisans will appreciate cleaning fluids other than fresh water may be used, without limitation, buffer solutions such as phosphate buffer solutions, alcohol (such as ethanol or methanol), disinfectants, antimicrobial solutions, bleach solutions, surfactants (such as sodium dodecyl sulfate), and other cleaning solutions that would be apparent to a person of skill in the art.

The device cleaning component 107 may wash the tubing or transmission media and the sample collection component 101 after each sample collection and analysis cycle, for example, with water drawn from the water source 203. At selective intervals, the tubing or transmission media may be wished with a wash buffer, for example, as may be used to wash laboratory flow cytometers in which blood samples from different people can touch the same flow path. The wash buffer may include a phosphate buffer solution.

Figure 27:
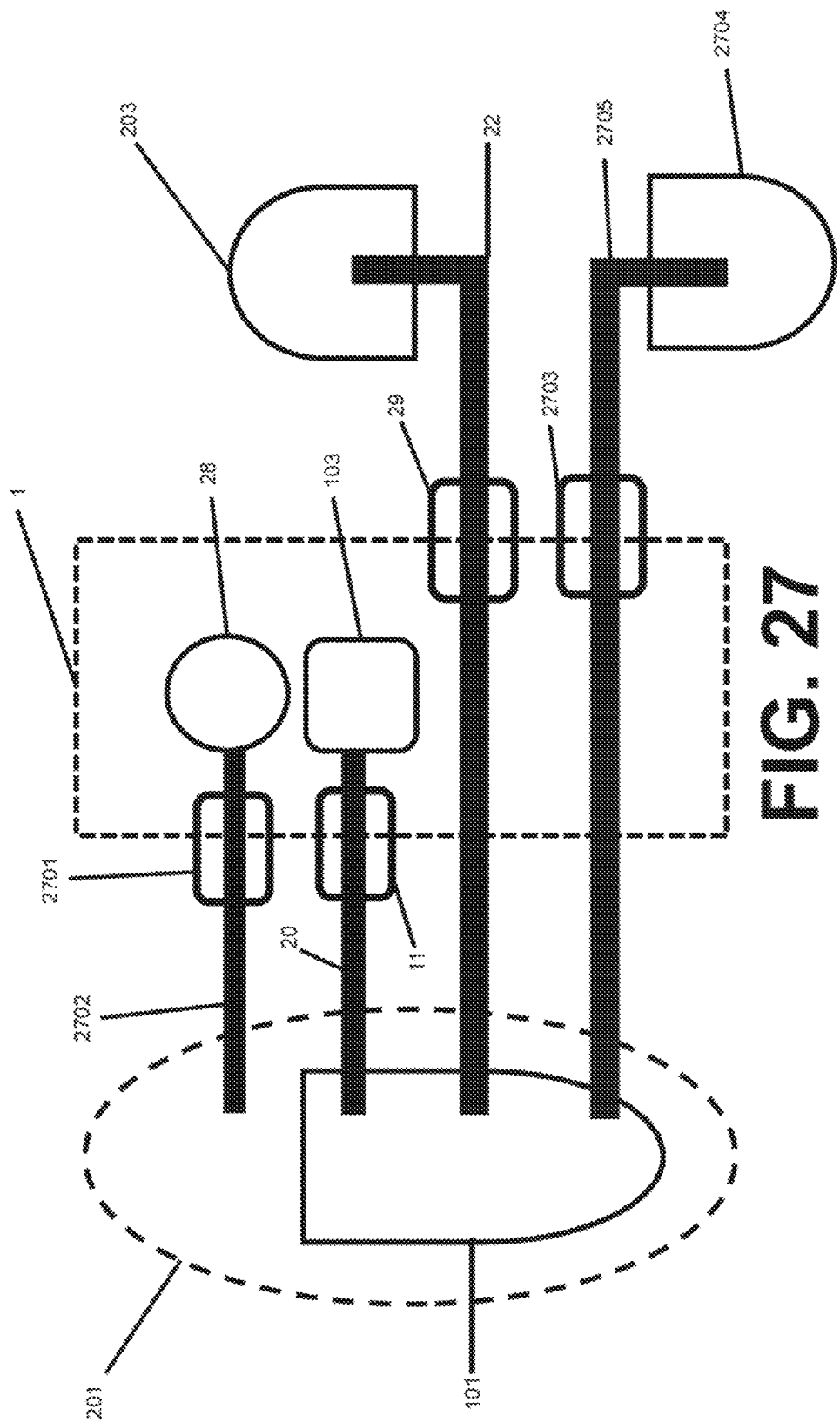
FIG. 27 is an illustration of the cleaning component, according to an embodiment of this disclosure.

In FIG. 27, a potential embodiment of the device cleaning component 107 is illustrated. The device cleaning component can be operated by multiple pumps 11, 29, 2701, 2703. The pumps are controlled by the device. In one embodiment, the device cleaning component 107 is operated by four pumps 11, 29, 2701, 2703 and tubing 20, 22, 2702, 2705 connecting the pumps to various components 101, 103, 28 of the device and to various fluid sources 203, 2704. The pumps 11, 29, 2701, 2703 can be peristaltic pumps. A pump 11 draws the sample using tubing 20 from the collection component 101 to the sample volume control mechanism 103. Another pump 2701 draws the excess sample using tubing 2702 from the urine collection bucket 28 to the waste water basin 201 in the toilet. Another pump 29 draws water into the collection component 101 using tubing 22 from a water source 203. The water will flush out, dilute out, and/or decontaminate the collection component 101 from biomolecules and/or bacteria from different people. If there is water in the collection component 101, it can be drawn into the sample volume control mechanism 103 using a pump 11 and tubing 20. Another pump 2703 draws cleaning fluid, such as, but not limited to, bleach or a diluted bleach solution, using tubing 2705 from a source of cleaning fluid 2704 to the collection component 101. The cleaning fluid will flush out, dilute out, and/or decontaminate the collection component 101 from biomolecules and/or bacteria from different users. If there is a cleaning fluid in the collection component 101, it can be drawn into the sample volume control mechanism 103 using a pump 11 and tubing 20.

In the embodiment where multiple pumps are used for the device cleaning component 107, an example of the cleaning process is explained. There can be multiple steps involved in cleaning the device, and more fluid is used in each subsequent step. This is done in order to dilute out any residual hCG without further spreading the hCG within the collection component 101. In one example, four stages are involved. The first two stages fill the collection component up with a cleaning fluid, where the first stage uses less cleaning fluid than the second stage. The cleaning fluid is drawn into the collection component 101 using a pump 2703 and tubing 2705 from a source of cleaning fluid 2704. The latter two stages fill the collection component up with water, where the third stage uses less water than the fourth stage. The water is drawn into the collection component 101 using a pump 29 and tubing 22 from a water source 203. After each stage, the cleaning fluid or water is drawn up into the sample volume control mechanism 103 using a pump 11 and tubing 20.

Figure 13:
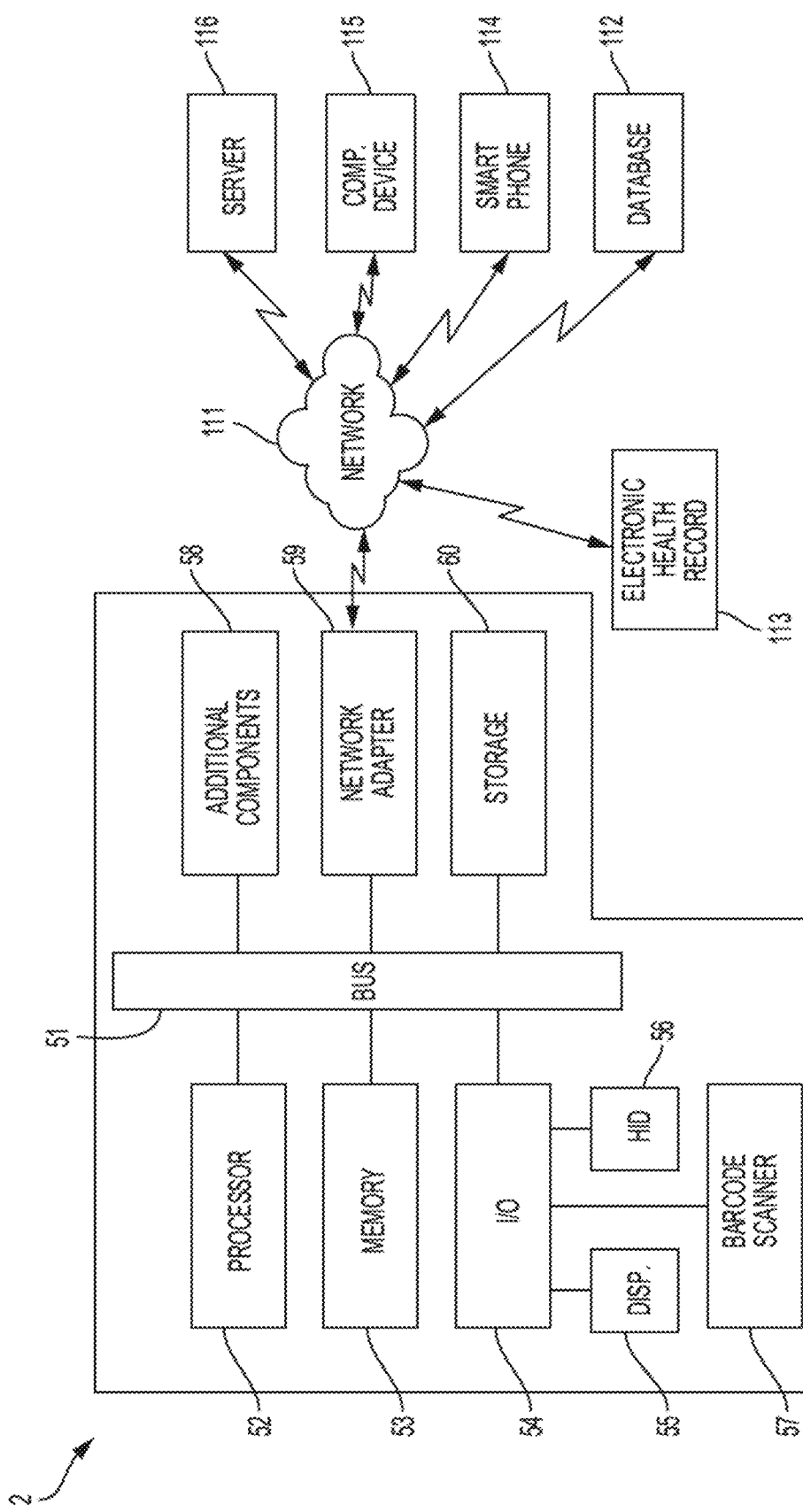
FIG. 13 is a block diagram view of an illustrative computerized device on which one or more aspects of the system may be operated, according to an embodiment of this disclosure.

Referring now to FIG. 13, an illustrative computerized device 2 will now be discussed in greater detail, without limitation. The computerized device 2 may include a processor 52, memory 53, network controller 59, and optionally an input/output (I/O) interface 54. Skilled artisans will appreciate additional embodiments of a computerized device that may omit one or more of the components or include additional components without limitation. The processor 52 may receive and analyze data. The memory 53 may store data, which may be used by the processor 52 to perform the analysis. The memory 53 may also receive data indicative of results from the analysis of data by the processor 52.

The memory 53 may include volatile memory modules, such as random access memory (RAM), and/or non-volatile memory modules, such as flash based memory. Skilled artisans will appreciate the memory to additionally include storage devices, such as, for example, mechanical hard drives, solid state data, and removable storage devices.

The computerized device may also include a network controller 59. The network controller 59 may receive data from other components of the computerized device to be communicated with other computerized devices 112, 113, 114, 115, 116 via a network 111. The communication of data may be performed wirelessly. More specifically, without limitation, the network controller 59 may communicate and relay information from one or more components of the computerized device, or other devices and/or components connected to the computerized device, to additional connected devices. Connected devices and/or software are intended to include databases 112, computer 115, mobile computing devices, smartphones 114, tablet computers, electronic health records 113, data servers 116, and other electronic devices that may communicate digitally with another device. In one example, the computerized device may be used as a server to analyze and communicate data between connected devices.

The computerized device 2 may also include an I/O interface 54. The I/O interface 54 may be used to transmit data between the computerized device and extended devices. Examples of extended devices may include, but should not be limited to, a display, external storage device, human interface device, printer, sound controller, barcode scanner, or other components that would be apparent to a person of skill in the art. For example, the I/O interface 54 may be used to with a barcode and/or RFID scanner 57 to detect an identification of a patient and electronically communicate such identifying information, for example, via WIFI, Bluetooth, and/or another network. Additionally, one or more of the components of the computerized device may be communicatively connected to the other components via the I/O interface 54.

The components of the computerized device 2 may interact with one another via a bus 51. Those of skill in the art will appreciate various forms of a bus that may be used to transmit data between one or more components of an electronic device, which are intended to be included within the scope of this disclosure.

The computerized device 2 may communicate with one or more connected devices via a network 111. The computerized device 2 may communicate over the network 111 by using its network controller 59. More specifically, the network controller 59 of the computerized device may communicate with the network controllers of the connected devices 114, 115, databases 112, and electronic health records 113. The network 111 may be, for example, the internet. As another example, the network 111 may be a WLAN. However, skilled artisans will appreciate additional networks to be included within the scope of this disclosure, such as intranets, local area networks, wide area networks, peer-to-peer networks, Bluetooth, RFID, and various other network formats. Additionally, the computerized device and/or connected devices may communicate over the network via a wired, wireless, or other connection, without limitation.

In operation, a method may be provided to automate analysis of samples to predict a medical condition. Those of skill in the art will appreciate that the following methods are provided to illustrate an embodiment of the disclosure, and should not be viewed as limiting the disclosure to only those methods or aspects. Skilled artisans will appreciate additional methods within the scope and spirit of the disclosure for performing the operations provided by the examples below after having the benefit of this disclosure. Such additional methods are intended to be included by this disclosure.

Figure 14:
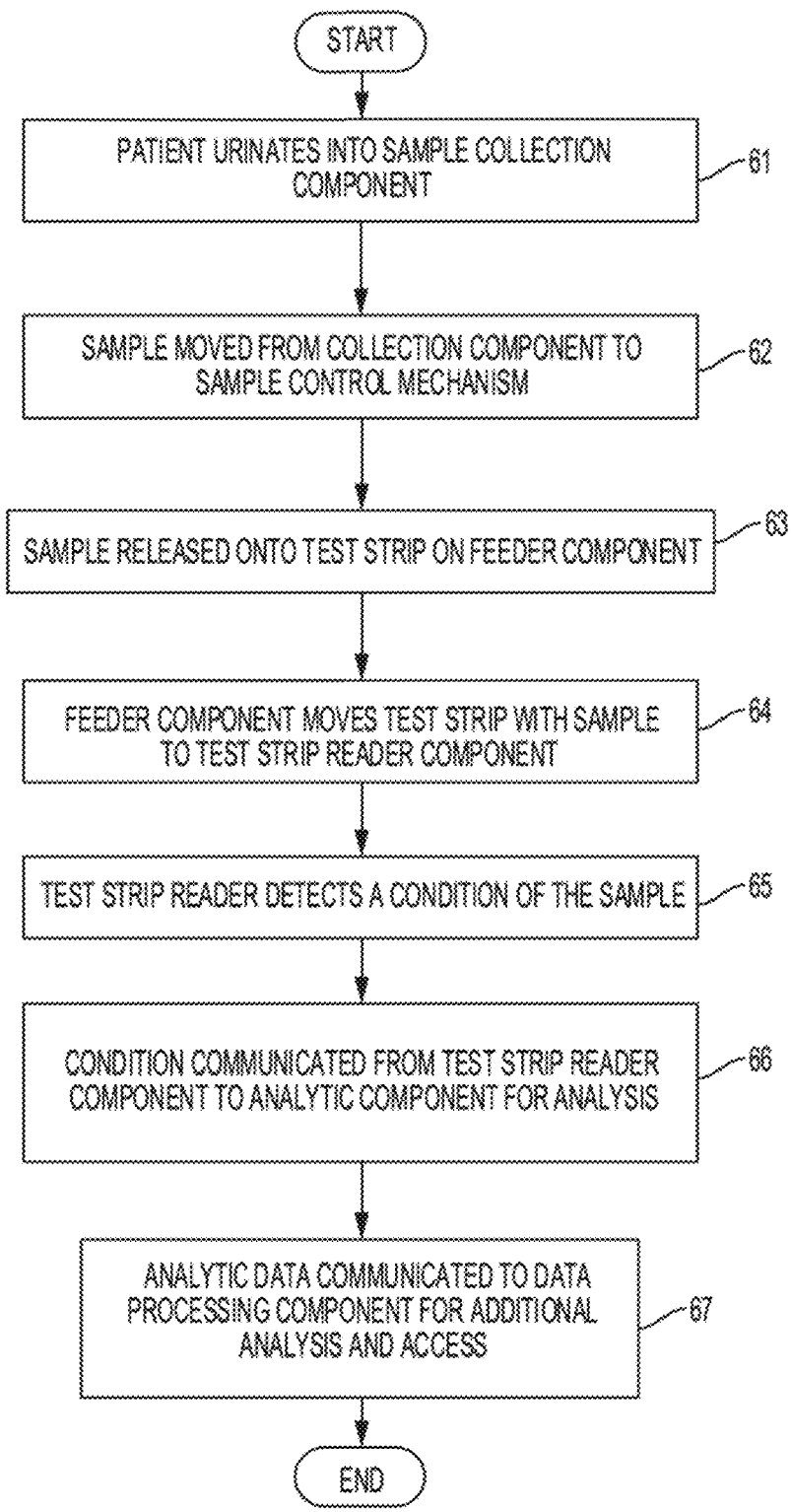
FIG. 14 is a flow chart view of a high level application of an illustrative diagnostic system, according to an embodiment of this disclosure.

Referring now to the flowchart of FIG. 14, an illustrative method for a high level application of an illustrative diagnostic system will be described, without limitation. The operation may begin with block 61 by a patient urinating in an aspect of the sample collection component 101, for example, a collection cup 24 installed in a toilet 200. In block 62, the sample may then be moved from the collection component 101 to the sample volume control component 103. Once a specifiable volume or an acceptable level of sample accumulates, in block 63, the sample may be released to a test strip of the feeder component. In block 64, the feeder component may move the test strip with the sample to the test strip reader component 105. In block 65, the test strip reader component 105 may then detect a condition of the sample. In block 66, a detected condition may be communicated from the test strip reader component 105 to the analytic component 106 for analysis. In block 67, the analytic data may additionally be communicated to the data processing component 108 for additional analysis and user access. The operation may then terminate.

Figure 15:
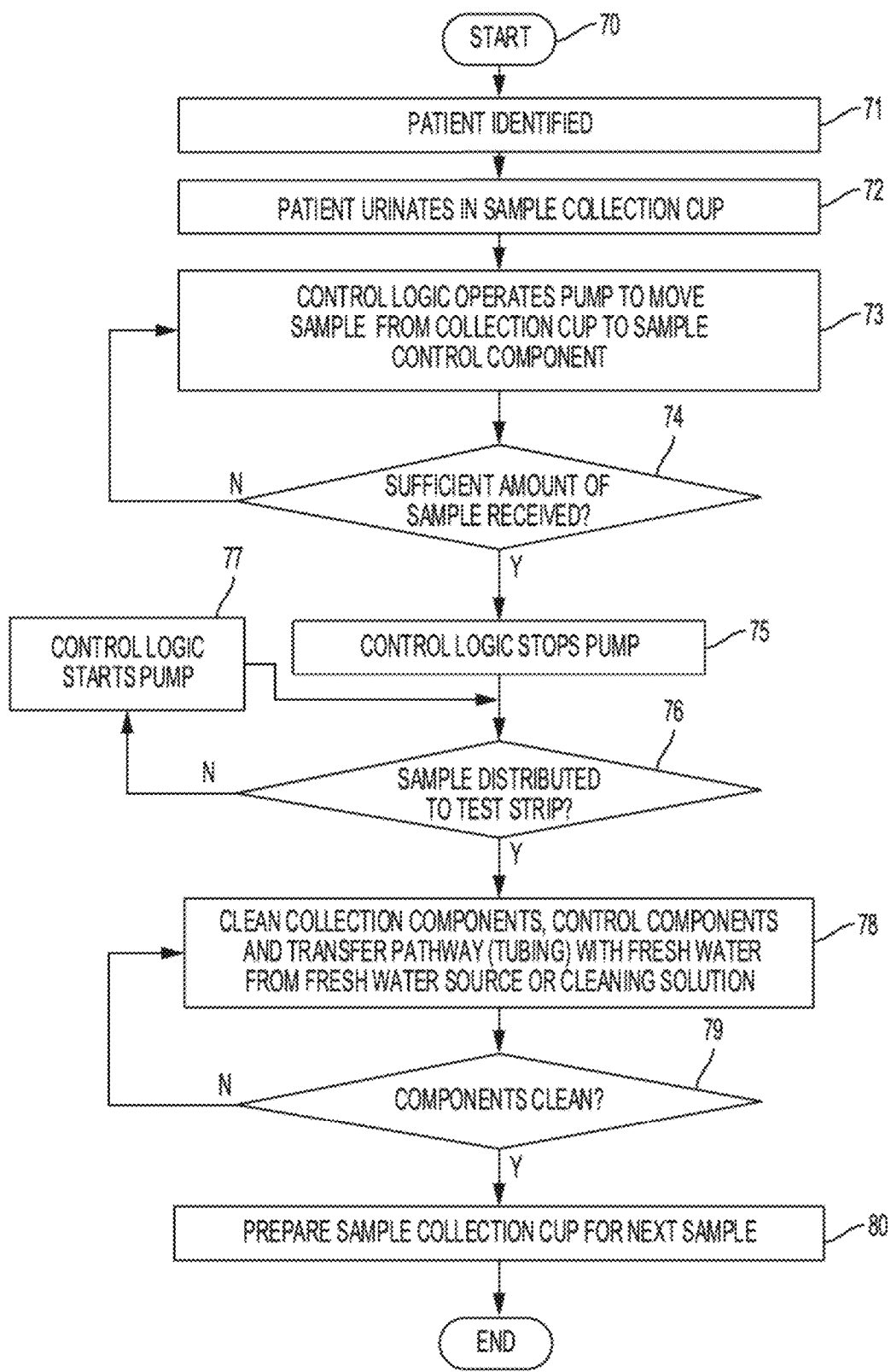
FIG. 15 is a flow chart view of a sample collection and transmission operation, according to an embodiment of this disclosure.

Referring now to the flowchart of FIG. 15, an illustrative method 70 for a sample collection and transmission operation will be described, without limitation. The operation may initially begin with block 71 with the patient scanning a barcode of a patient identification wristband or other form of identification, which may include a driver's license, credit/debit card, insurance card, and/or patient identification number entry into the user interface, without limitation. The operation may continue with block 72 by a patient providing a sample to the sample collection component 101. In one example, the patient may provide a sample by urinating into a collection cup 24. Once the sample is provided, in block 73, control logic 102 may operate a pump 11 to move some of the sample from the collection cup 24 to the sample volume control component 103.

In block 74 it may then be determined whether sufficient amounts of sample were received by the sample volume control component 103. If insufficient amounts of sample were received by the sample volume control component 103, in block 76, additional sample may be pumped from the sample collection component 101. If sufficient amounts of sample were received by the sample volume control component 103, in block 75 the control logic 102 may stop the pump 11.

In block 77, it may then be determined whether the sample was released to a test strip 25. If it is determined that the sample was not yet released to the test strip, in block 76, the control logic 102 may start the pump 11 again to release the sample onto the test strip. If it is determined that the sample was released to the test strip, in block 78, the control logic 102 may begin the cleaning process.

After releasing the sample to the test strip, in block 78, the device cleaning component 107 may clean the sample collection component 101 and/or volume control components 103 with fresh water from a connected water source 203. Skilled artisans will appreciate that additional cleaning solutions may be used, without limitation. The operation may then determine whether the components are sufficiently clean in block 79.

If it is determined that the components are not yet sufficiently clean, the device cleaning component 107 may continue the cleaning operation in block 78. If it is determined that the components are sufficiently clean in block 79, the operation may prepare the sample collection component to receive the next sample in block 80. The operation may then terminate.

Figure 16:
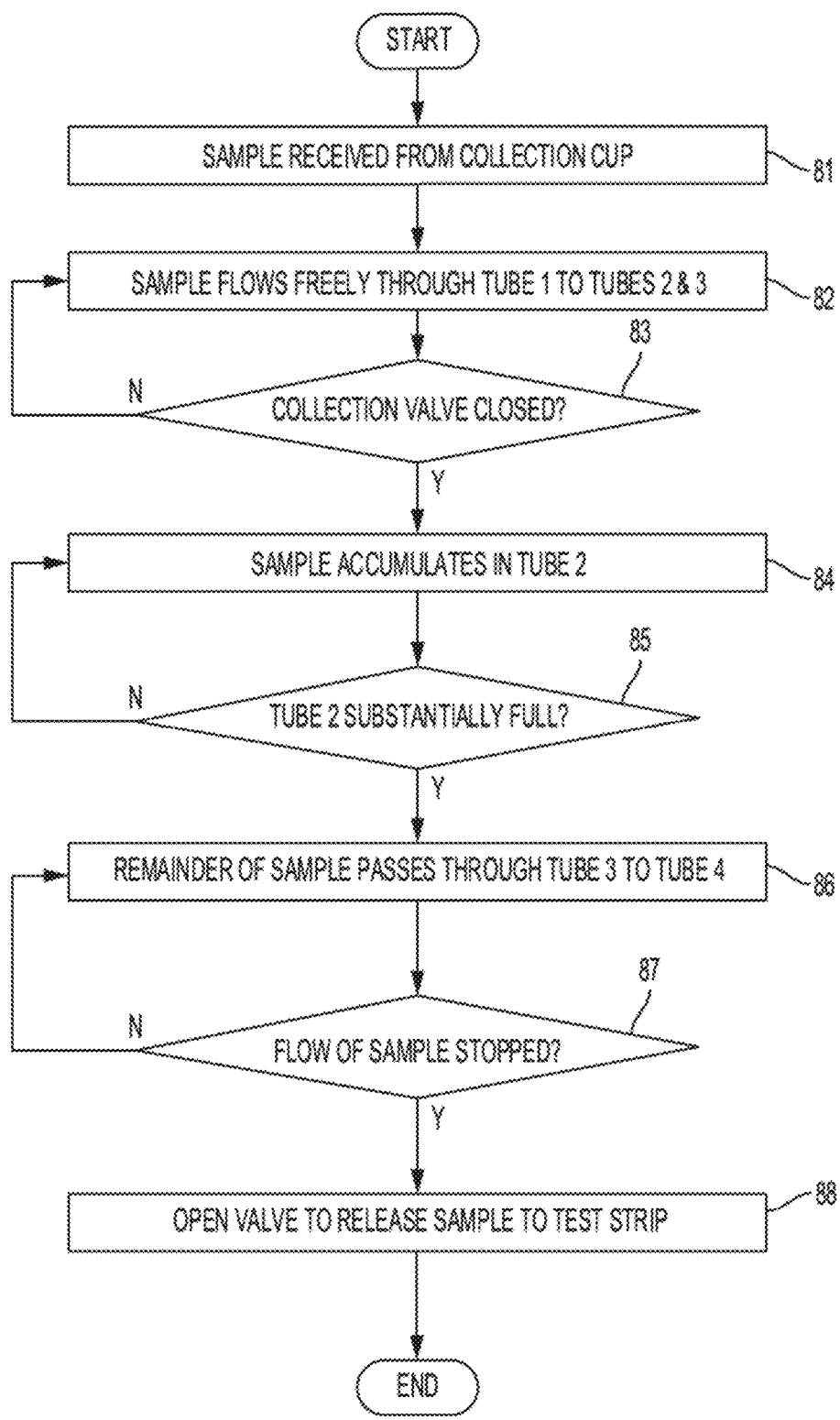
FIG. 16 is a flow chart view of a sample volume control operation, according to an embodiment of this disclosure.

Referring now to the flowchart of FIG. 16, an illustrative method for a sample volume control operation will be described, without limitation. The operation may begin in block 81 by receiving the sample from the sample collection component 101. In block 82 the sample may freely flow through first tube 31 of the illustrative sample volume control component 103 to second tube 32 and third tube 33. In block 83, the operation may then determine if the valve 12 for the collecting tube, in this example, second tube 32, is closed.

If it is determined that the valve 12 associated with the collecting second tube 32 is not closed, in block 82, the sample may continue to flow freely through first tube 31 to second tube 32 and third tube 33. If it is determined that the valve 12 is closed, in block 84, the sample may accumulate in second tube 32. In block 85, it may then be determined whether second tube 32 is substantially full of sample.

If it is determined that second tube 32 is not substantially full of sample, in block 84, then sample may continue to accumulate in second tube 32. If it is determined that second tube 32 is substantially full, in block 86, the remainder of sample may pass over second tube 32 and exit through third tube 33 and fourth tube 34. In block 87, it may then be determined whether the flow of sample has stopped.

If it is determined that the flow of sample has not stopped, in block 86, the remaining sample may continue to flow through third tube 33 and fourth tube 34. If it is determined that the flow of sample has stopped, in block 88, the operation may selectively open the valve 12 at the exit end of second tube 32 to release the sample to the test strip. The operation may then terminate.

Referring now to the flowchart of FIG. 17, an illustrative method for a sample delivery and detection operation will be described, without limitation. The operation may begin in block 401 by reels 13, 14 of the test strip usage component 104 moving a test strip on the film 18 near the valve 12 of the sample volume control component 103. In block 402, the sample volume control component 103 may then open the valve 12 and release the sample onto the test strip. The flow reader component may wait a definable or prespecified amount of time after the sample volume is released onto the test strip before beginning the process of detecting the condition. In block 403, the reels 13, 14 may move the test strip with the sample on the film 18 to the test strip reader component 105 through ways including, but not limited to, a specific number of reel steps using a stepper motor, a reflective opto-interrupter, a camera, or a light-based sensor to determine when the reel 13, 14 should stop, or other mechanical methods. In block 404, the test strip reader component 105 may detect a condition of the sample and/or test strip and it may then be determined whether the test strip reader component 105 has finished detecting the condition.

If it is determined that the test strip reader component 105 has not finished detecting the condition, in block 404, the test strip reader component 105 may continue detecting the condition. If it is determined that the test strip reader component 105 has finished detecting the condition, in block 405, the reels 13, 14 may move the test strip with the sample on the film 18 away from the test strip reader component 105. It may then be determined whether a new sample is to be received in block 406.

If it is determined that a new sample is to be received in block 406, the operation of FIG. 17 may begin again with the reels 13, 14 moving the next test strip near the valve 12 of the volume control component 103. If it is determined that a new sample will not be received in block 406, the operation may terminate.

Figure 18:
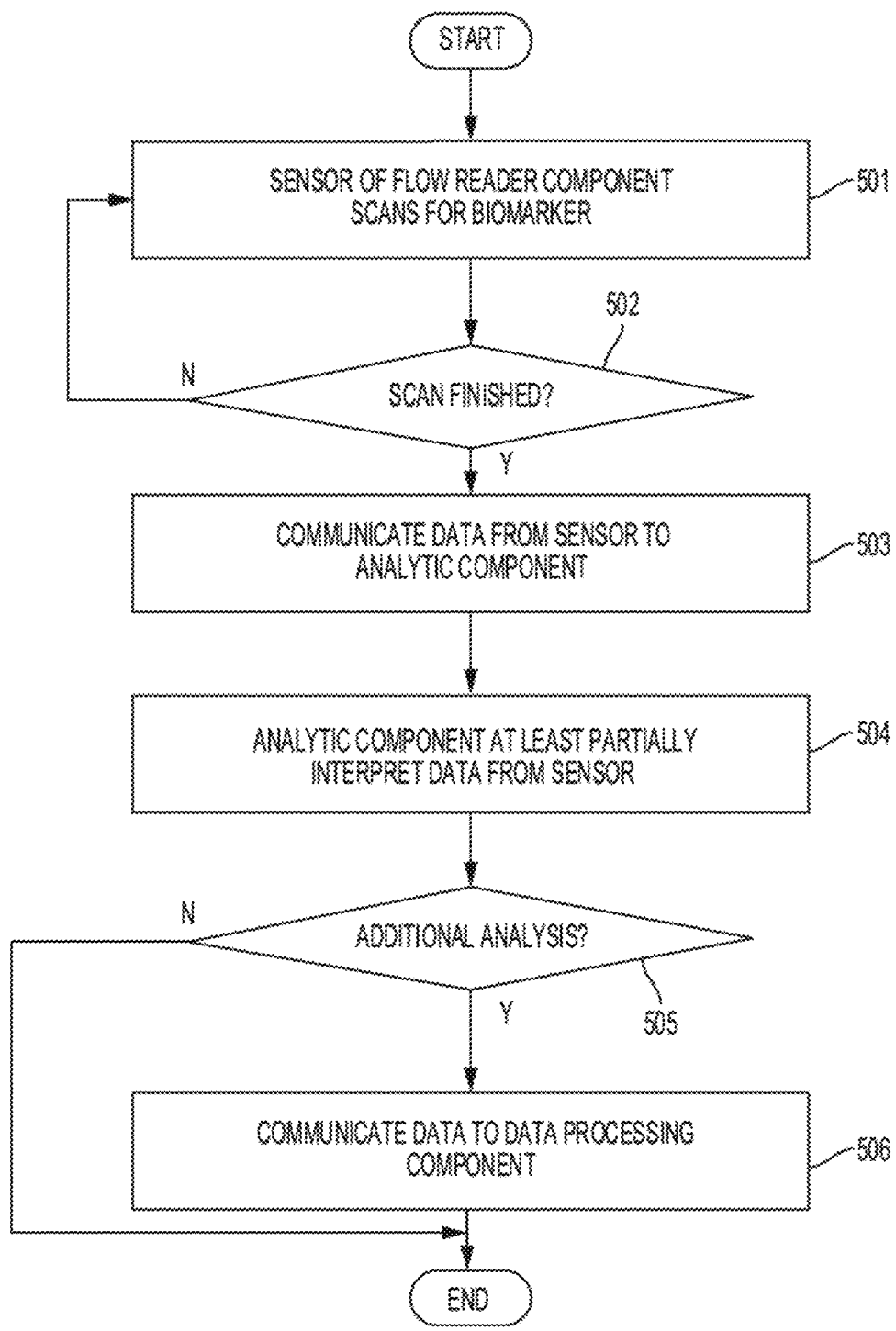
FIG. 18 is a flow chart view of a sample analysis and digitization operation, according to an embodiment of this disclosure.

Referring now to the flowchart of FIG. 18, an illustrative method for a sample analysis and digitization operation will be described, without limitation. The operation may begin with block 501 by a sensor of the test strip usage component 104 scanning and/or imaging for a biomarker. Skilled artisans will appreciate sensors may scan for additional indicators of a condition, without limitation. In block 502, it may then be determined whether the scan and/or imaging is finished.

If it is determined that the scan and/or imaging is not yet finished, in block 501, the sensor may continue to scan and/or image for the biomarker. If it is determined that the scan and/or imaging has finished, in block 503, the operation may communicate data from the sensor to the analytic component 106. In block 504, the analytic component 106 may then at least partially interpret data detected from the sensor. In block 505, it may then be determined whether additional analysis is needed.

If it is determined that no additional analysis is needed in block 505, the operation may terminate. If it is determined that additional analysis is needed in block 506, the data may be communicated to the data processing component 108. Additionally, if it is determined that the data may be shared with a user, the data may be communicated to the data processing component 108. The operation may then terminate.

Figure 19:
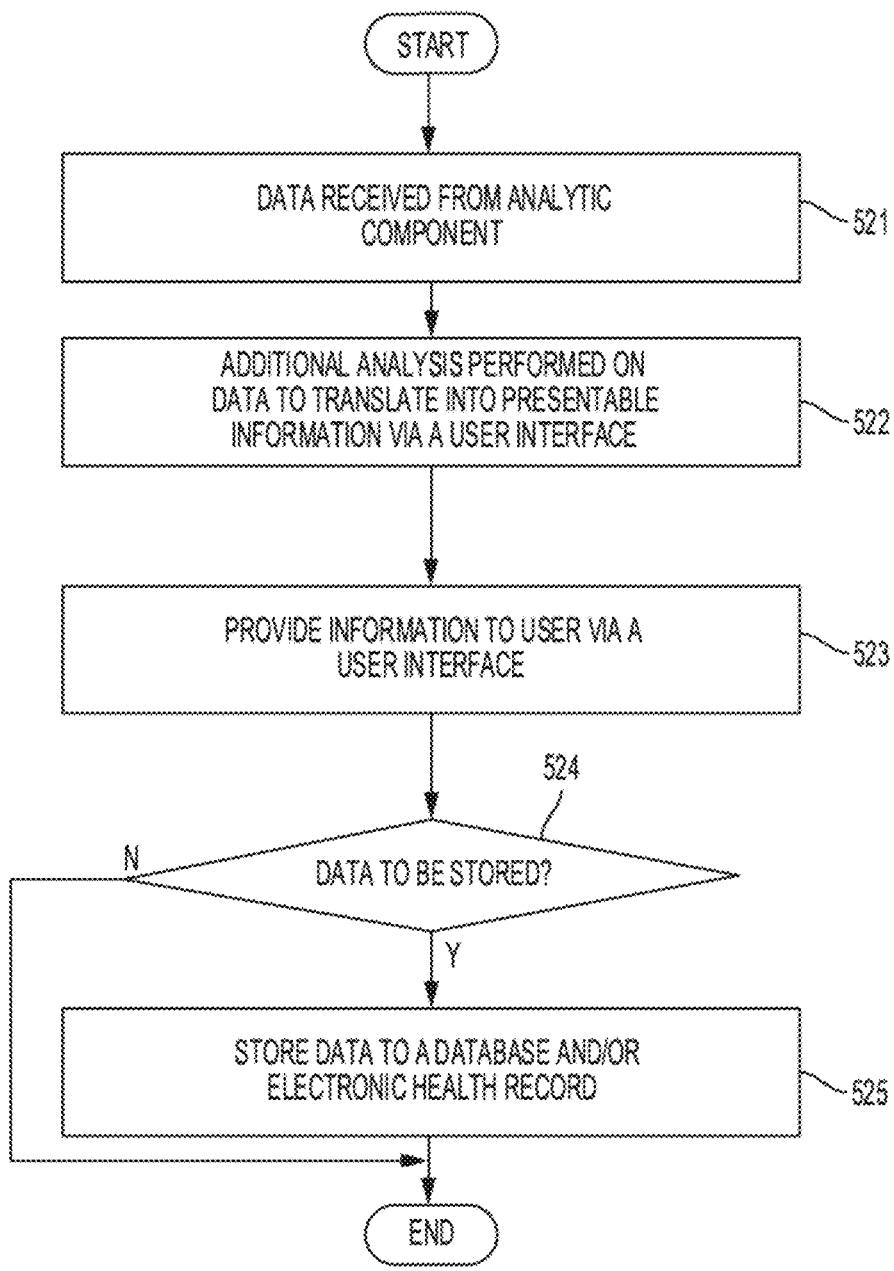
FIG. 19 is a flow chart view of a data communication and sharing operation, according to an embodiment of this disclosure.

Referring now to the flowchart of FIG. 19, an illustrative method for a data communication and sharing operation will be described, without limitation. The operation may begin in block 521 by receiving data from the analytic component 106. In block 522 additional analysis may be performed on the data to translate the data into presentable information via a user interface 110, for example, in a format that supports syntactic, semantic, and/or other functional interoperability. In block 523, the information may be provided to a user via a user interface 110. In block 524, it may then be determined whether to store the data.

If it is determined that the data should not be stored in block 524, the operation may terminate. If it is determined that the data should be stored in block 524, in block 525, the data may be stored to a database 112, for example, in a format that supports syntactic, semantic, and/or other functional interoperability. The data may also be stored in an electronic health record 113, for example, in a format that supports syntactic, semantic, and/or other functional interoperability. The database 112 and/or electronic health record 113 may optionally be connected via a network 111. The operation may then terminate.

Figure 20:
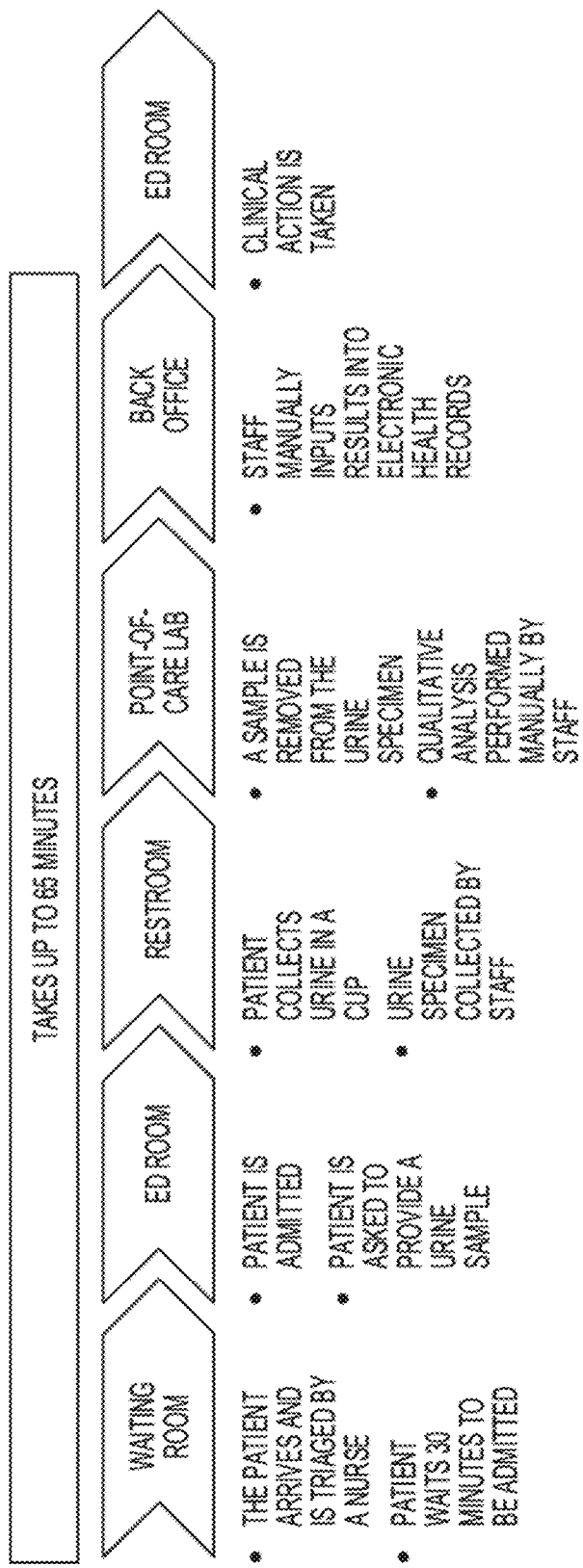
FIG. 20 is a diagrammatic view of the deficiencies of typical pregnancy screening operations as performed in the prior art.

Referring now to the flowchart of FIG. 20, deficiencies of typical pregnancy screening operations as performed in the prior art will be described, without limitation. As illustrated in FIG. 20, testing operations performed in the prior art typically suffer from low adherence to pregnancy screening guidelines, due in part to requiring a time consuming and complex testing process. For example, a typical testing process conducted with the deficient methods of the prior art are estimated to take about 65 minutes.

The first step of the deficient testing process may begin in the waiting room. Here, the patient may arrive and be triaged by a nurse. The patient may wait approximately 30 minutes to be admitted. The second step of the deficient testing process may occur in an emergency department, urgent care, or exam room, for example. Here, the patient be admitted and asked to provide a urine sample. The third step of the deficient testing process may occur in a restroom, for example. Here, the patient may collect urine in a cup, which may then be collected by a staff member. The cup including the sample may be left in a staging area between interaction by the patient and the staff member. The fourth step of the deficient testing process may occur in a point-of-care laboratory, for example. Here, the sample may be removed from the urine specimen. A qualitative analysis may be performed manually by a staff member. The fifth step of the deficient testing process may occur in a back office, for example. Here, the staff member may manually input results from the test into an electronic health record. The sixth step of the deficient testing process may again occur in the emergency department, urgent care, or exam room, for example. Here, clinical action may be taken.

Figure 21:
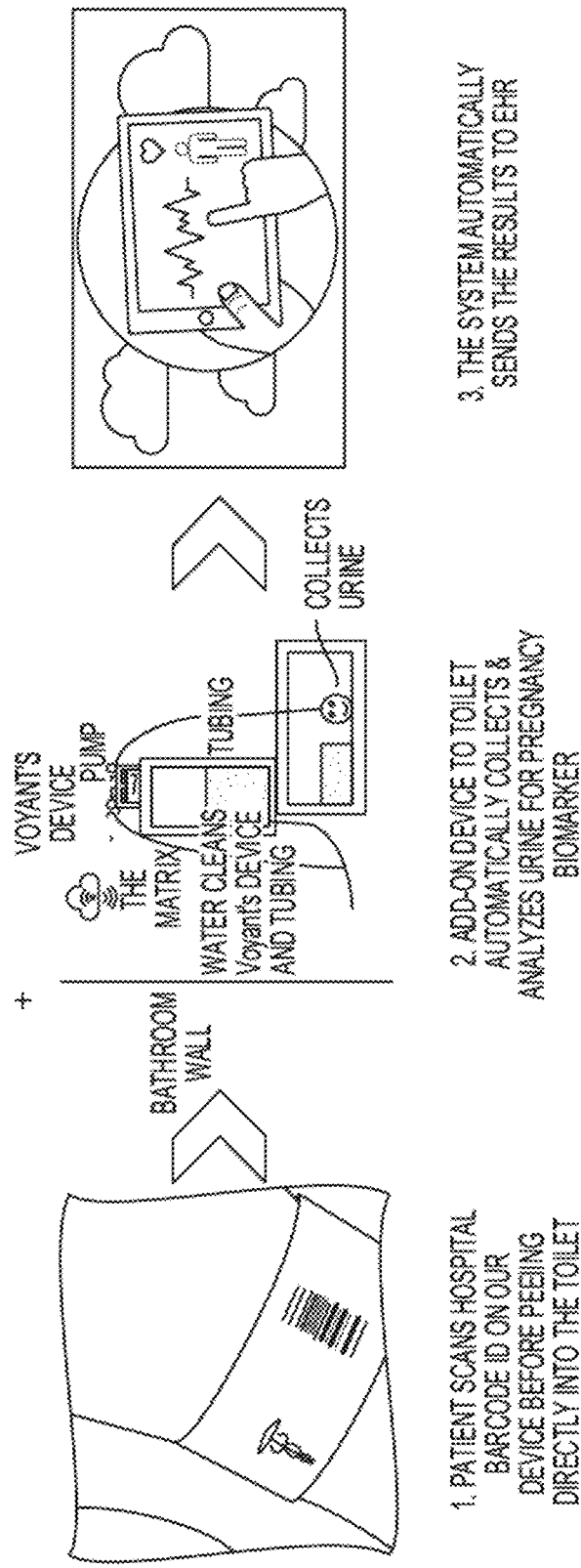
FIG. 21 is a diagrammatic view of a pregnancy screening performed using at least one embodiment of this disclosure.

Referring now to the flowchart of FIG. 21, pregnancy screening performed using at least one embodiment of this disclosure will be described, without limitation. In this example screening process, an embodiment of this disclosure may substantially automate the pregnancy testing process in the emergency department, urgent care, or exam room, for example. The substantially automated process may begin with a patient scanning a hospital barcode ID using a device of the system before submitting a sample. In at least one embodiment, the sample may be provided directly into a toilet equipped with a device of this disclosure. The device installed into the toilet may substantially automatically collect and analyze urine for a pregnancy biomarker. The process may then substantially automatically send the results to an electronic health record.

Figure 22:
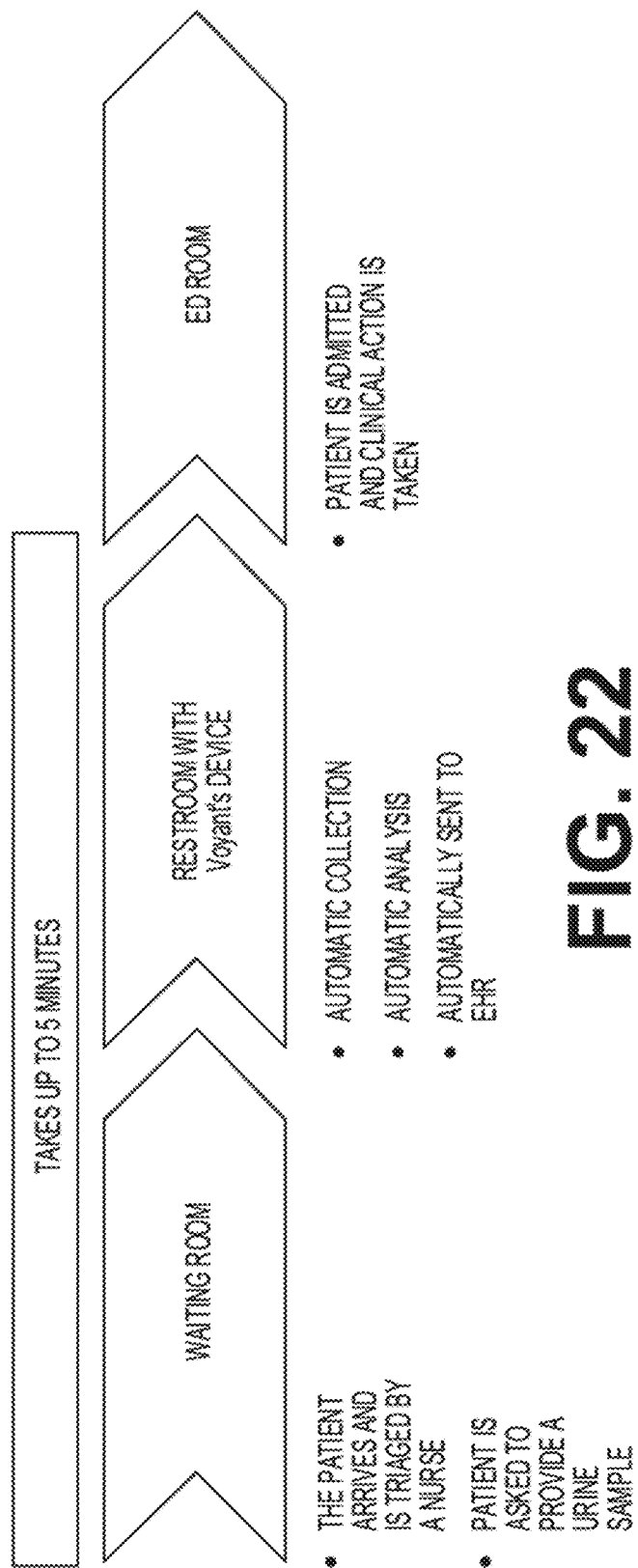
FIG. 22 is a diagrammatic view of typical pregnancy screening operations using at least one embodiment of this disclosure.

Referring now to the flowchart of FIG. 22, typical pregnancy screening operations using at least one embodiment of this disclosure will be described, without limitation. For example, a typical testing process conducted with the advantageous methods of this disclosure is estimated to take about 5 minutes.

The first step of the advantageous testing process of this disclosure may begin in the waiting room. Here, the patient may arrive and be triaged by a nurse. The patient may then be asked to provide a urine sample. The second step of the advantageous testing process of this disclosure may begin in the restroom. Here, the sample may be substantially automatically collected from the patient, substantially automatically analyzed, and substantially automatically sent to an electronic health record. The third step of the advantageous testing process of this disclosure may begin in the emergency department, urgent care, or exam room. Here, the patient may be admitted and clinical action may be taken.

Figure 23:
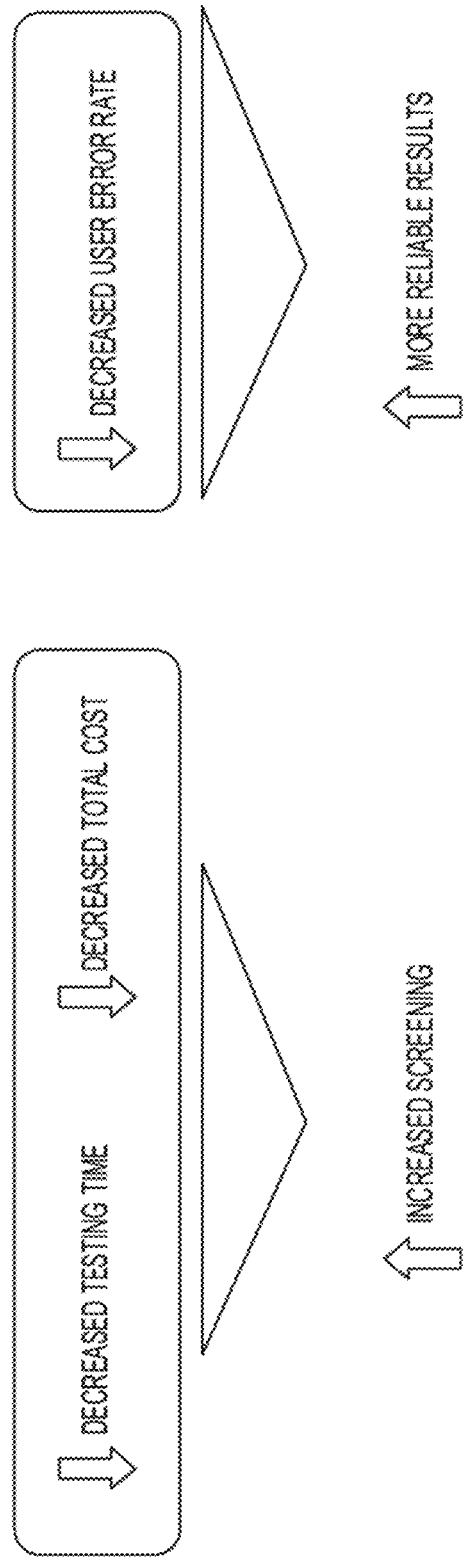
FIG. 23 is a diagrammatic view of advantages provided by the testing of a medical condition, according to an embodiment of this disclosure.

Referring now to the flowchart of FIG. 23, illustrative advantages provided by the testing of a medical condition will be described, without limitation. The system and methods included by this disclosure may give hospitals, emergency departments, urgent care facilities, clinical offices, and other locations tools to better provide care to patients. Better care may be facilitated by decreasing testing time and decreasing total costs, which may result in increased screening of incoming patients. Better care may additionally include decreased user error rate, which may result in more reliable results.

Figure 24:
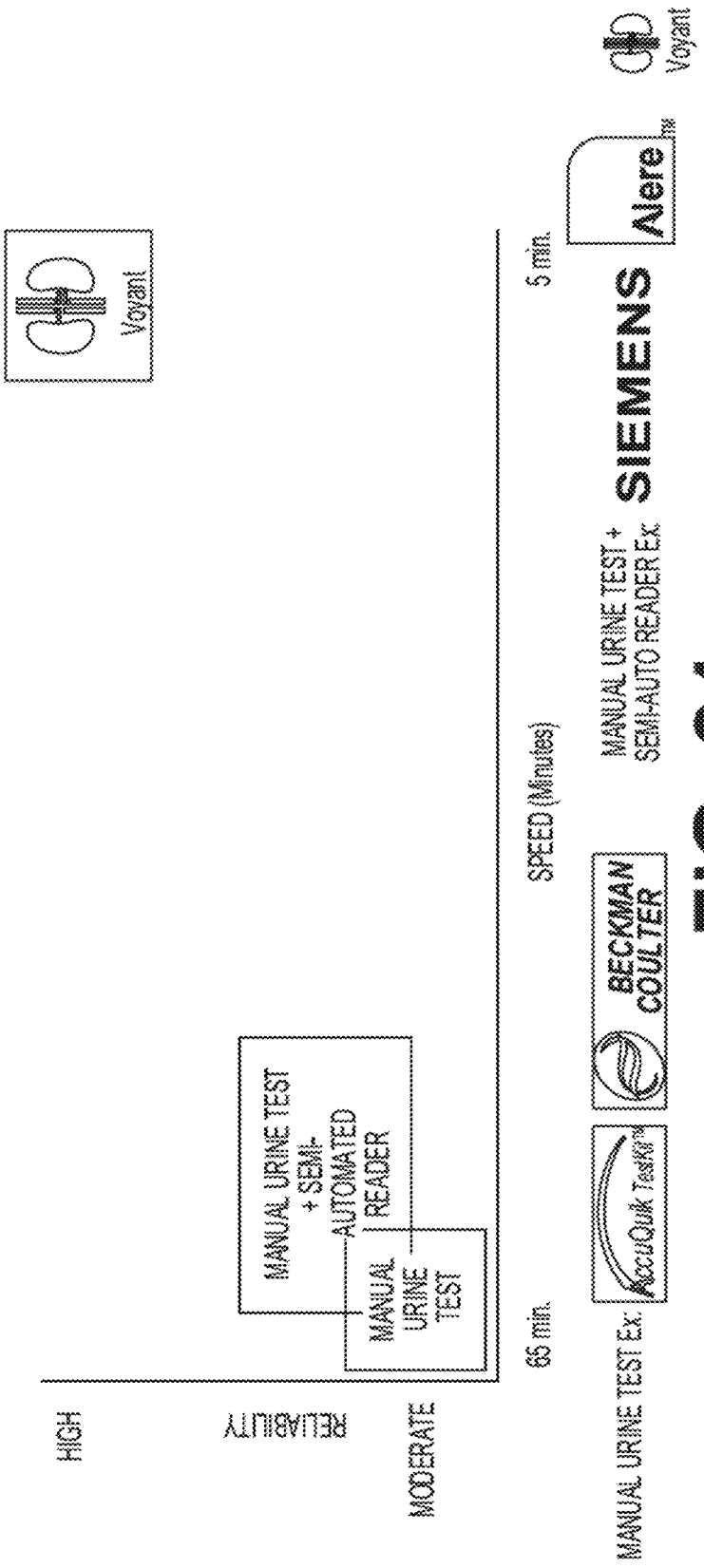
FIG. 24 is a diagrammatic view contrasting advantages of the testing of a medical condition as provided by an embodiment of this disclosure with deficiencies in testing techniques of the prior art.

Referring now to the flowchart of FIG. 24, a contrast between advantages of the testing of a medical condition as provided by an embodiment of this disclosure with deficiencies in testing techniques of the prior art will be described, without limitation. Prior testing techniques may include manual urine tests, which may optionally include semiautomated readers. As illustrated in FIG. 24, prior testing techniques may in provide moderate reliability, while taking a substantial amount of time to complete. Inclusion of semi-automated readers may somewhat increase reliability and decrease testing time, but still provide results and an experience requiring improvement. The testing system and methods included by this disclosure are represented by the "Voyant" icon, illustrating substantially high reliability and substantially low testing times. The testing system and methods included by this disclosure may provide a significant improvement over the current state of the art, which may advantageously facilitate widespread testing of CKD, pregnancy, and other medical conditions.

Figure 29:
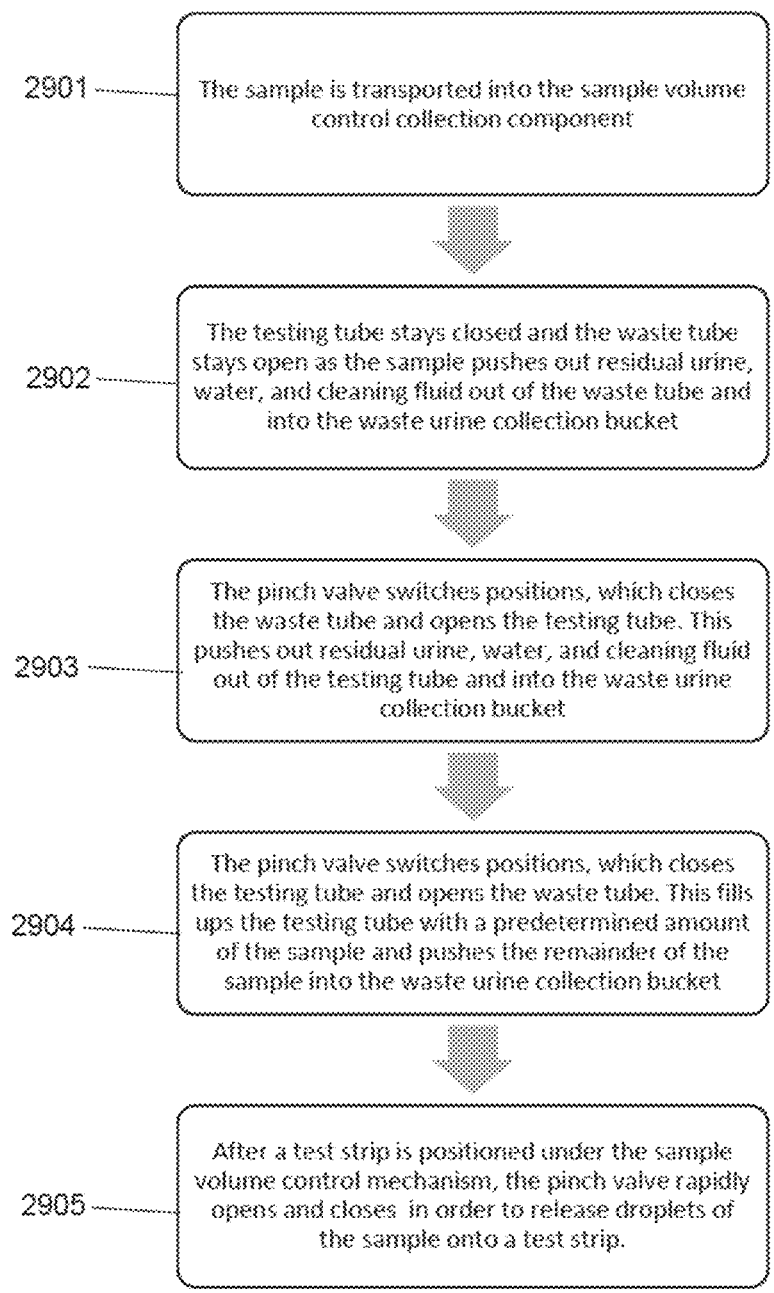
FIG. 29 is a flow chart view of a method, according to an embodiment of this disclosure.

Referring now to FIG. 29, another process for the sample volume control component is described. After the sample is in the sample collection component 101, the sample is transported using a pump 11 and tubing 20, 31B into the sample volume control component 103. This step is represented in block 2901. The pinch valve 12B is set to have the testing tube 32B closed and the waste tube 33B open. The sample passes through the sample volume control component 103 to flush out residual urine, water, or cleaning fluid through the waste tube 33B. This step is represented in block 2902. The pinch valve 12B is switched to open the testing tube 32B and close the waste tube 33B. This flushes out residual urine, water, or cleaning fluid through the testing tube 32B. This step is represented in block 2903. The pinch valve 12B is switched to open the waste tube 33B and close the testing tube 32B. This fills the testing tube 32B with the sample and flushes the remaining sample out of the waste tube 33B. This step is represented in block 2904. A test strip is positioned underneath the testing tube 32B of the sample volume control mechanism 103. The pinch valve 12B opens and closes rapidly to allow drops of the sample from the testing tube 32B to fall onto the test strip. This step is represented in block 2905.

Figure 30:
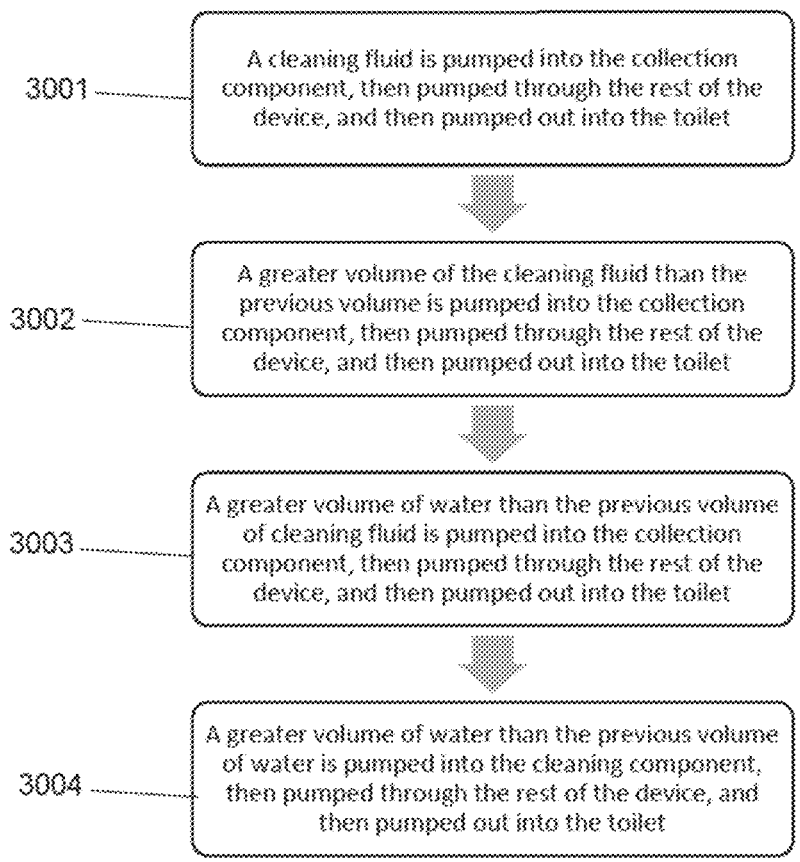
FIG. 30 is a flow chart view of a method, according to an embodiment of this disclosure.

Referring now to FIG. 30, the process for the device cleaning component 107 is described. After the sample has been analyzed, the system is cleaned. First, cleaning fluid, such as, but not limited to, bleach, from a source of cleaning fluid 2704 is transported to the collection component 101 using a pump 2703 and tubing 2705. From the collection component 101, the cleaning fluid and any residual urine is transported into the device 1 to clean it using tubing 20 and a pump 11 and then flushed out of the device using a pump 2701 and tubing 2702. This step is shown in block 3001. Second, cleaning fluid from a source of cleaning fluid 2704 is transported to the collection component 101 using a pump 2703 and tubing 2705. A greater volume of cleaning fluid is transported in this step than the volume of cleaning fluid transported in the step represented in block 3001. From the collection component 101, the cleaning fluid and any residual urine is transported into the device 1 to clean it using tubing 20 and a pump 11 and then flushed out of the device using a pump 2701 and tubing 2702. This step is shown in block 3002. Third, water from a water source 203 is transported to the collection component 101 using a pump 29 and tubing 22. A greater volume of water is transported in this step than the volume of cleaning fluid transported in the step represented by block 3002. From the collection component 101, the water and any residual urine is transported into the device 1 to clean it using tubing 20 and a pump 11 and then flushed out of the device using a pump 2701 and tubing 2702. This step is shown in block 3003. Last, water from a water source 203 is transported to the collection component 101 using a pump 29 and tubing 22. A greater volume of water is transported in this step than the volume of water transported in the step represented by block 3003. From the collection component 101, the water and any residual urine is transported into the device 1 to clean it using tubing 20 and a pump 11 and then flushed out of the device using a pump 2701 and tubing 2702. This step is represented by block 3004.

While various aspects have been described in the above disclosure, the description of this disclosure is intended to illustrate and not limit the scope of the invention. The invention is defined by the scope of the claims accompanying a subsequent nonprovisional patent application and not the illustrations and examples provided in the above disclosure. Skilled artisans will appreciate additional aspects of the invention, which may be realized in alternative embodiments, after having the benefit of the above disclosure. Other aspects, advantages, embodiments, and modifications are within the scope of the claims that may result from this disclosure.

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those described herein, will be apparent to those skilled in the art from the foregoing descriptions. Such modifications and variations are intended to fall within the scope of the appended claims.

The above detailed description describes various features and operations of the disclosed systems, devices, and methods with reference to the accompanying figures. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations.

With respect to any or all of the message flow diagrams, scenarios, and flow charts in the figures and as discussed herein, each step, block, operation, and/or communication can represent a processing of information and/or a transmission of information in accordance with example embodiments. Alternative embodiments are included within the scope of these example embodiments. In these alternative embodiments, for example, operations described as steps, blocks, transmissions, communications, requests, responses, and/or messages can be executed out of order from that shown or discussed, including substantially concurrently or in reverse order, depending on the functionality involved. Further, more or fewer blocks and/or operations can be used with any of the message flow diagrams, scenarios, and flow charts discussed herein, and these message flow diagrams, scenarios, and flow charts can be combined with one another, in part or in whole.

A step, block, or operation that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical operations or actions in the method or technique. The program code and/or related data can be stored on any type of computer-readable medium such as a storage device including RAM, a disk drive, a solid state drive, or another storage medium.

The computer-readable medium can also include non-transitory computer-readable media such as computer-readable media that store data for short periods of time like register memory and processor cache. The computer-readable media can further include non-transitory computer-readable media that store program code and/or data for longer periods of time. Thus, the computer-readable media may include secondary or persistent long term storage, like ROM, optical or magnetic disks, solid state drives, compact-disc read only memory (CD-ROM), for example. The computer-readable media can also be any other volatile or non-volatile storage systems. A computer-readable medium can be considered a computer-readable storage medium, for example, or a tangible storage device.

Moreover, a step, block, or operation that represents one or more information transmissions can correspond to information transmissions between software and/or hardware modules in the same physical device. However, other information transmissions can be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

While various aspects and embodiments have been disclosed herein, other aspects and embodiments will be apparent to those skilled in the art. The various aspects and embodiments disclosed herein are for purpose of illustration and are not intended to be limiting, with the true scope being indicated by the following claims.

What is claimed:

1. A system comprising:
   a collection component configured to receive a sample from a patient, wherein the collection component is configured to be activated and deactivated based on patient input, and wherein the collection component comprises smooth sides so as to minimize a residual amount of the sample that sticks on walls of the collection component after patient use;
   a plurality of test strips configured to indicate a condition of the patient when exposed to the sample;
   a fluid transportation system comprising a sample volume control component, wherein the sample volume control component comprises:
     a first tube;
     a three-way valve;
     a second tube connected to the first tube via the three-way valve;
     a third tube connected to the first tube via the three-way valve;
     a fourth tube, and
   wherein the fluid transportation system is configured to:
     transport a first portion of the sample from the collection component to a first test strip of the plurality of test strips at a predetermined position relative to the collection component, wherein transporting the first portion of the sample from the collection component to the first test strip comprises:
       transporting the sample through the first tube;
       separating the sample into the first portion and a second portion using the three-way valve;
       transporting the first portion of the sample through the second tube via the three-way valve;
       transporting the second portion of the sample through the third tube via the three-way valve when the second tube is substantially full with the first portion of the sample; and
       transporting the second portion of the sample through the fourth tube;
     expose the first test strip to the first portion of the sample; and
     deliver fresh water or another cleaning solution to the collection component to clean the collection component;
   a sensor configured to capture an image of the first test strip exposed to the first portion of the sample when the first test strip is near the sensor, wherein the image indicates the condition of the patient;
   a computing device configured to analyze the image of the first test strip captured by the sensor in order to determine the condition of the patient; and
   a motor configured to:
     position the first test strip near the sensor after the first test strip is exposed to the first portion of the sample; and
     position a second test strip of the plurality of test strips at the predetermined position after the first test strip is exposed to the first portion of the sample.

2. The system of claim 1, further comprising an electronically-stored medium,
   wherein the electronically-stored medium is configured to store the determined condition of the patient,
   wherein the computing device is configured to transmit the determined condition of the patient to an additional electronically-stored medium for inclusion in an electronic health record of the patient, and
   wherein the electronic health record of the patient contains additional health data relating to the patient.

3. The system of claim 2, wherein the additional data relating to the patient comprises at least one of a unique patient identifier, a result of the test strip, or an image of the test strip.

4. The system of claim 1, further comprising a user interface configured to share the image with a physician, the patient, or another selected party.

5. The system of claim 1, further comprising a scanner configured to detect an identification of the patient,
   wherein the scanner comprises a barcode scanner or a radio-frequency identification (RFID) scanner,
   wherein, upon the scanner detecting the identification of the patient, the system is configured to receive, process, and analyze the sample in an automated fashion, and
   wherein the computing device is configured to transmit the condition of the patient to an electronically-stored medium for inclusion in an electronic health record of the patient based on the identification of the patient.

6. The system of claim 1,
   wherein the first tube, the second tube, the third tube, or the fourth tube is made of a hydrophobic material that allows fluid to pass through the tube without sticking to the walls of the respective tube.

7. The system of claim 6, wherein the material that allows fluid to pass through the respective tube without sticking to the walls of the tube comprises silicone, polytetrafluoroethylene (PTFE/TEFLON®), or polyethylene.

8. The system of claim 1, further comprising an anti-contamination film connected to a first set of opposing reels and located above or adjacent to the collection component,
   wherein, when rotated by a separate motor, the first set of opposing reels is configured to:

move a used area of the anti-contamination film away from the collection component after the first test strip is exposed to the first portion of the sample; and move an unused area of the anti-contamination film toward the collection component after the first test strip is exposed to the first portion of the sample.

9. The system of claim 1, wherein the fluid transportation system is configured to deliver the fresh water or another cleaning solution to the collection component to clean the collection component or the volume control component.

10. The system of claim 1, wherein the tests strips comprise aptamers, antibodies, chemical reagents, biomolecules, or a substance that binds or reacts to the sample.

11. The system of claim 1, further comprising:
opposing reels; and
a belt that spans the opposing reels, wherein the plurality of test strips is located on the belt, wherein the opposing reels are rotatable in order to move the belt and reposition the plurality of test strips, wherein the test strips are spaced sufficiently far apart from one another on the belt such that a portion of the sample can be dispensed on one of the test strips without getting any of the sample on other test strips, and wherein the test strips are spaced from one another on the belt by a distance between 100 mm and 150 mm.

12. The system of claim 11,
wherein the plurality of test strips comprises only test strips specifically used to indicate a predetermined condition, and
wherein the predetermined condition comprises chronic kidney disease (CKD), glucose levels, opiate levels, albumin to creatinine ratio, human chorionic gonadotropin (hCG) levels, specific gravity, pH levels, protein levels, ketone levels, bilirubin levels, nitrite levels, or leukocytes levels.

13. The system of claim 11, further comprising a platen, wherein the platen:
is positioned between the opposing reels;
is positioned underneath the belt and at least one of the plurality of test strips; and
increases the tension of the belt by raising the belt to a position above the reels.

14. The system of claim 13, wherein the platen has rounded edges.

15. The system of claim 1,
wherein the sensor comprises a complementary metal-oxide-semiconductor (CMOS) sensor and a light excitation source, and
wherein the captured image of the first test strip comprises a light intensity profile of the first test strip.

16. The system of claim 1,
wherein the captured image comprises a red-green-blue (RGB) picture of the first test strip,
wherein the computing device is configured to:
crop the RGB picture;
convert the RGB picture to a grayscale image;
convert the grayscale image to a binary image using a first threshold;
perform morphological operations to fill any holes in the binary image to generate a modified binary image, wherein the morphological operations comprise:
defining a kernel size;
performing an open operation with the kernel; and
performing a close operation with the kernel;
apply a Laplacian gradient to the modified binary image;
calculate a sum of each row generated by the Laplacian gradient applied to the modified binary image; and
set a second threshold and counting peaks across the modified binary image.

17. The system of claim 1, further comprising a toilet associated with the collection component, wherein the collection component is installed above or near a toilet bowl of the toilet, wherein the collection component being configured to be activated based on patient input comprises the collection component being configured to be activated when a toilet lid of the toilet or a toilet seat of the toilet is brought downward by the patient or by an additional motor, and wherein the collection component is made of polypropylene, silicone, polytetrafluoroethylene (PTFE/TEFLON®), or borosilicate glass.

18. The system of claim 1, further comprising a toilet associated with the collection component, wherein the collection component is installed above or near a toilet bowl of the toilet, and wherein transporting the second portion of the sample through the fourth tube comprises passing the second portion of the sample through an exit end of the fourth tube and into the toilet bowl.

19. A method comprising:
activating a collection component based on input from a patient;
receiving a sample from the patient in the collection component, wherein the collection component comprises smooth sides so as to minimize a residual amount of sample that sticks on walls of the collection component after patient use;
transporting a first portion of the sample from the collection component to a predetermined position relative to the collection component using a fluid transportation system, wherein the fluid transportation system comprises a sample volume control component, and wherein transporting the first portion of the sample from the collection component to the predetermined position comprises:
transporting the sample through a first tube of the sample volume control component;
separating the sample into the first portion and a second portion using a three-way valve of the sample volume control component;
transporting the first portion of the sample through a second tube of the sample volume control component via the three-way valve, wherein the second tube is connected to the first tube via the three-way valve;
transporting the second portion of the sample through a third tube of the sample volume control component via the three-way valve when the second tube is substantially full with the first portion of the sample, wherein the third tube is connected to the first tube via the three-way valve; and
transporting the second portion of the sample through a fourth tube of the sample volume control component;
exposing, by the fluid transportation system, a first test strip to the first portion of the sample, wherein the first test strip is one of a plurality of test strips configured to indicate a condition of the patient when exposed to the sample;
delivering, by the fluid transportation system, fresh water or another cleaning solution to the collection component to clean the collection component;
positioning, by a motor, the first test strip near a sensor;

capturing an image of the first test strip using the sensor, wherein the image indicates the condition of the patient;
positioning, by the motor, a second test strip of the plurality of test strips at the predetermined position;
analyzing, by a computing device, the image of the first test strip in order to determine the condition of the patient; and
deactivating the collection component.

* * * * *